(12) United States Patent
Moellering et al.

(10) Patent No.: US 12,209,143 B2
(45) Date of Patent: Jan. 28, 2025

(54) VERSATILE PEPTIDE AND PROTEIN MACROCYCLIZATION AND MULTIMERIZATION WITH DIELS-ALDER CYCLOADDITIONS

(71) Applicant: The University of Chicago, Chicago, IL (US)

(72) Inventors: Raymond E. Moellering, Chicago, IL (US); Jeffrey E. Montgomery, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 127 days.

(21) Appl. No.: 17/602,044

(22) PCT Filed: Apr. 9, 2020

(86) PCT No.: PCT/US2020/027531
§ 371 (c)(1),
(2) Date: Oct. 7, 2021

(87) PCT Pub. No.: WO2020/210535
PCT Pub. Date: Oct. 15, 2020

(65) Prior Publication Data
US 2022/0194985 A1 Jun. 23, 2022

Related U.S. Application Data

(60) Provisional application No. 62/831,484, filed on Apr. 9, 2019, provisional application No. 62/894,478, filed on Aug. 30, 2019.

(51) Int. Cl.
*C07K 7/50* (2006.01)
*C07K 1/04* (2006.01)
*C07K 1/10* (2006.01)

(52) U.S. Cl.
CPC .................. *C07K 7/50* (2013.01); *C07K 1/04* (2013.01); *C07K 1/10* (2013.01)

(58) Field of Classification Search
CPC ... C07K 7/50; C07K 1/04; C07K 1/10; C07K 7/08; C07K 7/06; C07K 14/001; C40B 40/10
See application file for complete search history.

(56) References Cited

U.S. PATENT DOCUMENTS

| | | | |
|---|---|---|---|
| 8,552,183 B2 | 10/2013 | Wiessler et al. | |
| 8,889,632 B2 | 11/2014 | Bernal et al. | |
| 9,163,330 B2 | 10/2015 | Verdine et al. | |
| 2003/0191704 A1 | 10/2003 | Alb | |
| 2011/0144306 A1 | 6/2011 | Verdine et al. | |
| 2012/0270800 A1 | 10/2012 | Verdine et al. | |
| 2014/0206852 A1 | 7/2014 | Hoge et al. | |
| 2014/0256912 A1 | 9/2014 | Moellering et al. | |
| 2015/0376227 A1 | 12/2015 | Verdine et al. | |
| 2018/0236065 A1 | 8/2018 | Mudde et al. | |
| 2019/0092810 A1 | 3/2019 | Chou et al. | |
| 2019/0135868 A1 | 5/2019 | Moellering et al. | |
| 2022/0194985 A1 | 6/2022 | Moellering et al. | |

FOREIGN PATENT DOCUMENTS

| | | |
|---|---|---|
| CN | 108148115 A | 6/2018 |
| WO | WO 97/14706 A1 | 4/1997 |
| WO | WO 2011/008260 A1 | 1/2011 |
| WO | WO 2012/174423 A1 | 12/2012 |
| WO | WO 2014/180889 A1 | 11/2014 |
| WO | WO 2016/170107 A1 | 10/2016 |
| WO | WO 2016/209978 A2 | 12/2016 |
| WO | WO 2017/190061 A1 | 11/2017 |
| WO | WO 2018/106842 A1 | 6/2018 |
| WO | WO 2020/210535 A1 | 10/2020 |

OTHER PUBLICATIONS

Jagasia et al (J.Org.Chem., 2009, 74, 2964-2974) (Year: 2009).*
Haufe et al (Chem.Ber., 1987, 120, 2007-2013) (Year: 1987).*
Balraju et al., "Synthesis of Cyclic Peptides Using a Palladium-Cyclized Enzyme Cycloisomerization," *Tetrahedron Letters*, 47(21): 3569-3571 (May 2006).
Bernal et al., "Reactivation of the p53 tumor suppressor pathway by a stapled p53 peptide," *J Am Chem Soc*, 129 (9), 2456-2457 (Mar. 2007), Author manuscript as published in PubMed.
Bhattacharya et al., "Solution structure of a hydrocarbon stapled peptide inhibitor in complex with monomeric C-terminal domain of HIV-1 capsid," *J Biol Chem*, 283 (24), 16274-16278 (Jun. 2008).
Chu et al., "Towards understanding cell penetration by stapled peptides." *Med Chem Comm*, 6 (1), 111-119 (Oct. 2014).
Dang, "Rethinking the Warburg effect with Myc micromanaging glutamine metabolism," *Cancer Res*, 70 (3), 859-862 (Feb. 2010).
Darnell, Jr., "Transcription factors as targets for cancer therapy," *Nature Rev Cancer*, 2 (10), 740-749 (Oct. 2002).
De Araujo et al., "Diels-Alder Ligation of Peptides and Proteins," *Chem. Eur. J.*, 12:6095-6109 (Aug. 2006).
Futaki et al., "Arginine-rich Peptides: an abundant source of membrane-permeable peptides having potential as carriers for intracellular protein delivery," *J Biol Chem*, 276(8): 5836-5840 (Feb. 2001).
Grossman et al., "Inhibition of oncogenic Wnt signaling through direct targeting of beta-catenin," *Proc Natl Acad Sci USA*, 109 (44), 17942-17947 (Oct. 2012).

(Continued)

*Primary Examiner* — Sudhakar Katakam

(74) *Attorney, Agent, or Firm* — Leydig, Voit & Mayer, Ltd.

(57) ABSTRACT

The present disclosure provides macrocyclic and macrobicyclic peptides with secondary structures that are stabilized over the corresponding non-cyclic peptides. The macrocyclic and macrobicyclic peptides are formed from peptides with adduct-forming, complementary reactive side chain moieties.

12 Claims, 50 Drawing Sheets

Specification includes a Sequence Listing.

(56) References Cited

OTHER PUBLICATIONS

Hilinski et al., "Stitched alpha-helical peptides via bis ring-closing metathesis," *J Am Chem Soc*, 136 (35), 12314-12322 (Sep. 2014).
Hopkins et al., "The druggable genome," *Nat Rev Drug Discov*, 1 (9), 727-730 (Sep. 2002).
Iyer et al., "Stapling monomeric GCN4 peptides allows for DNA binding and enhanced cellular uptake," *Org. Biomol. Chem.*, 13 (13), 3856-3862 (Apr. 2015).
Kohler et al., "DNA specificity enhanced by sequential binding of protein monomers," *Proc Natl Acad Sci USA*, 96 (21), 11735-11739 (Oct. 1999).
Landt et al., "ChIP-seq guidelines and practices of the ENCODE and modENCODE consortia," *Genome Res*, 22 (9), 1813-1831 (Sep. 2012).
Larochelle et al., "Fluorescence correlation spectroscopy reveals highly efficient cytosolic delivery of certain penta-arg proteins and stapled peptides," *J Am Chem Soc*, 137 (7), 2536-2541 (Feb. 2015), Author manuscript as published in PubMed.
Mardis, "ChIP-seq: welcome to the new frontier," *Nat Methods*, 4 (8), 613-614 (Aug. 2007).
Marsault et al., "Macrocycles Are Great Cycles: Applications, Opportunities and Challenges of Synthetic Macrocycles," *Drug Discovery in Journal of Medicinal Chemistry*, 54: 1961-2004 (Apr. 2011).
Metallo et al., "Distribution of labor among bZIP segments in the control of DNA affinity and specificity," *Chem Biol*, 1 (3), 143-151 (Nov. 1994).
Miller et al., "Synthesis of hydrogen-bond surrogate alpha-helices as inhibitors of protein-protein interactions," *Curr Protoc Chem Biol*, 6 (2), 101-116 (Jun. 2014), Author manuscript as published in PubMed.
Mitra et al., "Stapled peptide inhibitors of RAB25 target context-specific phenotypes in cancer," *Nat Comm* 8 (660), 1-11 (Sep. 2017).
Moellering et al., "Direct inhibition of the NOTCH transcription factor complex," *Nature*, 462 (7270), 182-188 (Nov. 2009), Author manuscript as published in PubMed.
Moellering et al., "Functional lysine modification by an intrinsically reactive primary glycolytic metabolite," *Science*, 341 (6145), 549-553 (Aug. 2013), Author manuscript as published in PubMed.
Montgomery et al., "Diels-Alder Cycloadditions for Peptide Macrocycle Formation," Ch. 9 in "Peptide Macrocycles: Methods and Protocols, Methods in Molecular Biology," Matthew B. Coppock and Alexander J. Winton (eds.), vol. 2371, 159-174 (Oct. 2021).
Montgomery et al., "Versatile peptide macrocyclization with Diels-Alder cycloadditions," *J Am Chem Soc*, 141(41): 16374-16381 (Oct. 16, 2019) Author manuscript as published in PubMed.
Nair et al., "X-ray structures of Myc-Max and Mad-Max recognizing DNA. Molecular bases of regulation by proto-oncogenic transcription factors," *Cell*, 112 (2), 193-205 (Jan. 2003).
Rauscher et al., "Fos and Jun bind cooperatively to the AP-1 site: reconstitution in vitro," *Genes & Development*, 2: 1687-1699 (Dec. 1988).
Schafmeister et al., "An all-hydrocarbon cross-linking system for enhancing the helicity and metabolic stability of peptides," *J Am Chem Soc*, 122 (24), 5891-5892 (Jun. 2000).
Soucek et al., "Modelling Myc inhibition as a cancer therapy," *Nature*, 455 (7213), 679-683 (Oct. 2008), Author manuscript as published in PubMed.
Subramanian et al., "Gene set enrichment analysis: a knowledge-based approach for interpreting genome-wide expression profiles," *Proc Natl Acad Sci USA*, 102 (43), 15545-15550 (Oct. 2005).
Testa, "Non conventional synthetic strategies of stapled peptides: modulation of secondary structures to optimize biological recognition," *PhD Thesis of The University of Cergy-pontoise, Co-Tutored with The University of Florence*, 191 pp. (Mar. 2012).
Uil et al., "Therapeutic modulation of endogenous gene function by agents with designed DNA-sequence specificities," *Nucleic Acids Res.*, 31 (21), 6064-6078 (Nov. 2003).

U.S. Patent and Trademark Office, Corrected International Search Report and Written Opinion in International Patent Application No. PCT/US2020/27531, 13 pp. (Nov. 4, 2020).
U.S. Patent and Trademark Office, International Search Report in International Patent Application No. PCT/US2020/27531, 5 pp. (Sep. 4, 2020).
U.S. Patent and Trademark Office, International Preliminary Report on Patentability in International Patent Application No. PCT/US2020/27531, 7 pp. (Sep. 28, 2021).
U.S. Patent and Trademark Office, Written Opinion in International Patent Application No. PCT/US2020/27531, 5 pp. (Sep. 4, 2020).
Walensky et al., "Activation of apoptosis in vivo by a hydrocarbon-stapled BH3 helix," *Science*, 305 (5689), 1466-1470 (Sep. 2004), Author manuscript as published in PubMed.
Walz et al., "Activation and repression by oncogenic MYC shape tumour-specific gene expression profiles," *Nature*, 511 (7510), 483-487 (Jul. 2014), Author manuscript as published in PubMed.
Ye et al., "Small Molecule Inhibitors Targeting Activator Protein 1 (AP-1)," *J Med Chem*, 57: 6930-6948 (Aug. 2014).
Bunner et al., "Expanding Peptide Stapling with S-Tetrazine," retrieved from the internet: https://repository.upenn.edu/edissertations/3374 on Mar. 21, 2023 (Aug. 28, 2019), 243 pp.
Bunner et al., "Expanding Peptide Stapling With S-Tetrazine Recommended Citation Expanding Peptide Stapling With S-Tetrazine", retrieved from the internet: https://repository.upenn.edu/cgi/viewcontent.cgi? on Mar. 20, 2023 (Aug. 28, 2019), 2 pp. abstract.
European Patent Office, Supplementary European Search Report in European Patent Application No. 20788557.5 (Jun. 30, 2023), 16 pp.
European Patent Office, Supplementary Partial European Search Report in European Patent Application No. 20788557.5 (Mar. 29, 2023), 18 pp.
Hyunil Jo et al., "Development of alpha-Helical Calpain Probes by Mimicking a Natural Protein-Protein Interaction," *Journal of the American Chemical Society*, 134(42): 17704-17713 (Oct. 24, 2012).
Iegre et al., "Two-Component Stapling of Biologically Active and Conformationally Constrained Peptides: Past, Present, and Future," *Advanced Therapeutics*, 1(7), 1800052 (Nov. 1, 2018), 22 pp., published online Aug. 7, 2018.
Junying Ma, "Discussion on Diels-Alder Reaction," *Journal of Pingdingshan Teachers College*, 15(4), (Nov. 2000), 6 pp.
U.S. Appl. No. 16/096,609, filed Oct. 25, 2018.
U.S. Appl. No. 18/038,633, filed May 24, 2023.
U.S. Appl. No. 18/534,086, filed Dec. 8, 2023.
Adams et al., "PHENIX: A Comprehensive Python-based System for Macromolecular Structure Solution," *Acta. Crystallogr. D. Biol. Crystallogr.*, 66(Pt 2): 213-221 (Jan. 2010).
Bi et al., "Enhancer Reprogramming Driven by High-order Assemblies of Transcription Factors Promotes Phenotypic Plasticity and Breast Cancer Endocrine Resistance," *Nat. Cell. Biol.*, 22(6): 701-715 (May 2020), Author manuscript as published in PubMed.
Bird et al., "Synthesis and Biophysical Characterization of Stabilized α-Helices of BCL-2 Domains," *Methods. Enzymol.*, 446: 369-386 (Jul. 2008), Author manuscript as published in PubMed.
Brownlie et al., "The Crystal Structure of an Intact Human Max-DNA Complex: New Insights into Mechanisms of Transcriptional Control," *Structure.*, 5(4): 509-520 (Apr. 1997).
Emsley et al., "Features and Development of Coot," *Acta. Crystallogr. D. Biol. Crystallogr.*, 66 (Pt 4): 486-501 (Apr. 2010).
Haufe et al., "Studies on the Stereoselectivity of Intramolecular Cycloadditions," *Chem. Ber.*, 120: 2007-2013 (Dec. 1987).
Jagasia et al., "Peptide Cyclization and Cyclodimerization by $Cu^I$-Mediated Azide-Alkyne Cycloaddition," *J. Org. Chem.*, 74(8): 2964-2974 (Mar. 2009).
Kim et al., "Synthesis of All-Hydrocarbon Stapled α-Helical Peptides by Ring-closing Olefin Metathesis," *Nat. Protoc.*, 6(6): 761-771 (May 2011).
Lin et al., "Transcriptional Amplification in Tumor Cells with Elevated c-Myc," *Cell*, 151(1): 56-67 (Sep. 2012), Author manuscript as published in PubMed.

(56) References Cited

OTHER PUBLICATIONS

Minor et al., "HKL-3000: the Integration of Data Reduction and Structure Solution—from Diffraction Images to an Initial Model in Minutes," *Acta. Crystallogr. D. Biol. Crystallogr.*, 62 (Pt 8): 859-866 (Aug. 2006).

Shim et al., "A New i, i + 3 Peptide Stapling System for α-Helix Stabilization," *Chem. Biol. Drug Des.*, 82(6): 635-642 (Sep. 2013).

Speltz et al., "Targeting MYC with Modular Synthetic Transcriptional Repressors Derived from bHLH DNA-binding Domains," *Nat. Biotechnol.*, 41(4): 541-551 (Oct. 2022).

Verdine et al., "Stapled Peptides for Intracellular Drug Targets," *Methods Enzymol.*, 503: 3-33 (Jan. 2012).

Wolfe et al., "Combining structure-based design with phage display to create new Cys(2)His(2) zinc finger dimers," *Structure*, v.8, 739-750 (2000).

U.S. Patent and Trademark Office, Written Opinion of the International Searching Authority, Application No. PCT/US2017/030217, 7 pp. (Sep. 15, 2017).

U.S. Patent and Trademark Office, International Search Report, Application No. PCT/US2017/030217, 6 pp. (Sep. 15, 2017).

U.S. Patent and Trademark Office, International Search Report in International Patent Application No. PCT/US2021/060808, 5 pp. (May 12, 2022).

U.S. Patent and Trademark Office, International Preliminary Report on Patentability in International Patent Application No. PCT/US2021/060808, 8 pp. (May 30, 2023).

\* cited by examiner

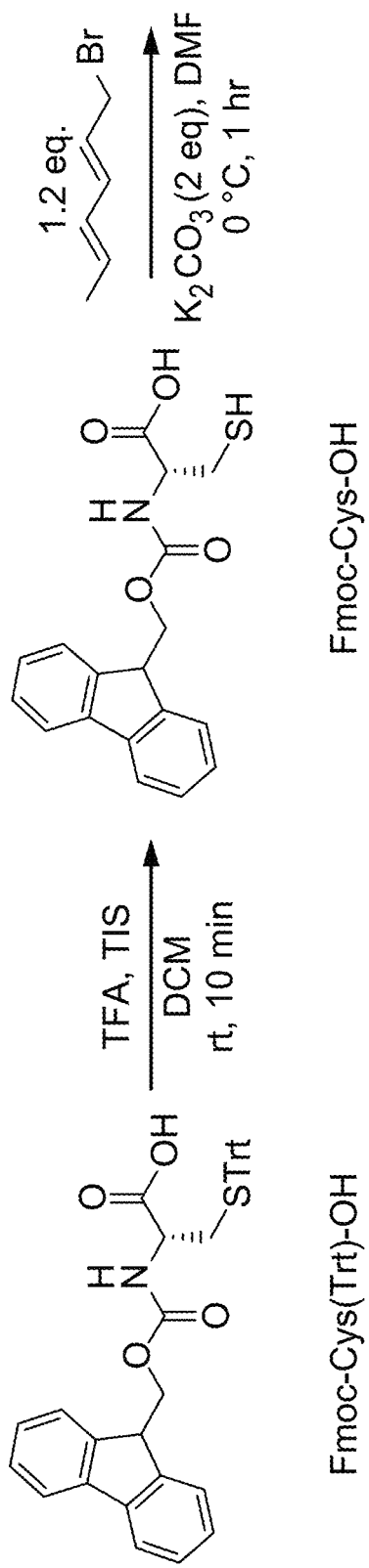
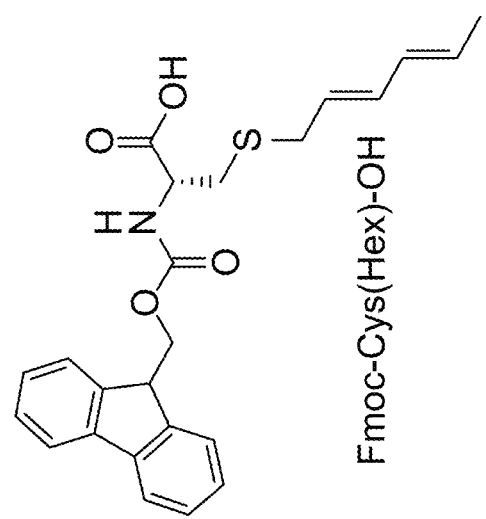
FIG. 3

| SEQ ID NO: | sequence | compound(s) | % conv. | product ratio* | retention time (min) | m/z (calc./obs.) |
|---|---|---|---|---|---|---|
| 15 | CRGDK | 1wt | - | - | 10.1 | 619.3 / 619.3 |
| 13 | C_tBuSRGDK | 1tBuS | - | - | 10.8 | 707.3 / 707.3 |
| 14 | C_HexRGDK | 1hex | quant. | - | 11.3 | 699.4 / 699.3 |
| 1 | C_HexRGDK_Mal | 1, 1a, 1b | 95 | >50:1 | 12.4, 11.2, 9.1 | 836.4 / 836.3 |
| 16 | C_tBuSVGDK | 2tBuS | - | - | 12.2 | 650.8 / 650.3 |
| 17 | C_HexVGDK | 2hex | quant. | - | 12.5 | 641.8 / 642.4 |
| 2 | C_HexVGDK_Mal | 2, 2a, 2b, 2c | 92 | 9:1 | 13.8, 11.9, 11.8, 9.9 | 778.9 / 779.3 |
| 18 | C_tBuSAPVYK | 3tBuS | - | - | 13.6 | 810.1 / 809.3 |
| 19 | C_HexAPVYK | 3hex | quant. | - | 13.7 | 802.0 / 801.4 |
| 3 | C_HexAPVYK_Mal | 3, 3a, 3b, 3c | 89 | 8:1 | 14.7, 13.1, 13.2, 11.0 | 939.1 / 938.3 |
| 20 | CAVPAVYK | 4wt | - | - | 13.1 | 891.5 / 891.3 |
| 21 | C_tBuSAVPAVYK | 4tBuS | - | - | 14.0 | 980.3 / 980.4 |
| 22 | C_HexAVPAVYK | 4hex | quant. | - | 14.0 | 972.2 / 971.4 |
| 4 | C_HexAVPAVYK_Mal | 4, 4a, b, 4c | 85 | 9:1 | 15.3, 13.7, 13.8, 11.8 | 1109.3 / 1108.4 |

* Reaction conditions: 2-6 hr heating at 45 °C, on-resin, in DMSO.

FIG. 11

A
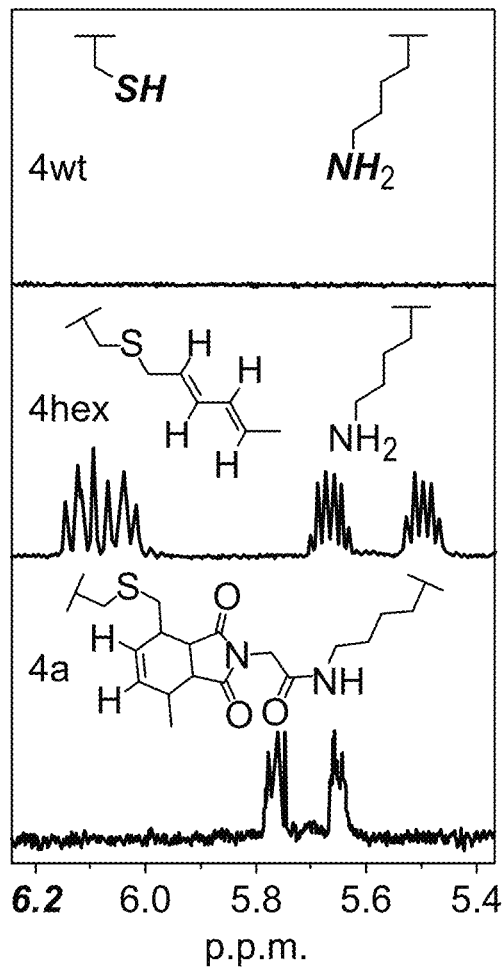
B
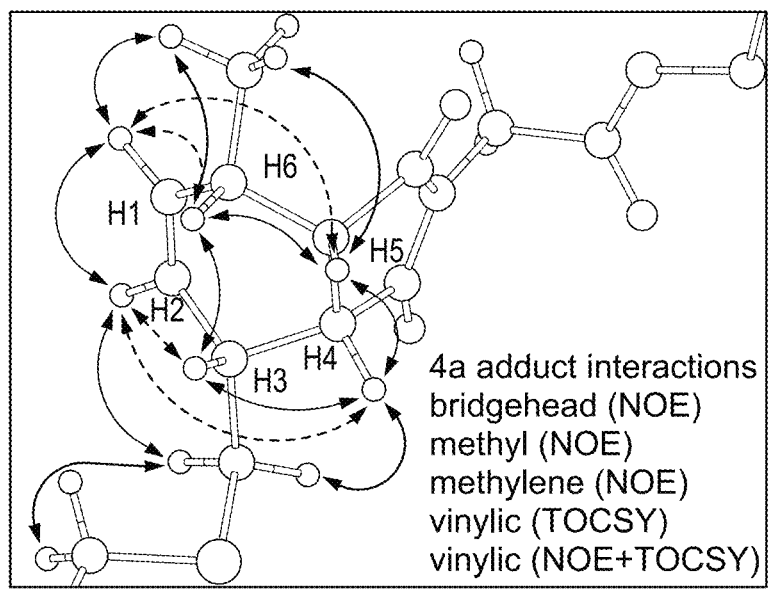
FIG. 12

| SEQ ID NO: | sequence | compound(s) | % conv. | product ratio* | retention time (min) | m/z (calc./obs.) |
|---|---|---|---|---|---|---|
| 24 | QSQQTFKNLWRLLA~~QN | 5pre | - | - | 15.3 | 1041.5/ 1041.3 |
| 25 | QSQQTFK~~NLWRLLA~~QN | 5, 5a, 5b, 5c | 88 | 6:1 | 15.6, 15.2, 15.0, 14.8 | 1110.1/ 1101.3 |
| 26 | HKILHRLLQDS | SRC2-WT | - | - | 11.1 | 700.9/ 701.0 |
| 30 | fitc-b-SLTERHKILHRLLQE | fitc-SRC1-BoxII | - | - | 12.3 | 778.1/ 778.2 |
| 31 | HKKLHRA~~LQDS | 6pre | - | - | 8.1 | 720.4/ 720.5 |
| 27 | HKK~~LHRA~~LQDS | 6, 6a, 6b | 95 | 4:1 | 8.9, 8.7, 8.2 | 788.9/ 788.8 |
| 32 | HKILHKLLQA~~S | 7pre | - | - | 10.2 | 697.9/ 698.0 |
| 29 | HKILHK~~LLQA~~S | 7, 7a, 7b, 7c | 95 | 7:1 | 11.4, 11.1, 10.9, 10.6 | 766.4/ 766.5 |
| 33 | HKS₃LHKS₃LQA~~S | 8pre | - | - | 11.6 | 723.9/ 724.0 |
| 33 | HKS₃'LHKS₃'LQA~~S | 8rcm | >95 | - | 11.2 | 709.9/ 710.0 |
| 28 | HKS₃'LHK~~S₃'LQA~~S | 8, 8a | >95 | - | 11.9, 11.0 | 778.4/ 778.5 |

* Reaction conditions: 2-6 hr heating at 45°C, on resin, in DMSO. Ratio reported as the DAC peptide major product:minor product(s).

FIG. 19 furan derivatives (fur)
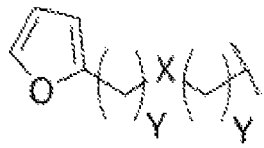
hexadiene derivatives (hex)
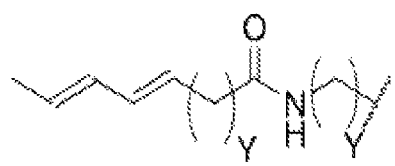
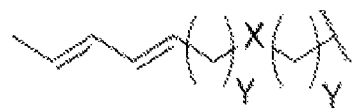
cyclohexadiene derivatives
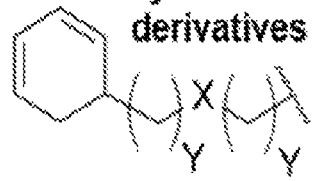
cyclopentadiene derivatives (cpd)
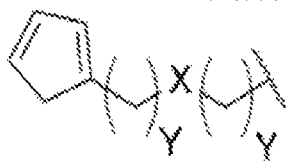
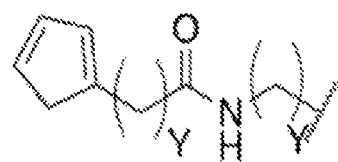
FIG. 23A unactivated alkene derivatives
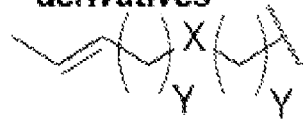
acrylyl derivatives (acr)
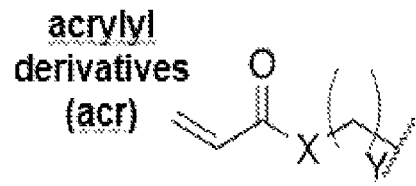
maleimido derivatives (mal)
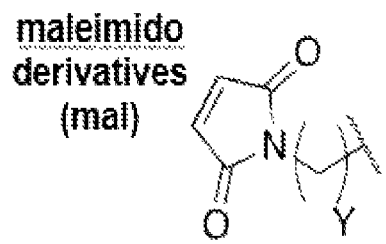
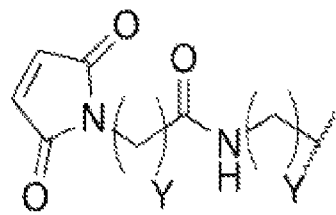
alkynyl derivatives
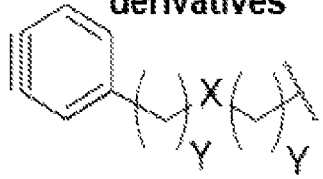
FIG. 23B SEQ ID NO: 7
Ac-SCFGGRK(Mmt)DRIGAQC(hex)GLGCNSF 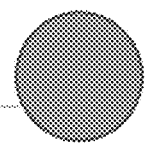
↓ i) 1% TFA/DCM; 5 × 3 min
ii) 4:4:4 glycyl-maleimide : HCTU : DIPEA; 15 min
SEQ ID NO: 8
Ac-SCFGGRK(mal)DRIGAQC(hex)GLGCNSF 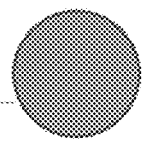
↓ i) Heating in DMSO, 45°C, 2 hr
ii) Peptide cleavage
SEQ ID NO: 8  
Ac-SCFGGRK(mal)DRIGAQC(hex)GLGCNSF
(DAC; reduced)
FIG. 24

DAC-ANP-1 (reduced)
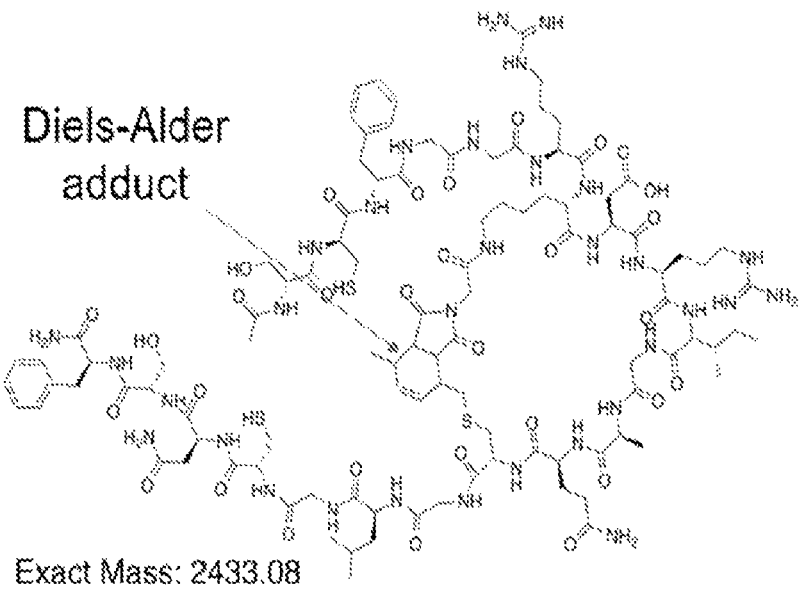
DAC-ANP-1 (oxidized)
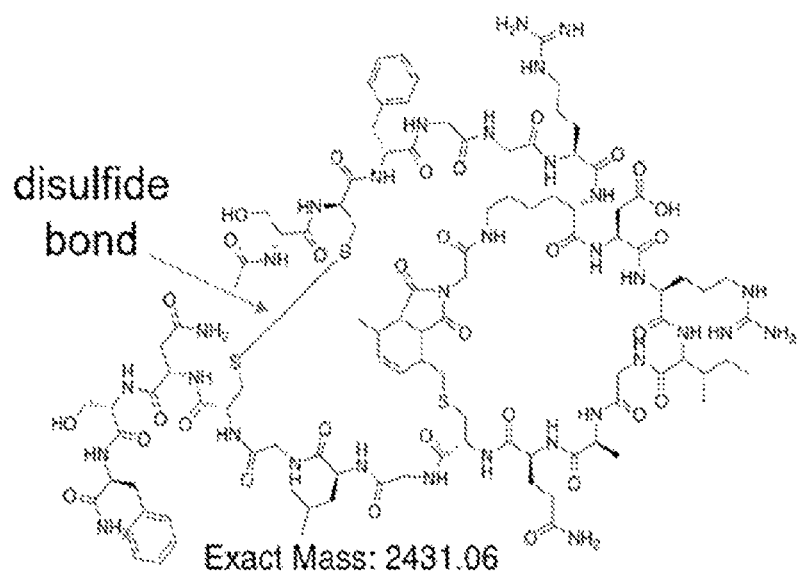
FIG. 25

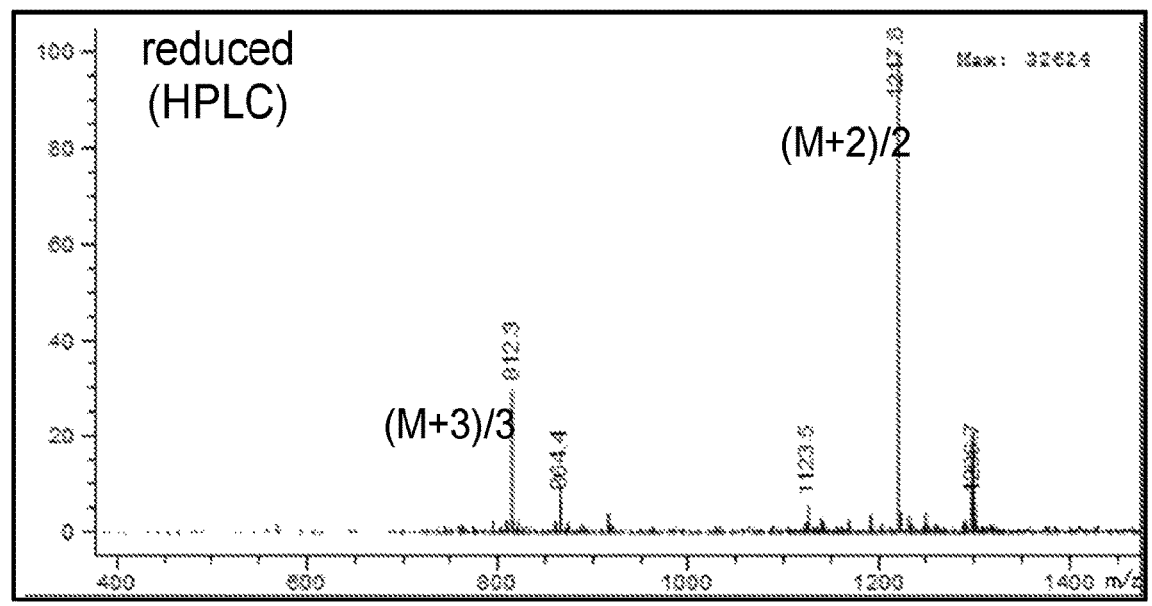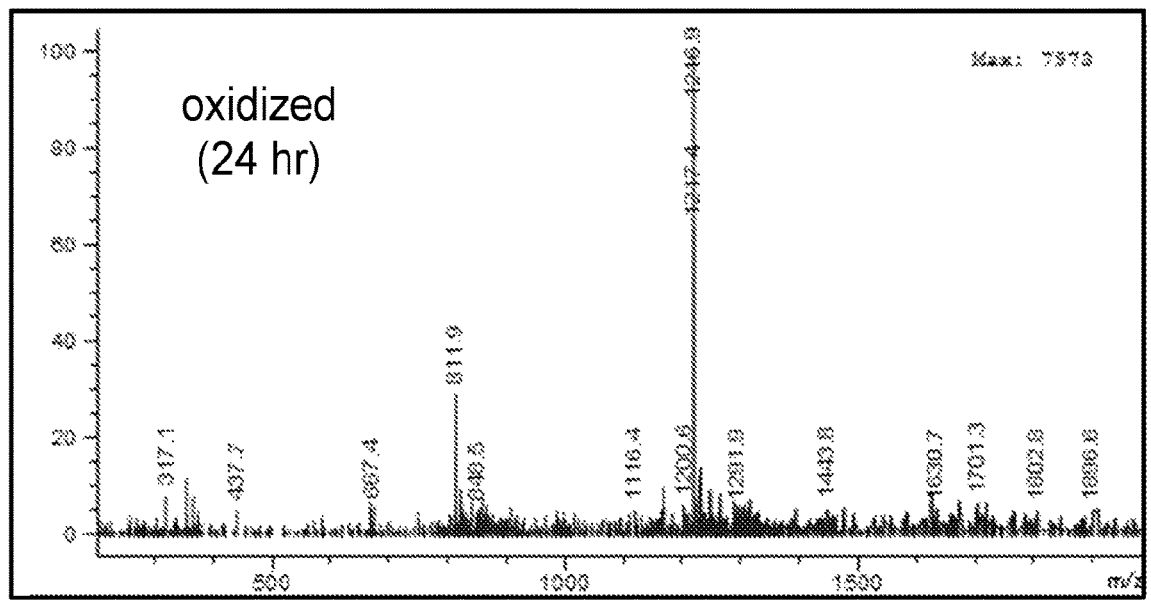
FIG. 26C

ANP-WT (reduced)
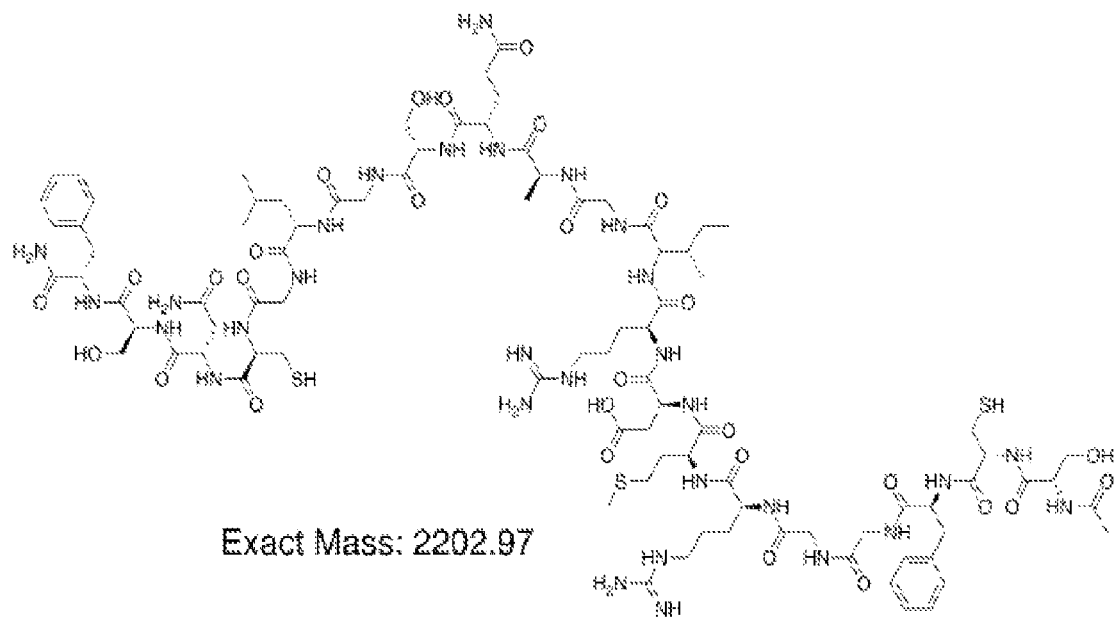
Exact Mass: 2202.97
ANP-WT (oxidized)
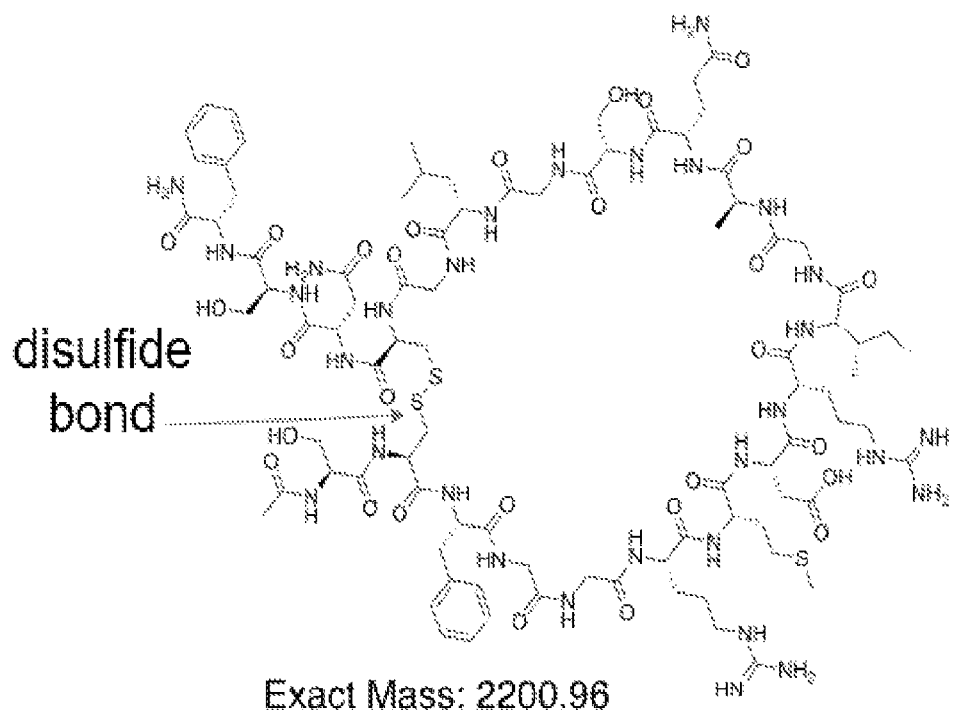
disulfide bond
Exact Mass: 2200.96
FIG. 27

RTD8 precursor peptide
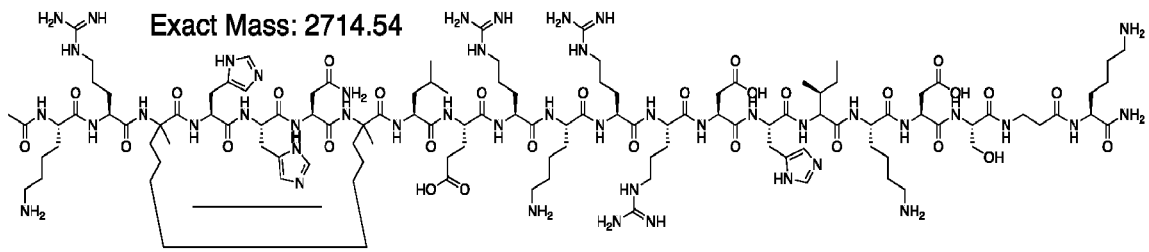
RTD8-cpd
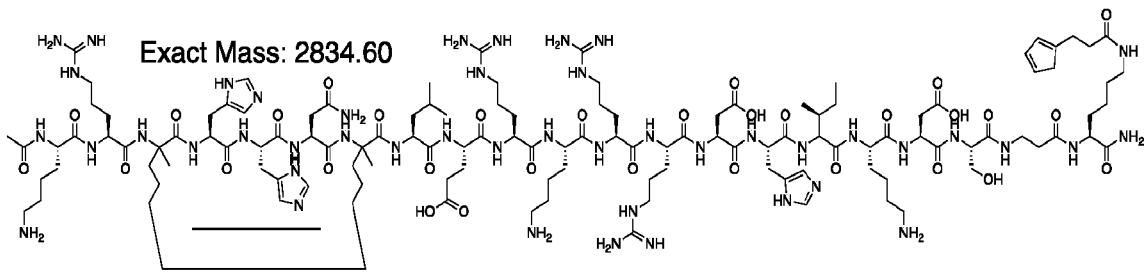
Diels-Alder dimerized RTD8
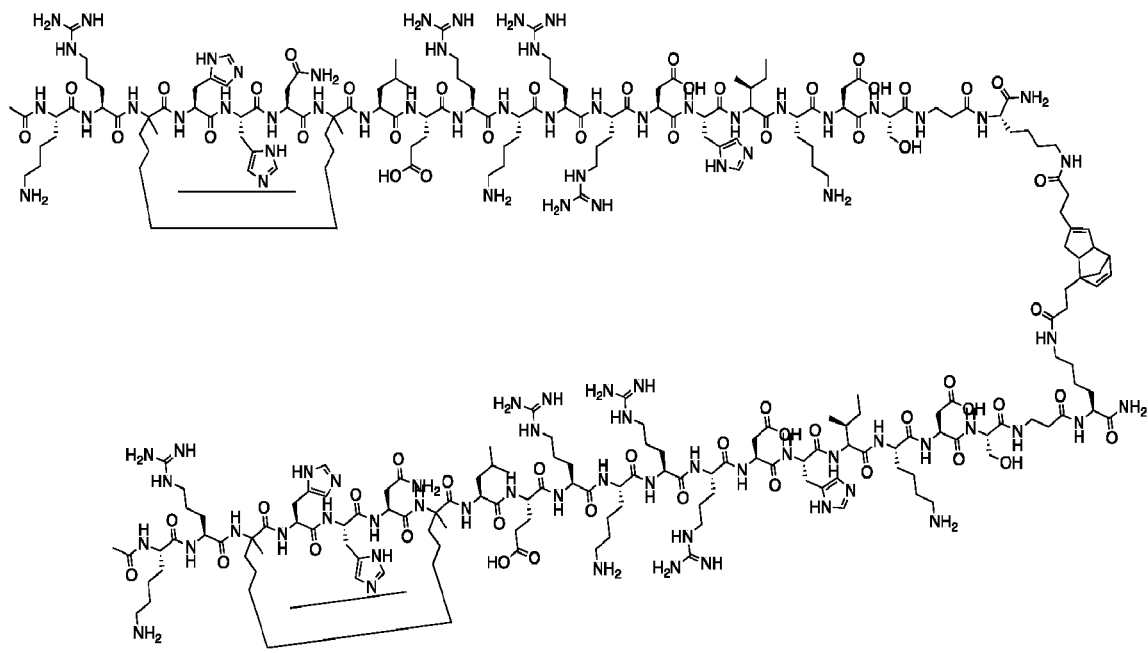
FIG. 32

SEQ ID NO: 34
Fmoc-β-WPQ*ILD*HVQEVWRRRRR
↓ 2x 20mol% Grubbs I
  DCE, 2 hr
SEQ ID NO: 34
Fmoc-β-WPQ*ILD*HVQEVWRRRRR
↓ i) 20% piperidine/DMF
  ii) 5 eq cpd-NHS/NMP
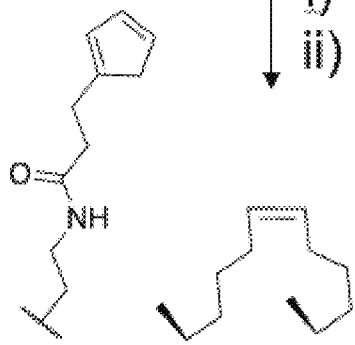
SEQ ID NO: 35   β-WPQ*ILD*HVQEVWRRRRR
↓ DMSO
  45°C, 16 hr
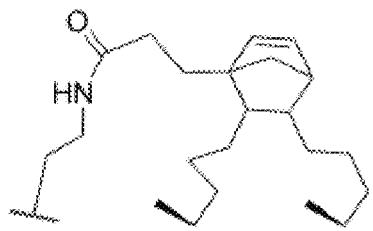
SEQ ID NO: 35   β-WPQ*ILD*HVQEVWRRRRR
FIG. 34

| | SEQ ID NO: | | |
|---|---|---|---|
| 05H_Mont_1609..hort (61-651) | 36 | 5 HHHHHHSSGLVPRGSHMGNGTEEDYNFVFKVVLIGESGVGKTNLLSRFTRNEFSHDSRTTIGVEFSTRTV | 74 |
| 12C_mont_RB_T7short (57-647) | 37 | 1 HHHHHHSSGLVPRGSHMGNGTEEDY FVFKVVLIGESGVGKTNLLSRFTRNEFSHDSRTTIGVEFSTRTV | 70 |
| 05H_Mont_1609..hort (61-651) | 36 | 75 MLGTAAVKAQIWDTAGLERYRAITSAYYRGAVGALLVFDLTKHQTYAVVERWLKELYDHAEATIVVMLVG | 144 |
| 12C_mont_RB_T7short (57-647) | 37 | 71 MLGTAAVKAQIWDTAGLERYRAITSAYYRGAVGALLVFDLTKHQTYAVVERWLKELYDHAEATIVVMLVG | 140 |
| 05H_Mont_1609..hort (61-651) | 36 | 145 NKSDLSQAREVPTEEARMFAENNGLLFLETSALDSTNVELAFETVLKEIFAKVSKQ* | 201 |
| 12C_mont_RB_T7short (57-647) | 37 | 141 NKSDLSQAREVPTEEARMFAENNGLLFLETSALDSTNVELAFETVLKEIFAKV KQ* | 197 |

FIG. 37

VERSATILE PEPTIDE AND PROTEIN MACROCYCLIZATION AND MULTIMERIZATION WITH DIELS-ALDER CYCLOADDITIONS

CROSS-REFERENCE TO RELATED APPLICATIONS

This patent application is a U.S. National Phase of International Patent Application No. PCT/US2020/027531, filed Apr. 9, 2020, which claims the benefit of U.S. Provisional Patent Application No. 62/831,484, filed Apr. 9, 2019, and U.S. Provisional Patent Application No. 62/894,478, filed Aug. 30, 2019, each of which is incorporated by reference herein in its entirety.

STATEMENT REGARDING FEDERALLY SPONSORED RESEARCH OR DEVELOPMENT

This invention was made with Government support under grants GM008720 and GM128199 awarded by the National Institutes of Health. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 15,781 Byte ASCII (Text) file named "757883-2_ST25.txt," created on May 15, 2023.

BACKGROUND OF THE INVENTION

Peptides represent powerful starting points for the development of bioactive ligands. Short linear peptide sequences mediate protein-protein interactions (PPIs) by adopting diverse secondary structures, including helix, sheet, loop and turn motifs. Removal from their native protein context often abrogates structural rigidity, leading to reduced binding affinity and pharmacologic properties.

Numerous chemical strategies have been developed to synthetically stabilize peptide secondary structure and retain or augment pharmacologic utility. Most of these chemistries capitalize on alkylation or acylation reactions on naturally-occurring nucleophilic residues such as cysteine and lysine; these approaches have been applied to stabilize helix, loop, and sheet motifs. A key limitation with many of these chemistries is their incompatibility with layering multiple stabilizing chemistries.

One strategy for synthesizing peptides with stabilized secondary structures involves the use of non-natural amino acids that enable metal-catalyzed bond formation. The most well-studied of these strategies include olefin metathesis of terminal alkene containing groups as well as [3+2] Huisgen ligation of alkyne/azide pairs. These 'stapled' peptides show increased favorable properties including structural stability, binding affinity, cellular uptake, and in vivo pharmacokinetics for direct or allosteric targeting of PPIs. While these chemistries can successfully stabilize peptide secondary structure, they are often incompatible with diverse structures, and other natural and non-natural functionalities and aqueous conditions are necessary for proper folding of specific peptide and protein scaffolds.

A notable carbon-carbon bond forming reaction that has enjoyed widespread synthetic application is the Diels-Alder [4+2] cycloaddition. First reported in 1928, this reaction is employed by nature and chemists alike to construct complex molecules. Several aspects of this transformation make it attractive for synthesis, including a wide range of diene-dienophile pairs, high regio- and chemoselectivity in many applications, simultaneous introduction of multiple stereocenters and compatibility with a range of reaction conditions. Pioneering studies demonstrated that aqueous conditions are not only tolerated, but can enhance reaction rates. While these qualities overlap with those desired for selective modification of biomolecules, this chemistry has not been applied for site-specific stabilization of peptides or proteins.

New strategies to control secondary and tertiary structure, ideally with wide functional group and reaction condition tolerance, would greatly expand the synthetic arsenal for developing peptide-based chemical probes.

SUMMARY OF THE INVENTION

The inventors have discovered complementary reactive functional group-directed peptide cyclization strategies that effectively improve desirable properties for chemical probes or therapeutics. The results disclosed herein establish several emergent and improved capabilities offered by the incorporation of amino acids with reactive functional groups that include complementary, adduct-forming moieties. The reactive functional groups may be conjugated to an amino acid side chain, or conjugated to any other part of an amino acid, including the amino group, carboxy group, or α-carbon. In some embodiments, the macrocyclic peptides disclosed herein are formed by intramolecular reaction of complementary reactive functional groups that result in stabilized loop, helical, and other desirable peptide folds. In some aspects, the peptides include two or more orthogonal sets of complementary reactive functional groups that enable the formation of bicyclic or higher order cyclized peptides. In some embodiments, reactive functional groups are introduced into larger peptides and proteins to form intramolecular crosslinks between secondary structural and tertiary structural elements.

Some embodiments of the disclosure are directed to a macrocyclic compound of the formula (I) wherein A, $A_1$, and $A_2$ are amino acids, each n is independently an integer from 0 to 600, for example 1, 2, 3, 4, 5, 6, 7, 8, 9, 10, 15, 20, 25, 30, 35, 40, 45, and 50 (except where attached to X, where n is at least 1), and X is an adduct between reactive functional groups.

(I)

In some embodiments, X is an adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s). In some aspects, at least one amino acid is a non-natural amino acid or an amino acid derivative. In some aspects, the reactive functional groups are each independently bound to an amino acid side chain, amino acid amino group, amino acid carboxy group, or amino acid α-carbon. In some aspects, X is bound to a side chain, amine group, carboxy group, or α-carbon of one amino acid and to a side chain, amine group, carboxy group, or α-carbon of a different amino acid within the same compound to provide a cyclic structure. In some embodiments, the macrocyclic compound is formed from a peptide in which one reactive functional group includes a diene and a different reactive functional group includes a dienophile. The complementary diene and dienophile pair can react to form a macrocyclic peptide through an intramolecular Diels-Alder reaction. In some aspects, X is an adduct between reactive functional groups bound to any two different amino acids in the compound. That is, the reactive functional groups may each independently be conjugated to a terminal amino acid or an internal amino acid. In some embodiments, one of $A_1$ and $A_2$ is cysteine or a cysteine derivative and the other is lysine or a lysine derivative. In some aspects, the cysteine and/or lysine are derivatized to form a diene or a dienophile. In some embodiments, X is formed from a reaction between a hexadiene group and a maleimide group, a maleimide group and a furan group, a cyclopentadiene group and another cyclopentadiene group, a cyclopentadiene group and a maleimide group, or a cyclopentadiene group and an aliphatic olefin (for example, an aliphatic olefin used as a peptide staple). In some aspects, X is one of the Diels-Alder adducts:

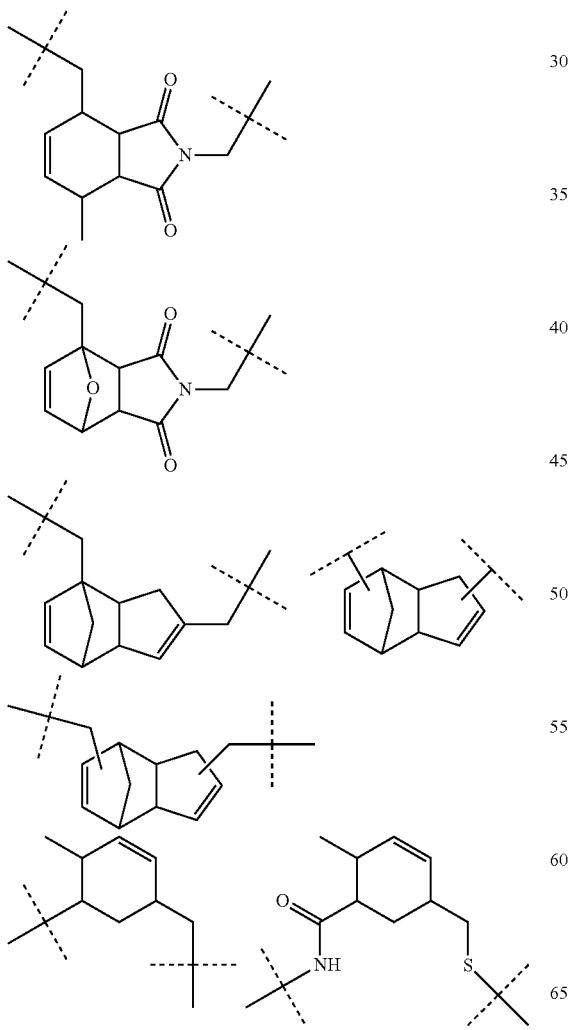

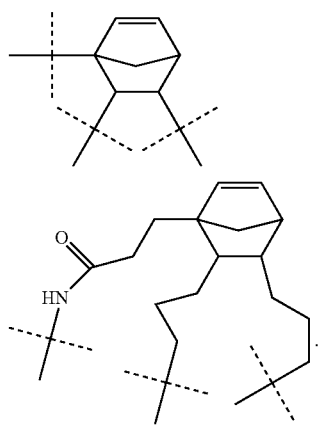

In some aspects, X is any one of the adducts presented in FIGS. 23C-23E.

Various permutations of compounds of Formula I are contemplated in which the reactive functional groups are bound to different amino acids and amino acid functional groups within the compound. The reactive functional groups may each be independently bound to an amino acid side chain, amino acid amino group, amino acid carboxy group, or amino acid α-carbon. Non-limiting examples of different permutations of compounds of Formula I include:

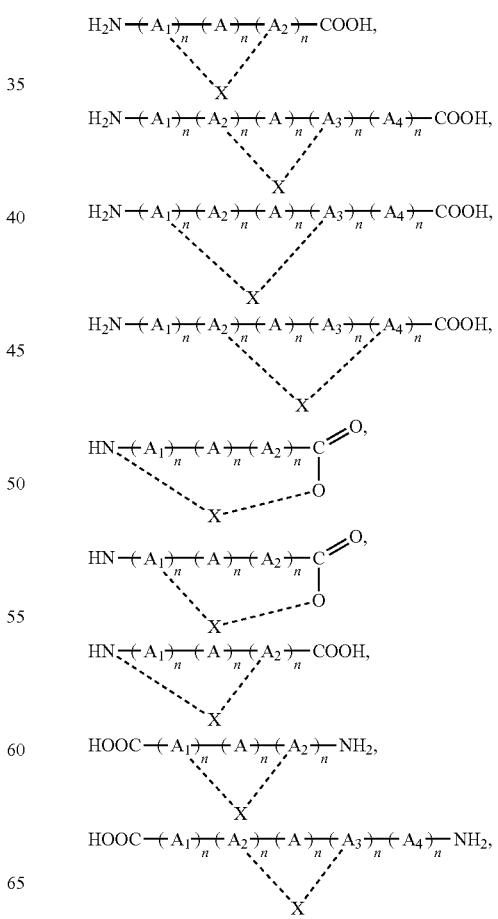

-continued

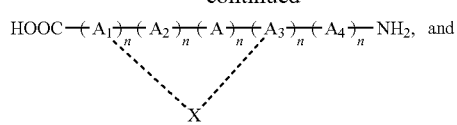

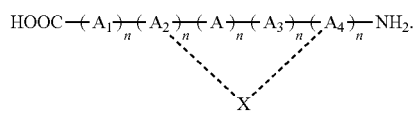

In specific embodiments, a compound of formula I is further defined as one of:

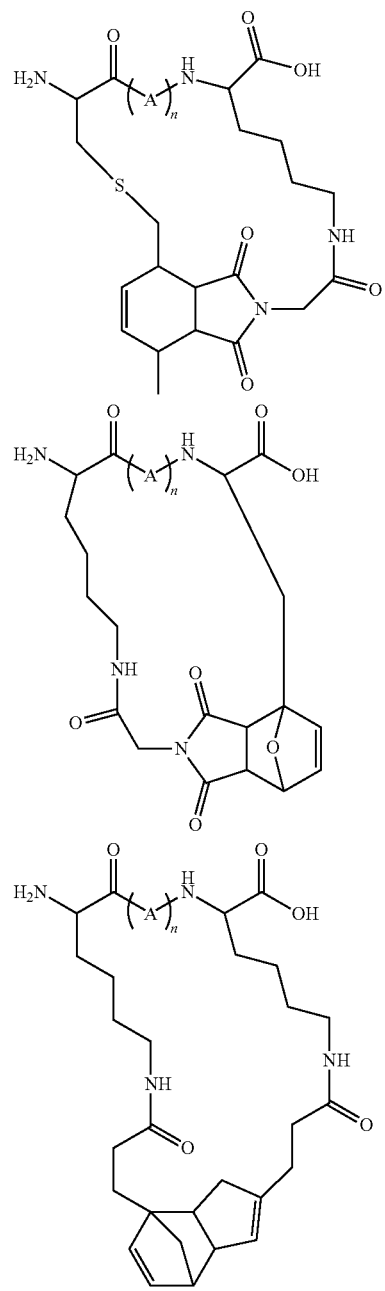

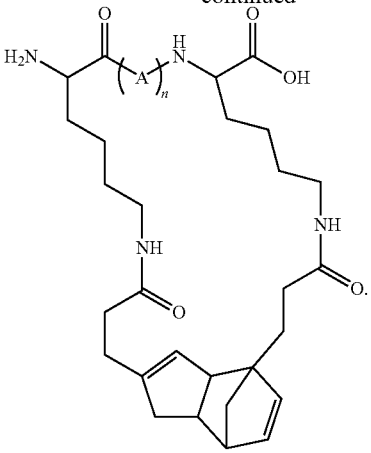

FIGS. 23C-23E present additional possible adducts and additional isomers of the cpd adduct.

Some aspects of the disclosure are directed to a method of synthesizing a macrocyclic or crosslinked compound comprising synthesizing a peptide of formula (II) where A, $A_1$, and $A_2$ are amino acids, each n is independently an integer from 0 to 600, for example 1, 2, 3, 4, 5, 6, 7, 8, 9, 10, 15, 20, 25, 30, 35, 40, 45, and 50 (except where attached to Y or Z, where n is at least 1), Y and Z are reactive moieties capable of undergoing a Y—Z conjugating reaction, and subjecting the compound to conditions that drive the Y—Z conjugating reaction to form an intramolecular Y—Z crosslinking moiety.

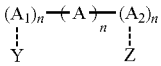

(II)

In some aspects, Y and Z are independently bound to the side chain, amino group, carboxy group, or α-carbon of different amino acids within the compound. In some embodiments, at least one amino acid is a non-natural amino acid or an amino acid derivative. In some embodiments, the Y—Z conjugating reaction is a cycloaddition reaction. In some aspects, the Y—Z conjugating reaction is a Diels-Alder reaction or an olefin-olefin metathesis reaction. In some aspects Y is a conjugated diene and Z is a dienophile. In embodiments, one of $A_1$ and $A_2$ is cysteine and the other is lysine, and the cysteine and/or lysine may be further derivatized to form a diene or a dienophile. Y may be any conjugated diene, including, but not limited to a conjugated diene present in a linear or cyclic structure, 2,4-hexadiene or a derivative thereof, furan or a derivative thereof, thiophene or a derivative thereof, or cyclopentadiene or a derivative thereof. Non-limiting examples of diene derivative functional groups include electron-donating groups such as alkyl, ester, amide, alkyloxy, hydroxyl, amine, and silyl ether. In some aspects, an electron-donating group is bound to an olefinic carbon atom that is part of the conjugated diene system. Z may be any dienophile, including but not limited to maleic anhydride or a derivative thereof, benzyne or a derivative thereof, quinone or a derivative thereof, an N-sulfinyl derivative, a sulfur-diimide derivative, an imino derivative, a nitroso derivative, a thionitroso derivative, acrylate or a derivative thereof, or crotonate or a derivative thereof. Non-limiting examples of dienophile derivative functional groups include electron-withdrawing groups such as ester, amide, nitro, sulfone, carbonyl, cyano, or haloalkane moieties. In some embodiments, the dienophile derivative functional group is bound to a carbon atom of the dienophile diene. In formulas (I) and (II) above, either $A_1$ or $A_2$ may be an N-terminus amino acid. In some embodiments, Y and Z are each independently linked to a side chain, amine, carboxy group, or α-carbon of any two different amino acids in the peptide. In some aspects, the peptide of formula (II) is further defined as one of:

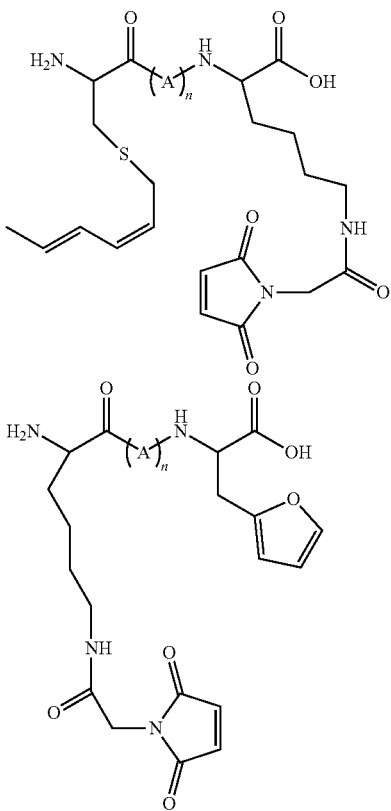

For cpd, any of the isomers of the cyclopentadiene are possible, e.g., having the cyclopentadiene attached at any carbon position of the ring:

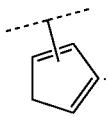

Some embodiments of the disclosure are directed to a bicyclic or higher-order cyclic compound of formula (III), where A, $A_1$, $A_2$, $A_3$, and $A_4$ are amino acids, each n is independently an integer from 0 to 600, for example 1, 2, 3, 4, 5, 6, 7, 8, 9, 10, 15, 20, 25, 30, 35, 40, 45, and 50 (with the sum of all n being at least 2), B is an adduct formed between complementarily-reactive functional groups, C is an adduct formed between complementarily-reactive functional groups. The reactive functional groups used to form the B and C adducts are each bound to a different amino acid side chain, amino acid amino group, amino acid carboxy group, or amino acid α-carbon. In some aspects, the reactive functional groups used to form the B adduct are orthogonal to the reactive functional groups used to form the C adduct. In some aspects, one of B or C is an adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s); and the other of B or C is a different adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s). In some embodiments, the B adduct and the C adduct are formed using different reaction types, e.g., one adduct is formed by a Diels-Alder reaction and the other adduct is formed by an olefin-metathesis reaction.

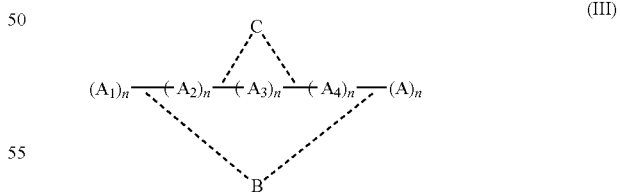

(III)

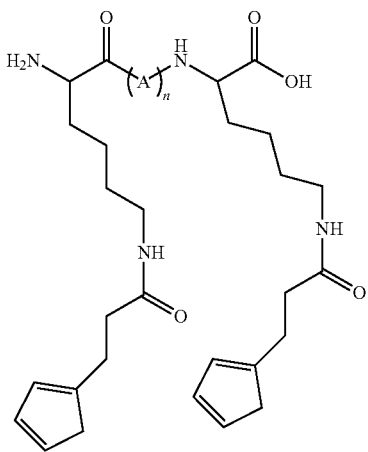

In some embodiments, the reactive functional groups used to form the C adduct are bound to amino acids that are internal to the two amino acids bound to the reactive functional groups used to form the B adduct, as depicted in formula (III). In some embodiments, the reactive functional groups used to form the B adduct are bound to amino acids that are internal to the two amino acids bound to the reactive functional groups used to form the C adduct, as depicted in formula (IV).

(IV)

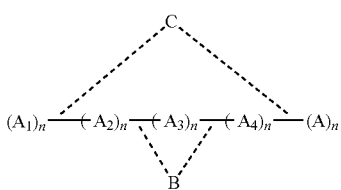

In some embodiments, the reactive functional groups used to form the B adduct are bound to amino acids that are in a staggered relationship with the amino acids bound to the reactive functional groups used to form the C adduct, as depicted in formula (V).

(V)

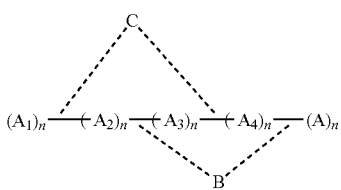

In some embodiments, the adducts B and C are bound to one another to form a higher-order cyclic compound, as depicted in formula (IIIa), formula (IIIb), formula (IVa), formula (IVb), or formula (Va).

(IIIa)

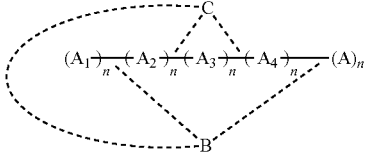

(IIIb)

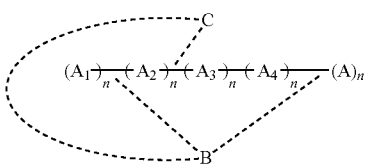

(IVa)

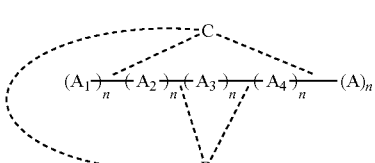

(IVb)

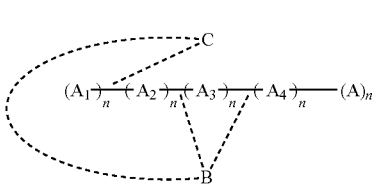

(Va)

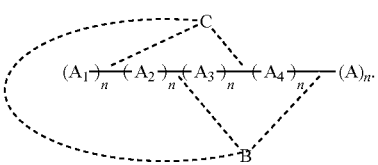

For example, the formation of B may be through olefin metathesis reaction, creating a complementary reactive group to react with diene, leading to another macrocycle C.

In some embodiments, at least one amino acid is a non-natural amino acid or an amino acid derivative.

Some aspects of the disclosure are directed to a method of synthesizing a bicyclic or higher-order cyclic compound comprising synthesizing a peptide of formula (VI) with complementarily-reactive functional groups D and E capable of undergoing a D-E conjugating reaction, and complementarily-reactive functional groups F and G capable of undergoing a F-G conjugating reaction, subjecting the peptide to conditions that drive the D-E conjugating reaction to form an intramolecular D-E crosslinking moiety, and subjecting the peptide to conditions that drive the F-G conjugating reaction to form an intramolecular F-G crosslinking moiety, wherein A, $A_1$, $A_2$, $A_3$, and $A_4$ are amino acids, and each n is independently an integer from 0 to 600, for example 1, 2, 3, 4, 5, 6, 7, 8, 9, 10, 15, 20, 25, 30, 35, 40, 45, and 50 (with the sum of all n being at least 2).

(VI)

$$(A_1)_n \text{—} (A_2)_n \text{—} (A_3)_n \text{—} (A_4)_n \text{—} (A)_n$$
with D above $(A_2)$, E above $(A_4)$, F below $(A_3)$, G below $(A_4)$...

In some aspects, reactive functional groups D, E F, and G are each independently bound to a different amino acid side chain, amino acid amino group, amino acid carboxy group, or amino acid α-carbon of any amino acid $A_1$ to A. In some embodiments, at least one of reactive functional groups D, E, F, and G is bound to a non-natural amino acid or an amino acid derivative. In some aspects, each of reactive functional groups D, E, F, and G is bound to a non-natural amino acid or an amino acid derivative.

In some embodiments, reactive functional group F and complementarily-reactive functional group G are bound to amino acids that are internal of amino acids bound to reactive functional group D and complementarily-reactive functional group E, as depicted in formula (VI). In further embodiments, reactive functional group D and complementarily-reactive functional group E are bound to amino acids that are internal of amino acids bound to reactive functional group F and complementarily-reactive functional group G, as depicted in formula (VII).

(VII)

$$(A_1)_n \text{—} (A_2)_n \text{—} (A_3)_n \text{—} (A_4)_n \text{—} (A)_n$$

In some embodiments, reactive functional group D and complementarily-reactive functional group E bound to amino acids that are in a staggered relationship with amino acids bound to reactive functional group F and complementarily-reactive functional group G, as depicted in formulas (VIII) and (IX).

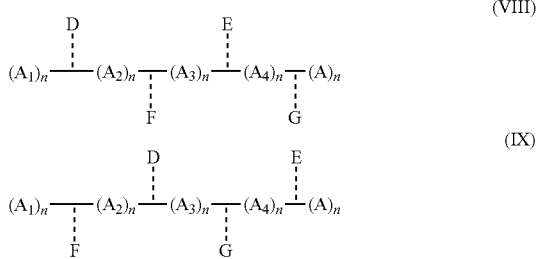

In some aspects, the D-E conjugating reaction or the F-G conjugating reaction is a Diels-Alder reaction. In some embodiments, the D-E conjugating reaction or the F-G conjugating reaction is a ring-closing metathesis reaction, a copper-catalyzed azide-alkyne click reaction, cystine formation via oxidation of two cysteine residues, crosslink formation via alkylation of one or more cysteine residues, a thiol-ene reaction, or a lactam bridge formation between N- or C-termini and/or residue side chain(s). In some embodiments, one of the D-E and F-G conjugating reactions is a Diels-Alder reaction and the other conjugating reaction is a ring-closing metathesis reaction. In formulas (III)-(IX) depicted above, either $A_1$ or A may be an N-terminus amino acid. In some aspects a molecule of formulas (III)-(IX) includes three or more macrocycles formed from a corresponding number of adduct-forming reactions. For example, a tricyclic compound can include adducts, H, I, and J, each of which is formed by reaction between complementarily-reactive functional groups pairs. A bicyclic or higher-order cyclic compound as disclosed herein may be constructed using complementarily-reactive functional groups pairs that are orthogonal to each other, may employ the use of protection/deprotection chemistries, and/or may be constructed using reactive functional groups pairs that are installed at different stages of the compound synthesis, so as to avoid undesired cross-reaction between certain reactive functional groups.

Some embodiments of the disclosure are directed to a polypeptide of the formula (X):

$$(A_1)_n\text{-}R^1\text{-}(A_2)_m \quad (X)$$

wherein $A_1$ and $A_2$ are amino acids; n and m are each independently integers from 2 to 600, for example 2, 3, 4, 5, 6, 7, 8, 9, 10, 15, 20, 25, 30, 35, 40, 45, and 50; the amino acids of A1 are N- to C-terminus, and the amino acids of A2 are C- to N-terminus; and IV is an adduct formed from a reaction between a cyclopentadiene group and another cyclopentadiene group. In some embodiments, $R^1$ is

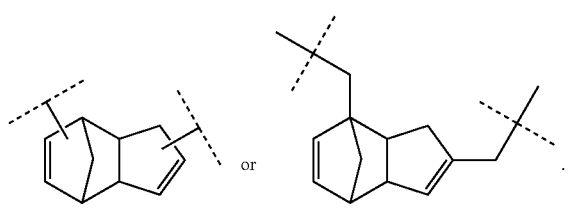

In some embodiments, the polypeptide of formula (X) is further defined as $(A_1)_{n-1}\text{-Lys-}R^1\text{-Lys-}(A_2)_{m-1}$.

Some embodiments of the disclosure are directed to a method of ligating a peptide or polypeptide, the method comprising reacting a first peptide or polypeptide to a second peptide or polypeptide, wherein the first peptide or polypeptide and the second peptide or polypeptide each comprise a cyclopentadiene group, and wherein upon reaction an adduct is formed between the cyclopentadiene group of the first peptide or polypeptide and the cyclopentadiene group of the second peptide or polypeptide. In some embodiments, the adduct is

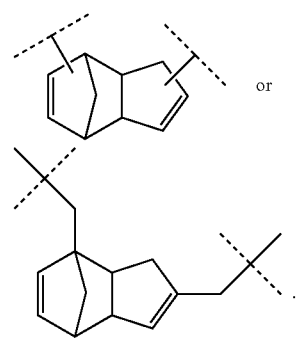

In some embodiments, the first and second peptide or polypeptide is the same and is homodimerized. In some embodiments, the method may be used to ligate more than two peptides or polypeptides.

The term "orthogonal" refers to functional groups that can react with a complementarily-reactive partner, but do not react with, or exhibit reduced reactivity to other reactive functional groups. As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment. Throughout this application, the term "about" is used according to its plain and ordinary meaning in the area of cell biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 Synthetic scheme for synthesis of Fmoc-Cys(2,4-hexadiene)-OH.

FIG. 5B Representative reaction time course quantifying conversion of 1 to cyclized 1a/1b isomers.

FIGS. 8A-8B 215 nm absorbance (FIG. 8A) and EIC LC-MS (FIG. 8B) traces of Diels-Alder cyclization of compound 3 following 16 hr. incubation on resin in DMF (bottom trace) or in aqueous solution (top trace) after cleavage (10% ACN/H$_2$O, 0.1% TFA).

FIG. 10B In vitro trypsin and chymotrypsin resistance assays for 1a versus linear analog 1 wt, and 4a and linear analog 4 wt, respectively. FIG. 10C Cell migration model scratch wound assay comparing reduction in wound closure by RGD peptides 1 wt and 1a at 10 and 20 µM relative to DMSO control. Data represent mean±s.d. distance measurements from images of two biological replicates, five distance measurements each. n. s.=not significant; *=P<0.05; **=P<0.0005; Student's t-test.

FIG. 11 Compound list and data for turn and loop motif DAC peptides and their precursors.

FIGS. 12A-12B FIG. 12A $^1$H-NMR spectra of 4 wt, 4 hex, and 4a in the vinylic (~6-5 p.p.m.) region. FIG. 12B Model of 4a cycloadduct depicting through-bond and through-space interactions between cycloadduct protons as determined by TOCSY and NOESY.

FIG. 13B Peptide backbone alignment over 50 ns simulations for 4 wt and 4a. FIG. 13C RMSD values for 4 wt and 4a peptide backbones and all atoms (excluding hydrogens).

FIG. 14B 280 nm absorbance HPLC trace and resulting aqueous solution reaction time course of conversion of 5 to cyclized isomers 5a-c.

FIGS. 15A-15B FIG. 15A 280 nm absorbance LC-MS traces of incubation of DAC-p53 peptide 5 mixture with βME in aqueous buffer, verifying Michael adduction of linear precursor 5 and stability of cyclized isomers. FIG. 15B CD spectra of linear analog 5 wt and 5a-c.

FIGS. 17A-17D FIG. 17A Sequence of SRC2 wildtype peptide used as scaffold with conserved LXXLL motif; staple placement and structures of DAC-SRC2 peptides 6a-b and 7a and double-stapled 8a. FIG. 17B 215 nm absorbance HPLC traces of pre-cursor peptide used and resulting cyclized product profile of compound 7 following 4 hr. on resin heating in DMSO. FIG. 17C CD spectra of isolated DAC-SRC2 peptides compared to unmodified wildtype sequence. FIG. 17D Synthetic scheme for layering ring-closing metathesis and Diels-Alder cyclization for the synthesis of double-stapled SRC2 peptide 8a.

FIGS. 18A-18C FIG. 18A 215 nm absorbance HPLC traces of pre-cursor peptide 8 pre, ring-closing metathesis product 8 rcm, Diels-Alder functionalized peptide 8 and fully-DAC-SRC2 double-stapled peptide 8a. FIG. 18A CD spectra of helical compound 8a. FIG. 18C Normalized FP assay results showing a dose range of DAC-SRC2 peptides effectively competing off fluorescein-labeled wildtype SRC peptide from wildtype ERα. Each data point represents measurements from two independent experiments run in triplicate, ±s.e.m. Dose-response curves fit with a four parameter log(inhibitor) vs response equation in Prism 5 graphing software.

FIG. 19 Compound list and data for helix motif DAC peptides, their precursors, and related analogs.

FIG. 20 Representative 1H-NMR spectra of the vinylic region of double stapled RCM stabilized and DAC peptide 8a.

FIG. 21B Two views of the structure of the DAC-SRC2 pep-tide 6a cycloadduct with endo stereochemistry overlaid with electron density map (grid) from resolved crystallographic data (2mFo-DFc map contoured to 1a). FIG. 21C Dorsal (top) and axial (bottom) view of 6a bound in the AF2 binding pocket. Relevant residues numbered according to SRC2 sequence are highlighted, as well as the Diels-Alder cyclization moiety in yellow. Flexible portions of the structure with low electron density are omitted.

FIG. 22B Interactions between the endo Diels-Alder cycloadduct and hydrophobic shelf residues in ERα adjacent to AF2 cleft. FIG. 22C Helix capping hydrogen bonds formed between E542 in ERα represents the N-terminal charge claim, coupled with the peptide intramolecular hydrogen bond that caps the C-terminus.

FIGS. 23A and 23B Representative amino acid side chains for DAC-ANP peptide. X=C, O, S, NH, and Y=0, 1, 2, 3, 4, (or other branched/cyclic alkyl fragments).

FIG. 24 A synthetic scheme for synthesis of DAC-ANP-1.

FIG. 25 Comparison of the reduced and oxidized forms of DAC-ANP-1. DAC-ANP-1 (reduced): major observed ion: 1217.8; cyclized on-resin (DMSO, 45° C., 2 hr), HPLC purified. DAC-ANP-1 (oxidized): major observed ion: 1216.9; oxidized in solution (0.1 M ammonium acetate, 5% DMSO, pH 7.6, room temperature).

FIGS. 26A-26C FIG. 26A HPLC plots of DAC-ANP-1. FIG. 26B Extracted ion chromatogram of DAC-ANP-1 (24 hr ox is fully oxidized). FIG. 26C Major product mass spectra of reduced and oxidized DAC-ANP-1.

FIG. 27 Comparison of the reduced and oxidized forms of ANP-WT. ANP-WT (reduced): major observed ion: 1102.9; ANP-WT (oxidized) major observed ion: 1101.4.

FIG. 28B Extracted ion chromatogram of ANP-WT (24 hr ox is 60% oxidized). FIG. 28C Major product mass spectra of reduced and oxidized ANP-WT.

FIG. 32 RTD8 structures.

FIG. 33B Extracted ion chromatogram of Max-WT-cpd. FIG. 33C Major product mass spectra of Max-WT-cpd. FIG. 33D HPLC plots of RTD8-cpd. FIG. 33E Extracted ion chromatogram of RTD8-cpd. FIG. 33F Major product mass spectra of RTD8-cpd.

FIG. 34 Synthetic scheme of a Diels-Alder reaction between cyclopentadiene and ring-closing metathesis staple.

FIG. 37 TAG sites within RAB25.

DETAILED DESCRIPTION

Figure 1:
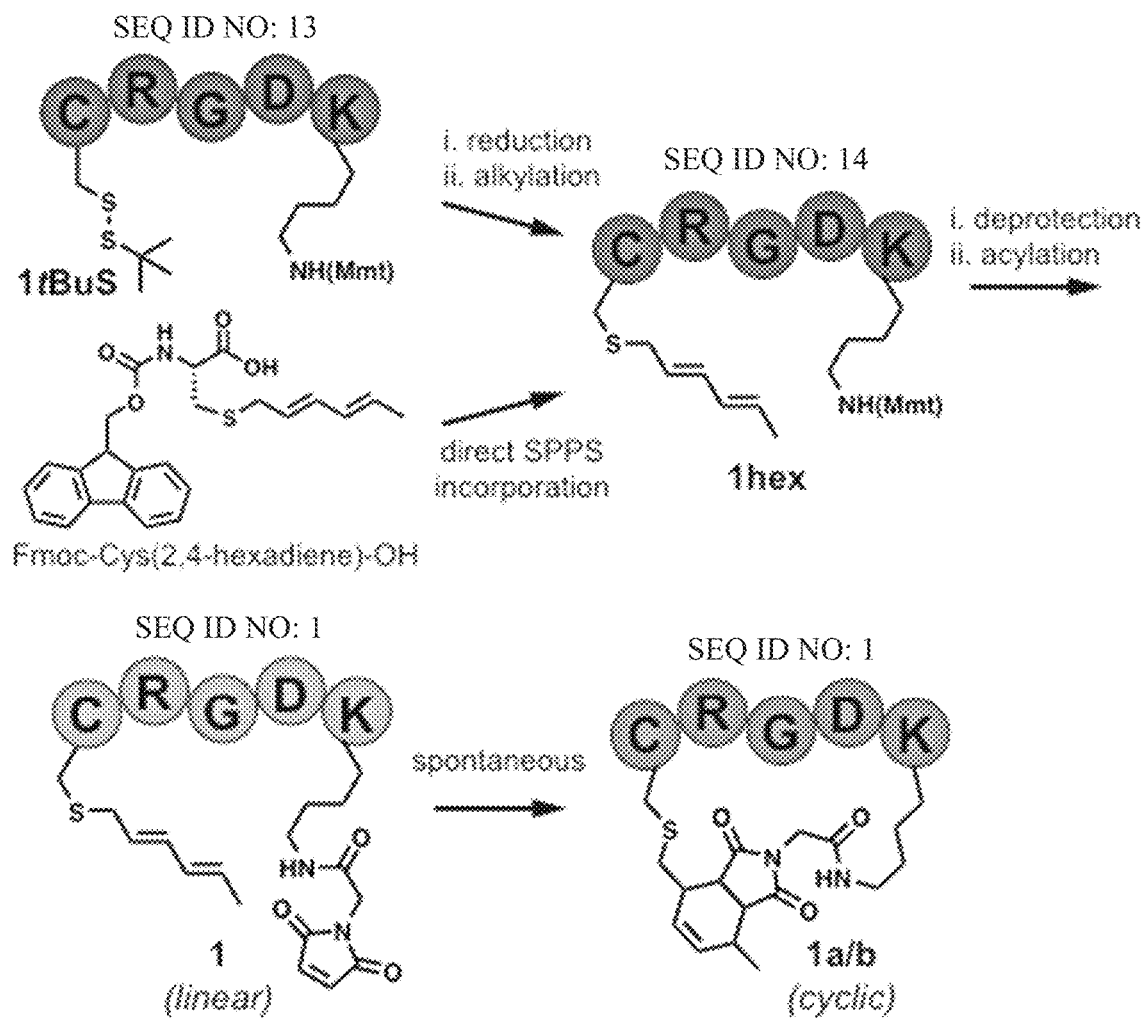
FIG. 1 Schematic of a Diels-Alder cyclized (DAC) peptide functionalization.

As used herein, a "protein" or "polypeptide" refers to a molecule comprising at least four amino acid residues. As used herein, the term "wild-type" refers to the endogenous version of a molecule that occurs naturally in an organism. In some embodiments, wild-type versions of a protein or polypeptide are employed, however, in many embodiments of the disclosure, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

Where a protein is specifically mentioned herein, it is in general a reference to a native (wild-type) or recombinant (modified) protein or, optionally, a protein in which any signal sequence has been removed. The protein may be isolated directly from the organism of which it is native, produced by recombinant DNA/exogenous expression methods, or produced by solid-phase peptide synthesis (SPPS) or other in vitro methods. In particular embodiments, there are isolated nucleic acid segments and recombinant vectors incorporating nucleic acid sequences that encode a polypeptide (e.g., an antibody or fragment thereof). The term "recombinant" may be used in conjunction with a polypeptide or the name of a specific polypeptide, and this generally refers to a polypeptide produced from a nucleic acid molecule that has been manipulated in vitro or that is a replication product of such a molecule.

An amino acid is a type of organic acid that contains a carboxyl functional group (—COOH), an amine functional group (—NH$_2$), a side chain, and a hydrogen atom, all bound to a central carbon atom. A natural amino acid is one of the twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. As used herein a non-natural amino acid refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. As used herein, an amino acid derivative refers to an amino acid that has been functionalized such that the amino acid derivative structure is different from a precursor amino acid structure.

Macrocyclization can improve bioactive peptide ligands through preorganization of molecular topology, leading to improvement of pharmacologic properties like binding affinity, cell permeability and metabolic stability. Diels-Alder [4+2] cycloadditions, for example, can be harnessed for peptide macrocyclization and stabilization within a range of peptide scaffolds and chemical environments. Diels-Alder cyclization of diverse diene-dienophile reactive pairs proceeds rapidly, in high yield and with tunable stereochemical preferences on solid-phase or in aqueous solution. This reaction can be applied alone or in concert with other stabilization chemistries, such as ring-closing olefin metathesis, to stabilize loop, turn, and α-helical secondary structural motifs.

NMR and molecular dynamics studies of model loop peptides confirmed preferential formation of endo cycloadduct stereochemistry, imparting significant structural rigidity to the peptide backbone that resulted in augmented protease resistance and increased biological activity of a Diels-Alder cyclized (DAC) RGD peptide. This reaction can further promote the stabilization of DAC α-helical peptides derived from the ERα-binding protein SRC2. A 2.25 Å co-crystal structure of one DAC helical peptide bound to ERα, unequivocally corroborated endo stereochemistry of the resulting Diels-Alder adduct, and confirmed that the unique architecture of stabilizing motifs formed with this chemistry can directly contribute to target binding. These data establish Diels-Alder cyclization as a versatile approach to stabilize diverse protein structural motifs under a range of chemical environments.

The following includes certain aspects of the invention.

1. A macrocyclic compound of the formula:

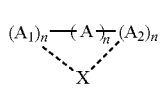
(I)

wherein A, $A_1$, and $A_2$ are amino acids; each n is independently an integer from 0 to 600 (except where attached to X, where n is at least 1); and X is an adduct between reactive functional groups.

2. The macrocyclic compound of aspect 1, wherein X is bound to a side chain, amine group, carboxy group, or α-carbon of one amino acid and to a side chain, amine group, carboxy group, or α-carbon of a different amino acid.

3. The macrocyclic compound of aspect 1 or 2, wherein the adduct is an adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s).

4. The macrocyclic compound of any one of aspects 1 to 3, wherein one of $A_1$ and $A_2$ is cysteine or a cysteine derivative and the other is lysine or a lysine derivative.

5. The macrocyclic compound of any one of aspects 1 to 4, wherein X is formed from a reaction between a hexadiene group and a maleimide group, a maleimide group and a furan group, a cyclopentadiene group and another cyclopentadiene group, a cyclopentadiene group and a maleimide group, or a cyclopentadiene group and an aliphatic olefin.

6. The macrocyclic compound of any one of aspects 1 to 5, wherein X is one of

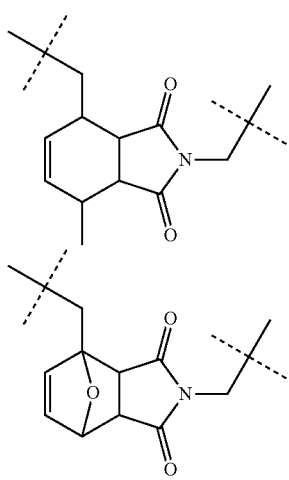

-continued

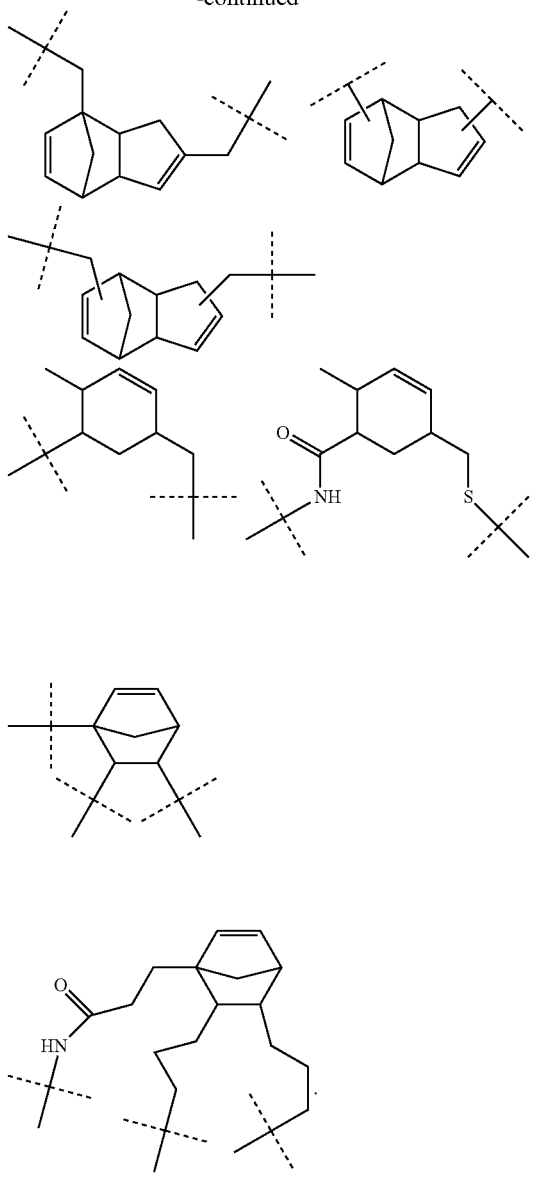

7. The macrocyclic compound of any one of aspects 1 to 6, wherein the compound of formula (I) is further defined as

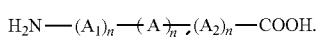

8. The macrocyclic compound of any one of aspects 1 to 6, wherein the compound of formula (I) is further defined as

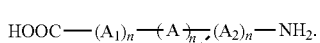

9. The macrocyclic compound of any one of aspects 1-8, wherein at least one amino acid A is a non-natural amino acid or an amino acid derivative.

10. The macrocyclic compound of any one of aspects 1-9, wherein the compound of formula (I) is further defined as one of

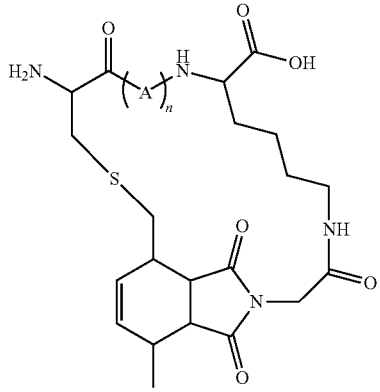

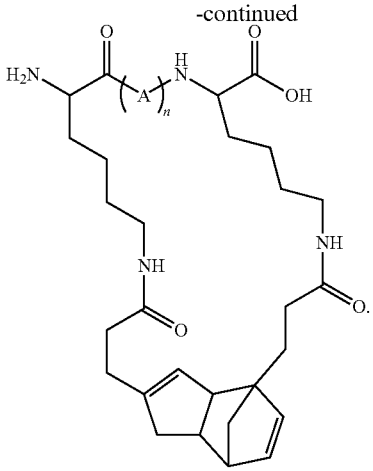

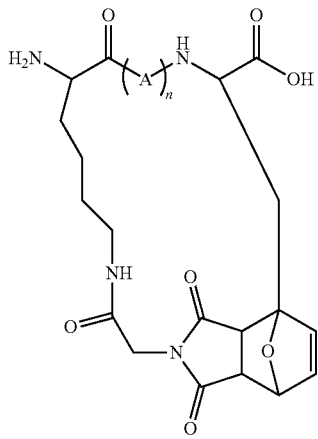

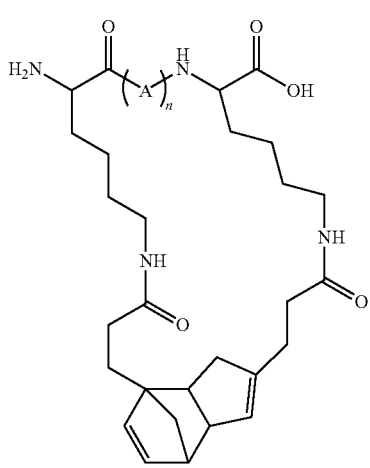

11. The macrocyclic compound of any one of aspects 1-10, wherein X is an adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s), and the adduct is formed between reactive functional groups bound to any two different amino acids in the compound.

12. A method of synthesizing a macrocyclic compound, the method comprising:
synthesizing a peptide of formula (II) comprising reactive functional groups Y and Z capable of undergoing a Y—Z conjugating reaction; and
subjecting the peptide to conditions that drive the Y—Z conjugating reaction to form an intramolecular Y—Z crosslinking moiety;

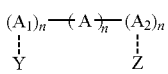
(II)

wherein A, $A_1$, and $A_2$ are amino acids; and each n is independently an integer from 0 to 600 (except where attached to Y or Z, where n is at least 1).

13. The method of aspect 12, wherein each of Y and Z is independently bound to a side chain, amine group, carboxy group, or α-carbon of a different amino acid.

14. The method of aspect 12 or 13, wherein the Y—Z conjugating reaction is a cyclo addition reaction.

15. The method of aspect 12 or 13, wherein the Y—Z conjugating reaction is selected from the group consisting of a Diels-Alder reaction, an olefin metathesis reaction, a copper-catalyzed azide-alkyne click reaction, cystine formation via oxidation of two cysteine residues, crosslink formation via alkylation of one or more cysteine residues, a thiol-ene reaction, or a lactam bridge formation between N- or C-termini and/or residue side chain(s).

16. The method of any one of aspects 12-15 wherein at least one amino acid A is a non-natural amino acid or an amino acid derivative.

17. The method of any one of aspects 12-16, wherein one of $A_1$ and $A_2$ is cysteine or a cysteine derivative and the other is lysine or a lysine derivative.

18. The method of any one of aspects 12-17, wherein Y is a conjugated diene.

19. The method of aspect 18, wherein the conjugated diene is part of a linear or cyclic structure.

20. The method of aspect 18, wherein the conjugated diene is 2,4-hexadiene, furan, thiophene, cyclopentadiene, or a derivative thereof.

21. The method of any one of aspects 18 to 20, wherein the conjugated diene or derivative thereof includes an electron-donating group moiety.

22. The method of aspect 21, wherein the electron-donating group is selected from the group consisting of alkyl, ester, amide, alkyloxy, hydroxyl, amine, and silyl ether.

23. The method of any one of aspects 12 to 22, wherein Z is a dienophile.

24. The method of aspect 23, wherein the dienophile is maleic anhydride or a derivative thereof, benzyne or a derivative thereof, quinone or a derivative thereof, an N-sulfinyl derivative, a sulfur-diimide derivative, an imino derivative, a nitroso derivative, a thionitroso derivative, acrylate or a derivative thereof, or crotonate or a derivative thereof.

25. The method of aspect 23 or 24, wherein the dienophile includes an electron-withdrawing group moiety.

26. The method of aspect 25, wherein the electron-withdrawing group is selected from the group consisting of ester, amide, nitro, sulfone, carbonyl, cyano, and haloalkane moieties.

27. The method of any one of aspects 12 to 26, wherein reactive functional groups Y and Z are each independently bound to a side chain, amine group, carboxy group, or α-carbon of a different amino acid.

28. The method of any one of aspects 14-27, wherein the peptide of formula (II) is further defined as one of

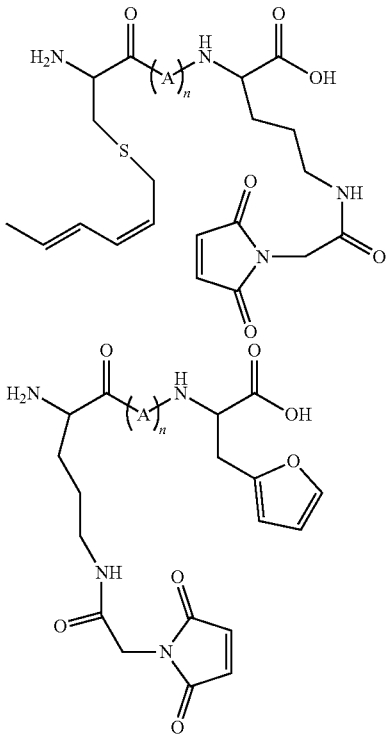

-continued

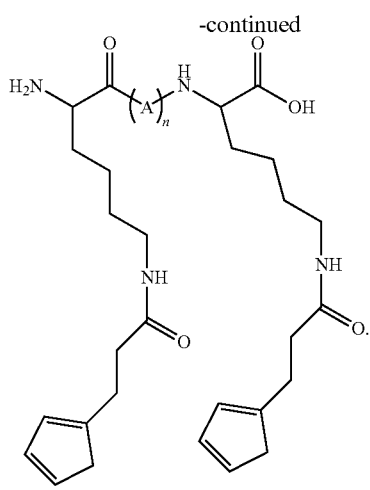

29. A bicyclic or higher-order cyclic compound of the formula:

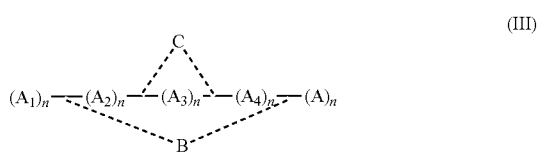

(III)

wherein A, $A_1$, $A_2$, $A_3$, and $A_4$ are amino acids; each n is independently an integer from 1 to 600; B is an adduct between complementarily-reactive functional groups bound to any two amino acids; C is an adduct between complementarily-reactive functional groups bound to any two amino acids not bound to B.

30. The bicyclic or higher-order cyclic compound of aspect 29, wherein the reactive functional groups used to form the B adduct and reactive functional groups used to form the C adduct are orthogonal to each other.

31. The bicyclic or higher-order cyclic compound of aspect 29 or 30, wherein one of adducts B or C is an adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s).

32. The bicyclic or higher-order cyclic compound of aspect 31, wherein the other of adducts B or C is an adduct resulting from a Diels-Alder reaction, an olefin metathesis reaction, copper-catalyzed azide-alkyne click chemistry, cystine formation via oxidation of two cysteine residues, crosslink formation via alkylation of one or more cysteine residues, thiol-ene chemistry, or a lactam bridge formation between N- or C-termini and/or residue side chain(s).

33. The bicyclic or higher-order cyclic compound of any one of aspects 29 to 32, wherein the reactive functional groups used to form the C adduct are bound to amino acids that are internal to the two amino acids bound to the reactive functional groups used to form the B adduct.

34. The bicyclic or higher-order cyclic compound of any one of aspects 29 to 32, wherein the reactive functional groups used to form the B adduct are bound to amino acids that are internal to the two amino acids bound to the reactive functional groups used to form the C adduct.

35. The bicyclic or higher-order cyclic compound of any one of aspects 29 to 32, wherein the reactive functional groups used to form the B adduct are bound to amino acids that are in a staggered relationship with the amino acids bound to the reactive functional groups used to form the C adduct.

36. The bicyclic or higher-order cyclic compound of any one of aspects 29-35, wherein at least one amino acid is a non-natural amino acid or an amino acid derivative.

37. A method of synthesizing a bicyclic or higher-order cyclic compound, the method comprising:
synthesizing a peptide of formula (VI) comprising: i) reactive moieties D and E capable of undergoing a D-E conjugating reaction and ii) reactive moieties F and G capable of undergoing an F-G conjugating reaction;
subjecting the peptide to conditions that drive the D-E conjugating reaction to form an intramolecular D-E crosslinking moiety;
subjecting the peptide to conditions that drive the F-G conjugating reaction to form an intramolecular F-G crosslinking moiety;

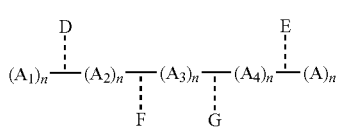

(VI)

wherein A, $A_1$, $A_2$, $A_3$, and $A_4$ are amino acids; and each n is independently an integer from 1 to 600.

38. The method of aspect 37, wherein reactive functional groups D, E, F, and G are each independently bound to a different amino acid side chain, amino acid amino group, amino acid carboxy group, or amino acid α-carbon of any amino acid $A_1$ to $A_n$.

39. The method of aspect 37 or 38, wherein at least one of reactive functional groups D, E, F, and G is bound to a non-natural amino acid or an amino acid derivative.

40. The method of aspect 37 or 38, wherein each of reactive functional groups D, E, F, and G is bound to a non-natural amino acid or an amino acid derivative.

41. The method of any one of aspects 37 to 40, wherein reactive functional group F and complementarily-reactive functional group G are bound to amino acids that are internal of reactive amino acids bound to functional group D and complementarily-reactive functional group E.

42. The method of any one of aspects 37 to 40, wherein reactive functional group D and complementarily-reactive functional group E are bound to amino acids that are internal of reactive amino acids bound to functional group F and complementarily-reactive functional group G.

43. The method of any of aspect 37 to 40, wherein the amino acid bound to reactive functional group E and the amino acid bound to reactive functional group F are internal of the amino acid bound to reactive functional group D and the amino acid bound to reactive functional group G.

44. The method of any one of aspects 37 to 40, wherein the amino acid bound to reactive functional group D and the amino acid bound to reactive functional group G are internal of the amino acid bound to reactive functional group F and the amino acid bound to reactive functional group E.

45. The method of any one of aspects 37 to 44, wherein the D-E conjugating reaction is selected from the group consisting of a Diels-Alder reaction, a ring-closing metathesis reaction, a copper-catalyzed azide-alkyne click reaction, cystine formation via oxidation of two cysteine residues, crosslink formation via alkylation of one or more cysteine residues, a thiol-ene reaction, or a lactam bridge formation between N- or C-termini and/or residue side chain(s).

46. The method of any one of aspects 37 to 44, wherein the F-G conjugating reaction is selected from the group consisting of a Diels-Alder reaction, a ring-closing metathesis reaction, a copper-catalyzed azide-alkyne click reaction, cystine formation via oxidation of two cysteine residues, crosslink formation via alkylation of one or more cysteine residues, a thiol-ene reaction, or a lactam bridge formation between N- or C-termini and/or residue side chain(s).

47. The method of any one of aspects 37 to 46, wherein the D-E conjugating reaction and the F-G conjugating reaction are different reaction types.

48. A polypeptide of the formula (X):

$$(A_1)_n\text{-}R^1\text{-}(A_2)_m \quad\quad (X)$$

wherein $A_1$ and $A_2$ are amino acids; n and m are each independently integers from 2 to 600; the amino acids of $A_1$ are N- to C-terminus, and the amino acids of $A_2$ are C- to N-terminus; and $R^1$ is an adduct formed from a reaction between a cyclopentadiene group and another cyclopentadiene group.

49. The polypeptide of aspect 48, wherein $R^1$ is

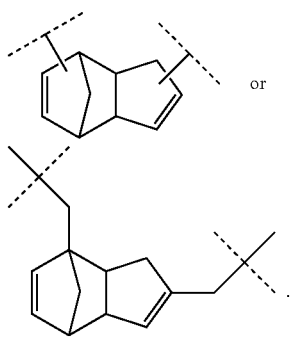 or

50. The polypeptide of aspect 48 or 49, wherein the polypeptide of formula (X) is further defined as $(A_1)_{n-1}$-Lys-$R^1$-Lys-$(A_2)_{m-1}$.

51. A method of ligating a peptide or polypeptide, the method comprising reacting a first peptide or polypeptide to a second peptide or polypeptide, wherein the first peptide or polypeptide and the second peptide or polypeptide each comprise a cyclopentadiene group, and wherein upon reaction an adduct is formed between the cyclopentadiene group of the first peptide or polypeptide and the cyclopentadiene group of the second peptide or polypeptide.

52. The method of aspect 51, wherein the adduct is

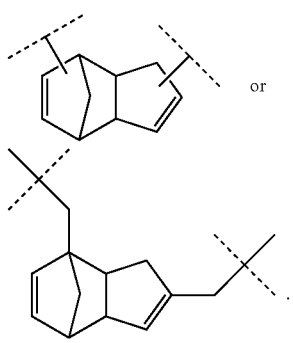 or

53. The method of aspect 51 or 52, wherein the first and second peptide or polypeptide is the same and is homodimerized.

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLE 1

A. Diels-Alder Cyclized Peptides

Figure 2:
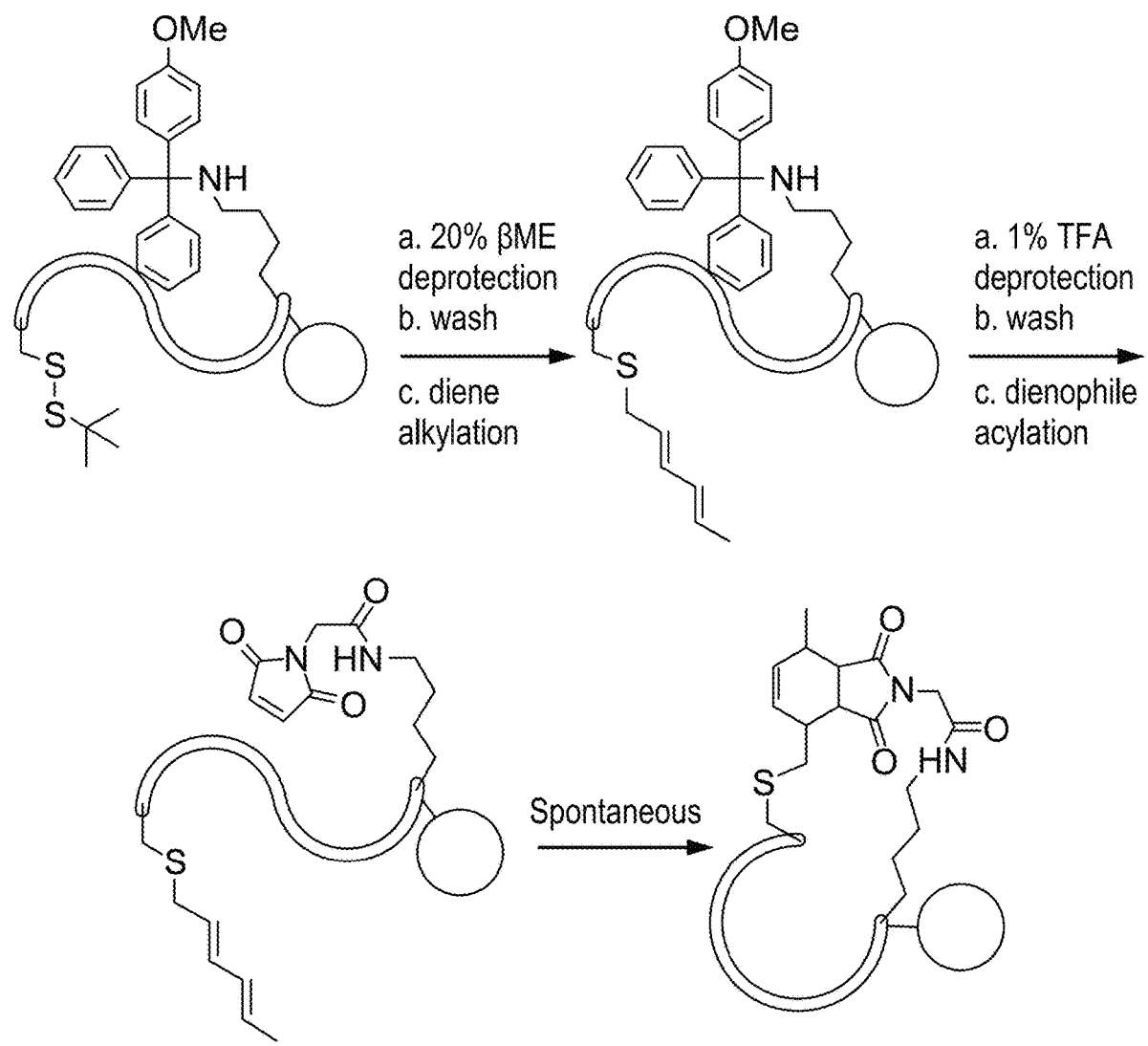
FIG. 2 Synthetic scheme for on-resin synthesis of DAC peptides.
Figure 5:
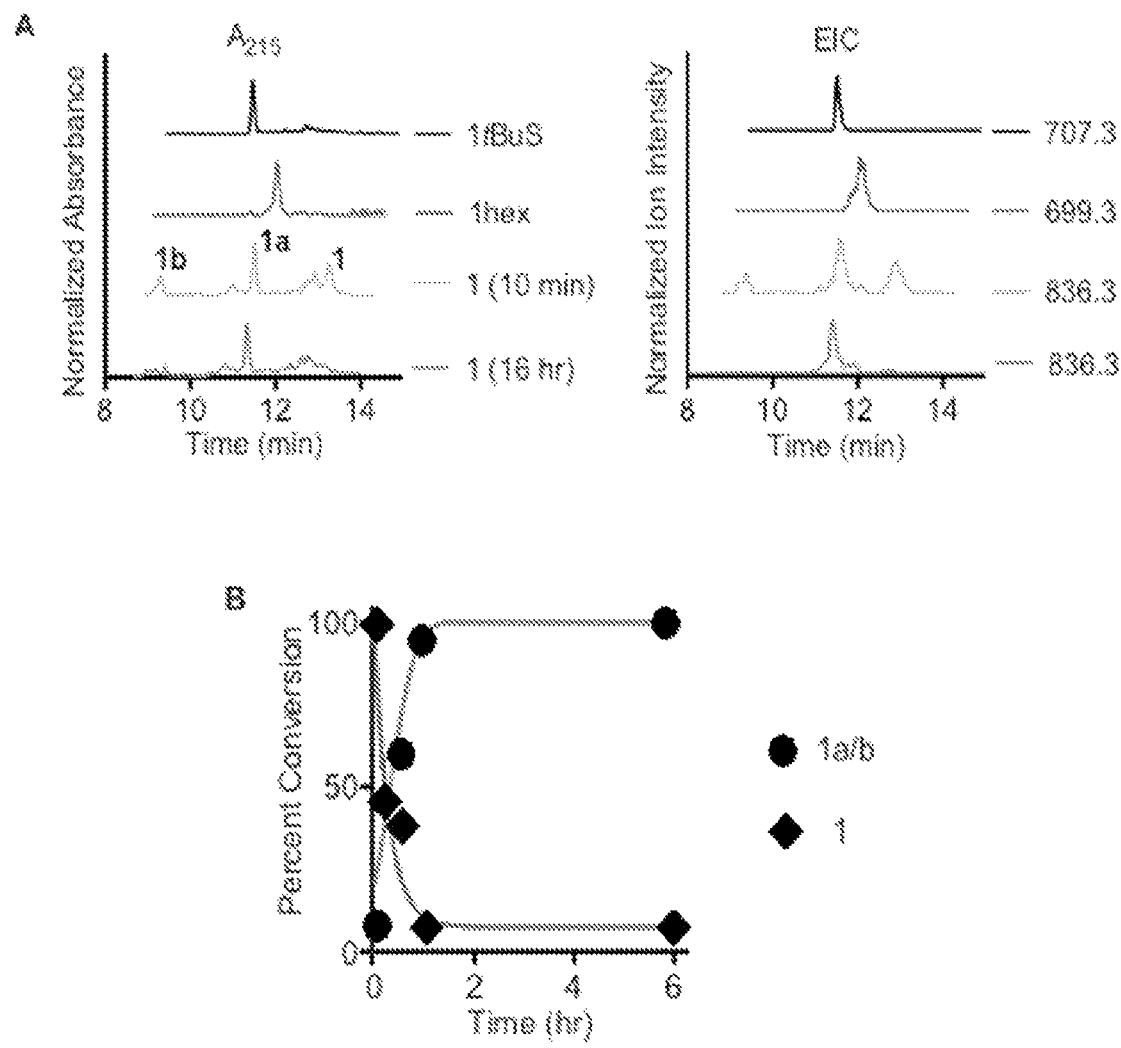
FIGS. 5A-5B FIG. 5A Absorbance (215 nm) and extracted ion chromatogram (EIC) LC-MS traces of crude peptide following the indicated functionalization and reaction times with the RGD compound 1 scaffold.
Figure 6:
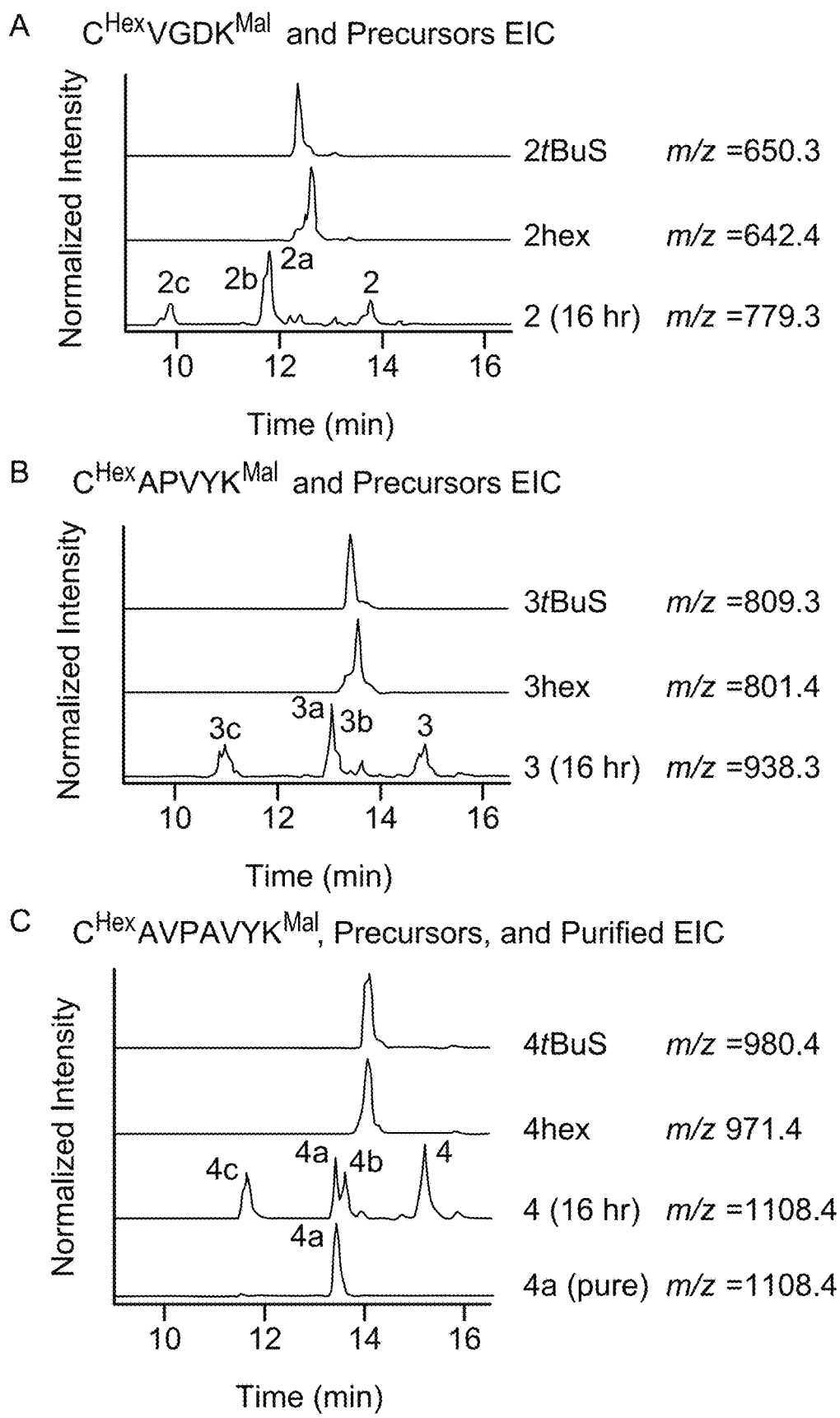
FIGS. 6A-6C EIC LC-MS traces of crude 2, 3, and 4 precursor peptides (top trace in each graph), hexadiene-alkylated intermediates (second trace from top in each graph), maleimido-functionalized peptides (third trace from top in each graph) following acylation and purified endo stereoisomer 4a (bottom trace of FIG. 6C). Each compound number represents the non-cyclized (X) and cyclized isomers (Xa, Xb . . . ) with lettering reported in order of relative intensity of cyclic products as determined by separation on LC-MS.

A series of Diels-Alder cyclized (DAC) peptides with turn and loop motifs were synthesized, including an anti-migratory RGD peptide, analogs of which are undergoing clinical testing in oncology. Model peptides of various length and sequence were synthesized containing orthogonally-protected cysteine (tBuS-) and lysine (Mmt-) side chains, with the former invariably in the i-position, and the latter in the i+4, i+5, and i+7 positions. Sequential on-resin cysteine deprotection and hexadiene alkylation with 1-bromo-2,4-hexadiene proceeded quantitatively (FIGS. 1, 2, 5A). The corresponding diene-containing amino acid, Fmoc-Cys(2,4-hexadiene)-OH, which is compatible with direct incorporation by SPPS (FIGS. 1, 3), was also synthesized. Subsequent on-resin lysine deprotection and acylation with N-maleimido-glycine on an RGD model peptide resulted in formation of two distinct peaks on LC-MS (1 and 1a) with the same mass and ~1 minute retention time shift, suggesting formation of a cyclized product eluting earlier on the C18 column (FIGS. 1, 5A). This product appeared rapidly, with an approximate 2:1 ratio of 1a to 1 within 5 minutes of dienophile introduction; near-complete conversion to 1a was observed upon extended incubation on resin (16 hr, FIG. 5A). Kinetic reaction monitoring confirmed rapid conversion of later-eluting 1 to 1a, as well as minor product 1b, with nearly 95% formation within 1 hour (FIG. 5B). This pattern was observed across diverse intervening sequences and diene-dienophile spacing (Table 1, FIG. 11), with high yields of ~85-95% conversion to earlier-eluting, presumably cyclized species. In each scaffold studied, additional earlier-eluting minor isomeric species (≤10% relative to major product) were observed ~4 minutes before the linear peptide (FIGS. 5B, 6).

TABLE 1

Diels-Alder cyclized loop peptides and precursors

| Sequence | SEQ ID NO | Compound(s) | Conversion % | Product Ratio* |
|---|---|---|---|---|
| $C_{Hex}RGDK_{Mal}$ | 1 | 1, 1a, 1b | 95 | >50:1 |
| $C_{Hex}VGDK_{Mal}$ | 2 | 2, 2a, 2b, 2c | 92 | 9:1 |
| $C_{Hex}APVYK_{Mal}$ | 3 | 3, 3a, 3b, 3c | 89 | 8:1 |
| $C_{Hex}AVPAVYK_{Mal}$ | 4 | 4, 4a, b, 4c | 85 | 9:1 |

*Ratios reported as major:minor product(s) were quantified by integrated LC-MS peak area. Percent conversion (% conv.) refers to the percent yield from non-cyclized to cyclized products.

Figure 7:
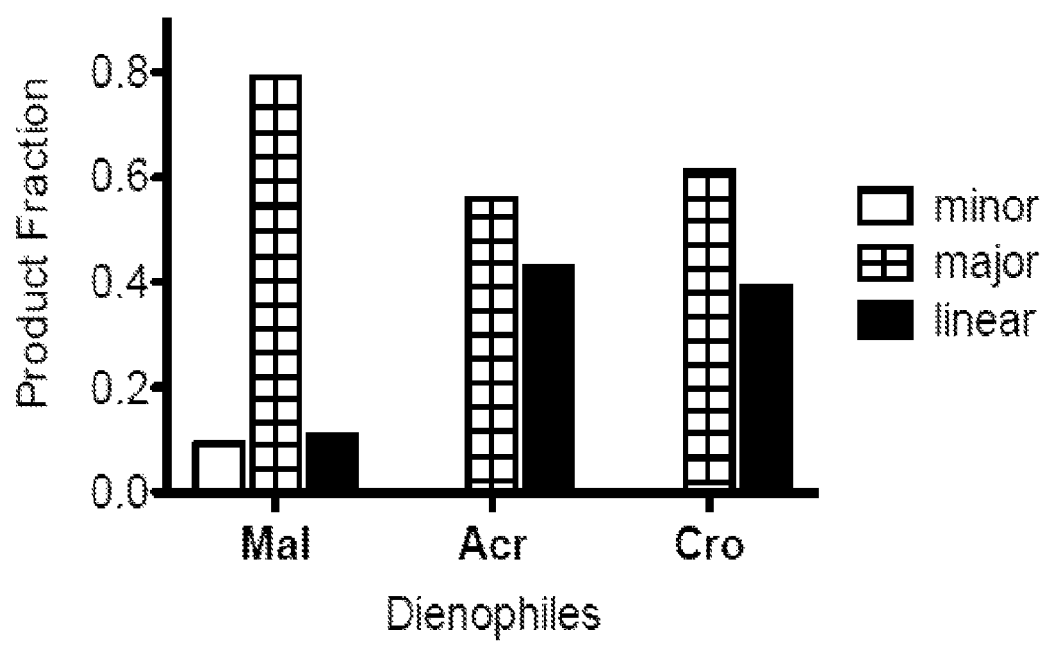
FIG. 7 Quantification of crude product profiles following on-resin lysine acylation of 3 hex with either maleimido-glycine (Mal), acrylic acid (Acr) or crotonic acid (Cro) and overnight incubation.
Figure 8:
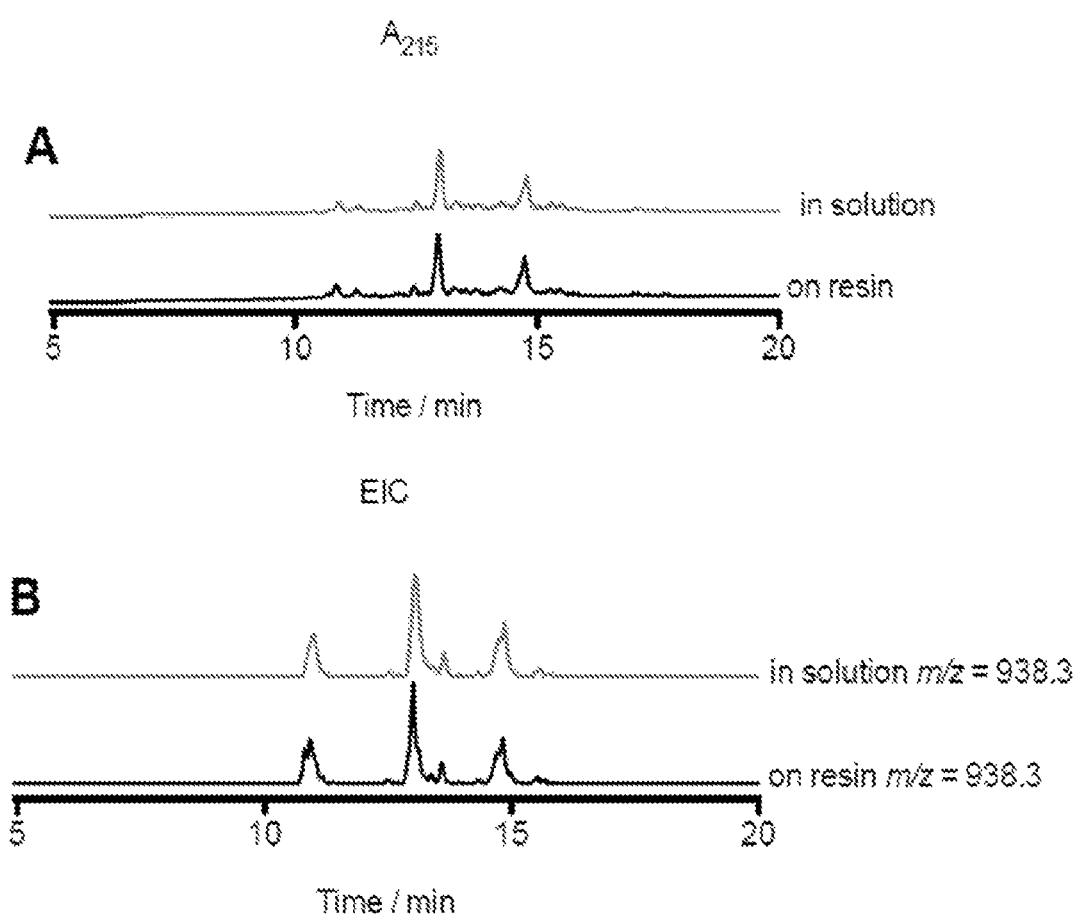

A limited screen of reaction conditions revealed that mild heating on resin in DMSO effected cyclic conversion, but also resulted in increased ratio of major to minor isomeric products (Table 2), which may be due to de-aggregation of the protected peptide on resin. Other less reactive dienophiles such as acryloyl and crotonyl groups were found to react with hexadiene in yields comparable to maleimide (FIG. 7). These viable alternative dienophiles are also compatible with direct incorporation during SPPS and offer increased diversity of cyclic structures. Similar reaction profiles were observed for peptides produced by on-resin diene incorporation or direct use of Fmoc-Cys(2,4-hexadiene)-OH, as well as upon incubation in aqueous solution following peptide cleavage (FIG. 8). These data confirm the compatibility of Diels-Alder peptide cyclization in diverse organic and aqueous chemical environments.

TABLE 2

Results from screen of on-resin cyclization conditions for compound 1

| Solvent | Temp. (° C.) | Conversion %* | Major:Minor |
|---|---|---|---|
| Control | n/a | 77.4 | 12.3 |
| $H_2O$ | 25 | 81.9 | 11.8 |
| DMF | 25 | 85.3 | 9.9 |
| $H_2O$ | 45 | 89 | 15.2 |
| DMF | 45 | 88.2 | 23.5 |
| DMSO | 45 | 92.2 | 50.2 |

*Reactions were carried out for 2 hours followed by standard cleavage from resin. Increased conversion and major product enrichment is seen for many compounds with extended heating.

Figure 9:
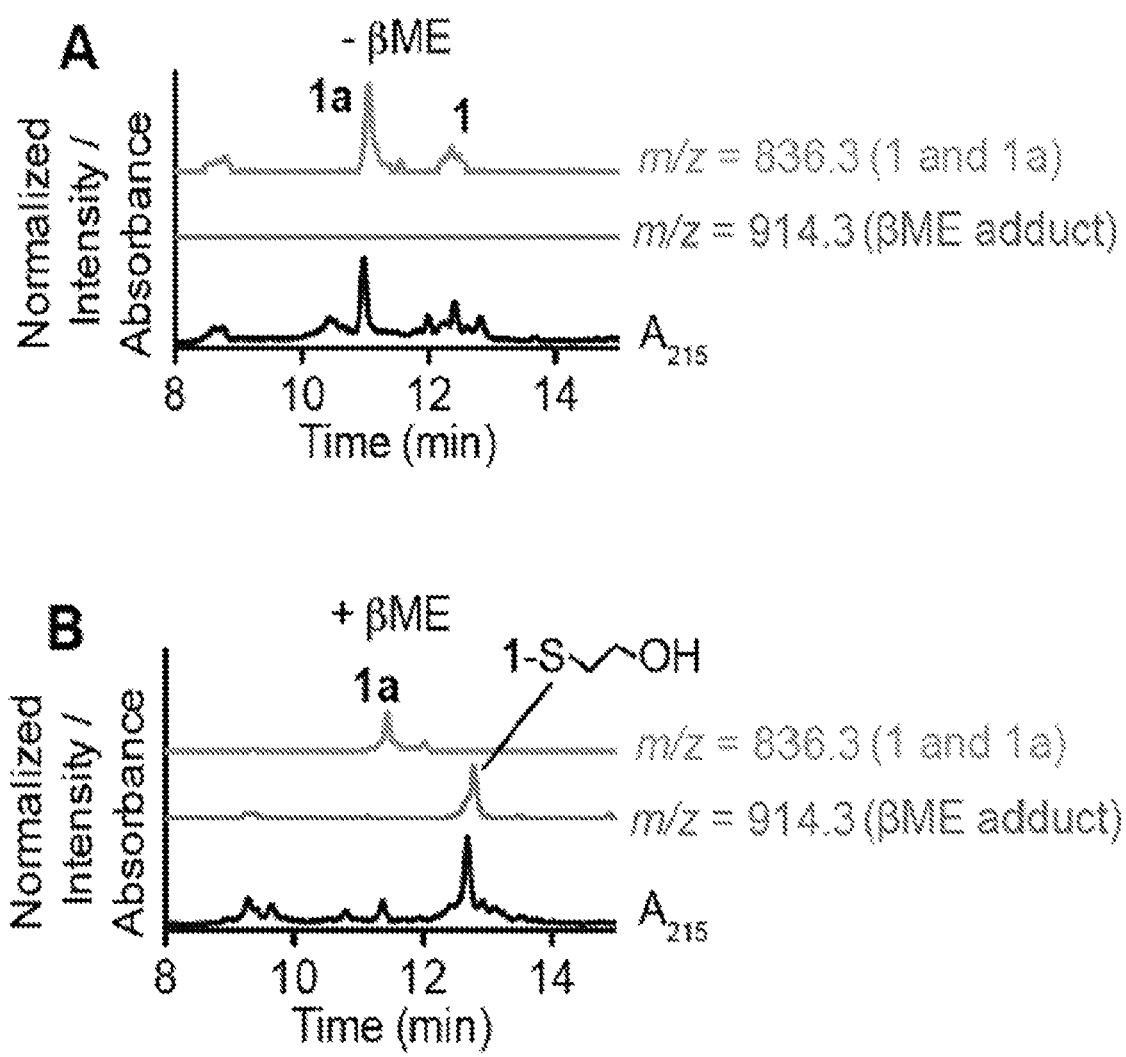
FIGS. 9A-9B EIC and 215 nm absorbance LC-MS traces of crude 1 and 1a/1b with (FIG. 9A) or without (FIG. 9B) βME treatment, showing conversion of 1 to the corresponding βME-trapped species (m/z=914.3).
Figure 10:
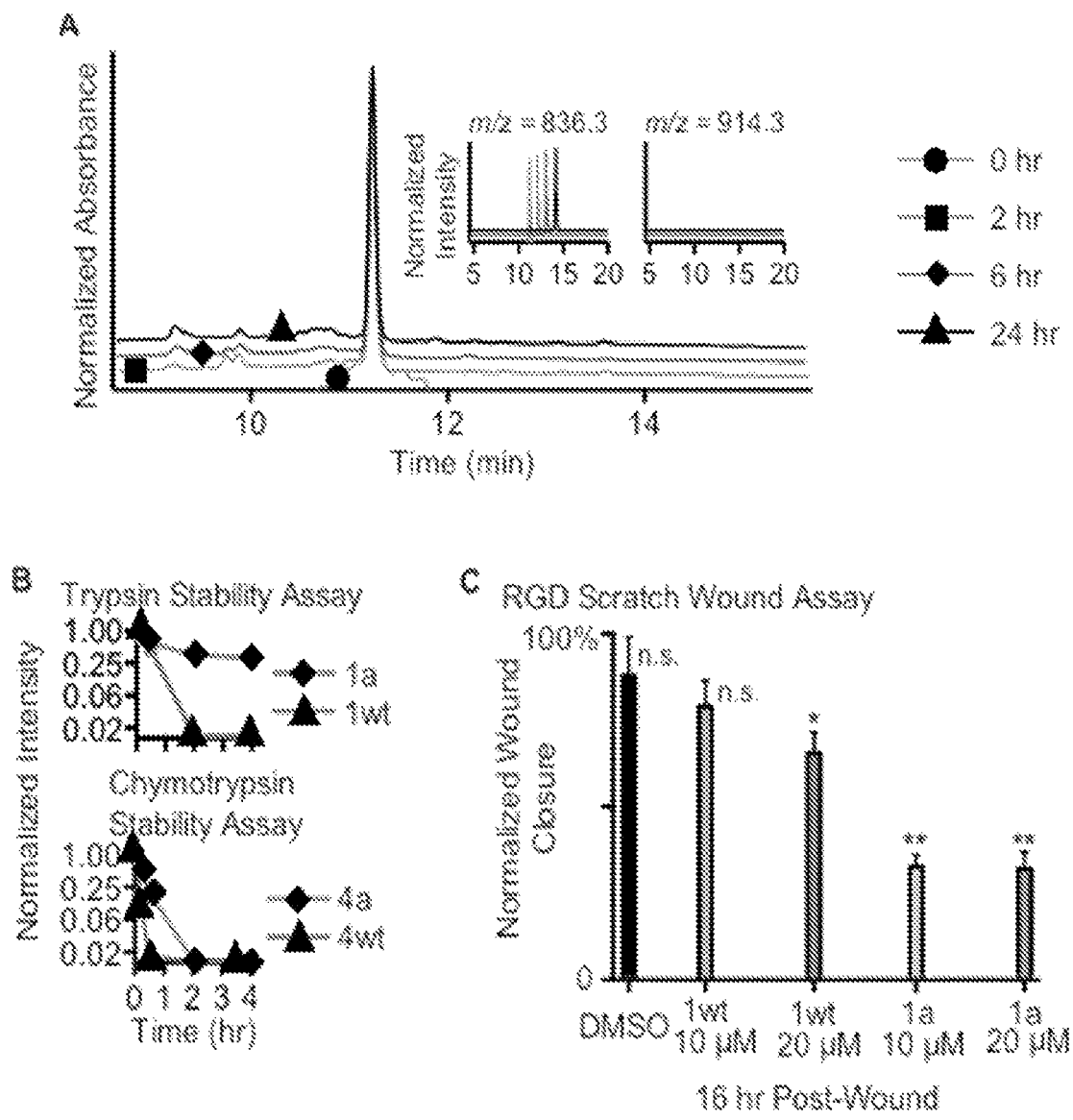
FIGS. 10A-10C FIG. 10A Extended time course tracking of HPLC-purified 1a incubated with βME in aqueous buffer, verifying cycloadduct stability (βME-trapped species m/z=914.3).

B. Diels-Alder Cycloadditions Form Chemically Stable Peptide Macrocycles with Enhanced Protease Resistance and Biological Activity Experiments were performed to verify that 1 and 1a represented non-cyclized and cyclized products. On-resin incubation of the 1 and 1a crude mixture with excess 2-mercaptoethanol (βME), which should only react with linear maleimide-containing peptide, resulted in complete consumption of 1, yielding a species with the mass of the βME conjugate addition product (FIG. 9). By contrast, 1a levels remained constant, consistent with the loss of the α,β-unsaturated electrophile after Diels-Alder cyclization. Likewise, prolonged exposure of purified 1a to βME did not result in any addition product, suggesting formation of a stable DAC-RGD peptide macrocycle (FIG. 10A).

Figure 4:
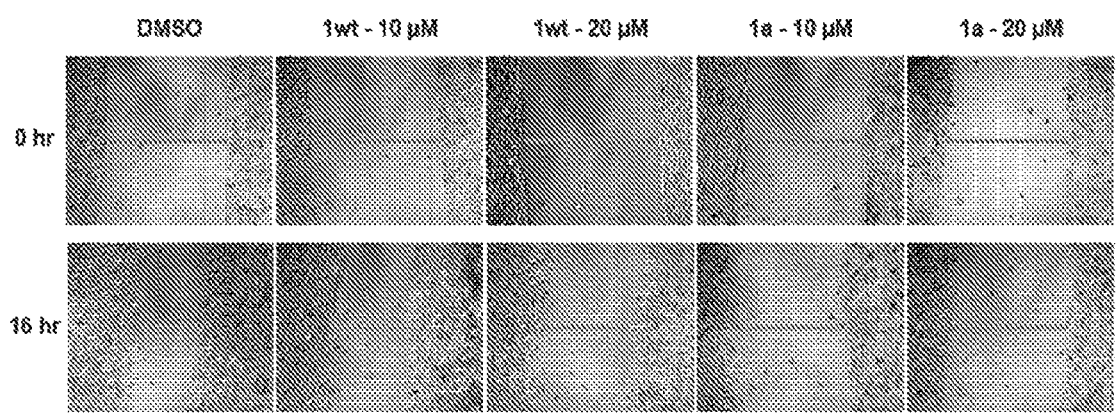
FIG. 4 Representative images from 0 and 16 hr. time points of scratch wound assay with HeLa cells. Treatment conditions included DMSO control, wildtype and DAC RGD peptides 1 wt and 1a. Horizontal lines each represent a single measure of wound distance. Five measurements were taken per view across two biological replicates of each condition. Migration distance was calculated by subtracting 16 hr. distance from 0 hr. distance, averaging, and normalizing to DMSO migration distance.

The RGD motif has seen considerable therapeutic development as an anti-migratory agent targeting aggressive cancers. Like other peptides, in vivo use of native RGD shows limited efficacy due to cleavage by circulating proteases, whereas head-to-tail cyclized analogs demonstrate increased protease resistance and in vivo activity. To test whether DAC peptides similarly display differential protease susceptibility, cyclic 1a and linear analog 1 wt were exposed to an in vitro trypsin sensitivity assay. Native peptide 1 wt was rapidly degraded within two hours (FIG. 10B), whereas DAC 1a showed an extended half-life, with 30% remaining intact after 4 hours. To determine if this effect was applicable to other scaffolds and proteases, the major cyclic isomer of i, i+7 DAC 4a and linear analog 4 wt were subjected to chymotrypsin. As with the RGD scaffold, the linear species 4 wt was degraded more rapidly than 4a (FIG. 10B). Consistent with the increased stability of the cyclized RGD analog, compound 1a was significantly more effective at blocking wound closure, an integrin-mediated phenotype, relative to the linear control peptide 1 wt (FIGS. 4, 10C). Taken together, these results confirm that Diels-Adler cyclization can affect the structure and biological function of loop peptide ligands.

C. Diels-Alder Cycloadducts Preferentially Form with Endo Stereochemistry and Stabilize Peptide Conformation To characterize a putative Diels-Alder cycloadduct and its resulting effects on peptide conformation, 4a and precursor peptides 4 wt and 4 hex were subjected to a series of NMR experiments. $^1$H-NMR of 4a confirmed the presence of two vinylic protons, absent in 4 wt and distinct from those of the diene in 4 hex (FIG. 12A) or α,β-unsaturated maleimido protons. The observed doublet of triplets pattern for the vinylic protons in 4a results from small $^3$J and $^4$J coupling constants of the unsaturated system, indicative of near-90° dihedral angles between neighboring vinyl and allyl protons. TOCSY experiments permitted complete assignment of cyclized and non-cyclized peptides. Direct through-bond coupling was observed between 4a vinylic protons and all protons within the putative cycloadduct (FIG. 12B), supporting the formation of a fused bicyclic adduct. The combination of TOCSY and NOESY experiments resolved the connectivity of the cycloadduct in 4a and revealed extensive through-space interactions between its protons (FIG. 12B). Most notably, interactions between H3/H6 allylic protons and H4/H5 succinimidyl bridgehead protons suggest the cycloadduct in 4a is the endo stereoisomer (FIG. 12B).

Figure 13:
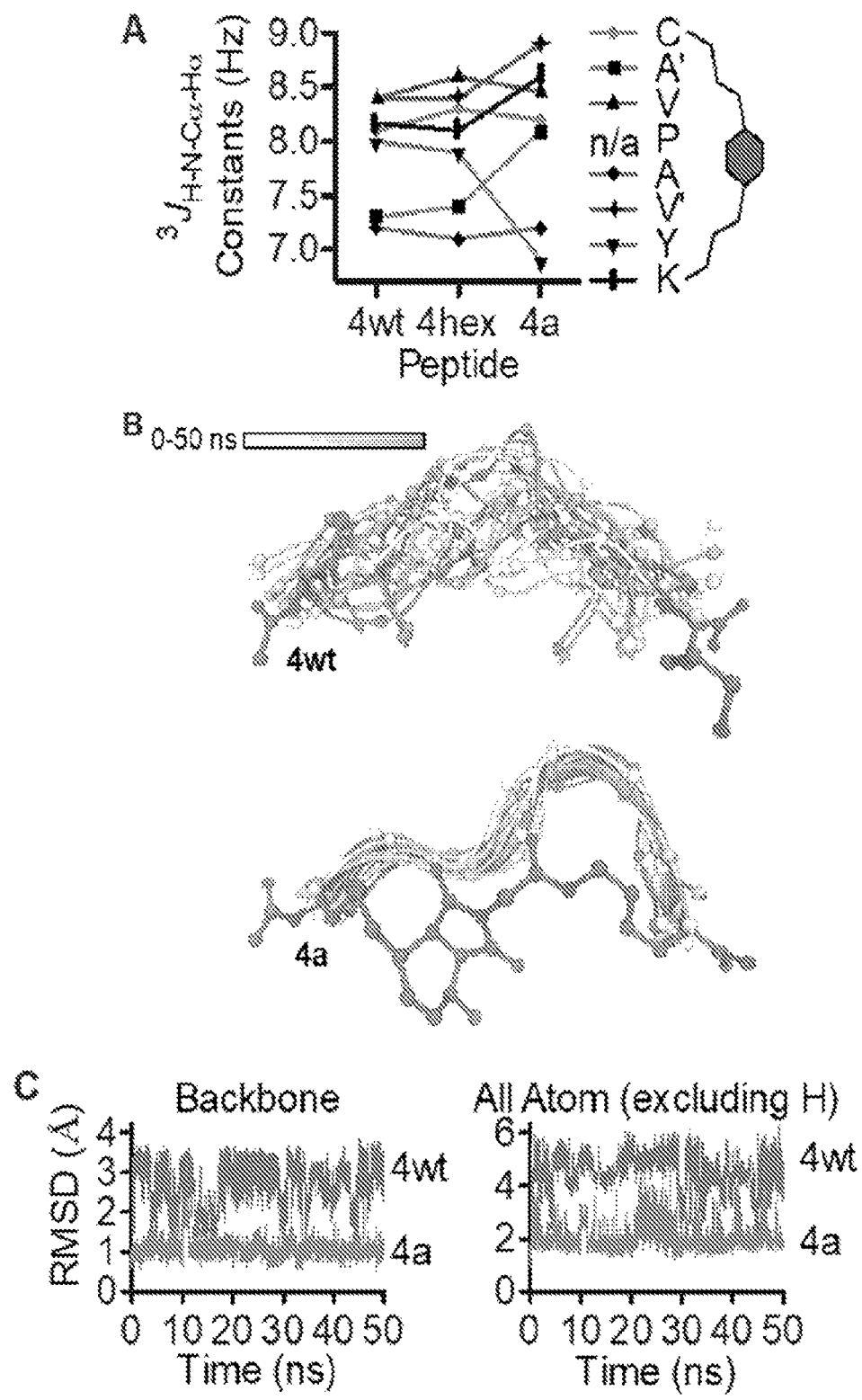
FIGS. 13A-13C FIG. 13A $^3$JH-N-Cα-Hα coupling constant values for each residue of the three peptides studied.

NMR results further revealed substantial perturbation to the cyclic 4a structure relative to linear analogs. Following hexadiene incorporation, only modest changes in chemical shifts were observed for cysteine and nearby residues, with virtually no change in 3J-coupling constants between backbone amide and alpha protons (FIG. 13A). Conversely, 4a displays marked changes in chemical shifts and backbone 3J-coupling constants for several residues, most notably the tyrosine and alanine adjacent to the cyclizing residues (FIG. 13A). These alterations likely result from both cyclization-induced limits on degrees of freedom, as well as emergent intramolecular interactions such as hydrogen-bonding between amide and carbonyl oxygen atoms found on the cycloadduct and peptide.

To further investigate the structure of this i, i+7 DAC peptide, molecular dynamics (MD) studies were carried out on 4 wt and 4a. Briefly, models were built in MOE and run in the NAMD2 simulation package. Trajectory analysis using VIVID revealed linear 4 wt displayed no persistent structure, while cyclized 4a displayed a highly stabilized extended loop structure over 50 ns simulations (FIG. 13B). RMSD measurements of the respective backbones confirm a substantial decrease in 4a conformational flexibility relative to linear 4 wt (FIG. 13C; average backbone RMSD=1.07 Å and 2.69 Å, respectively), which also translated to reduced motion in the side chain dynamics of 4a (FIG. 13C).

Figure 14:
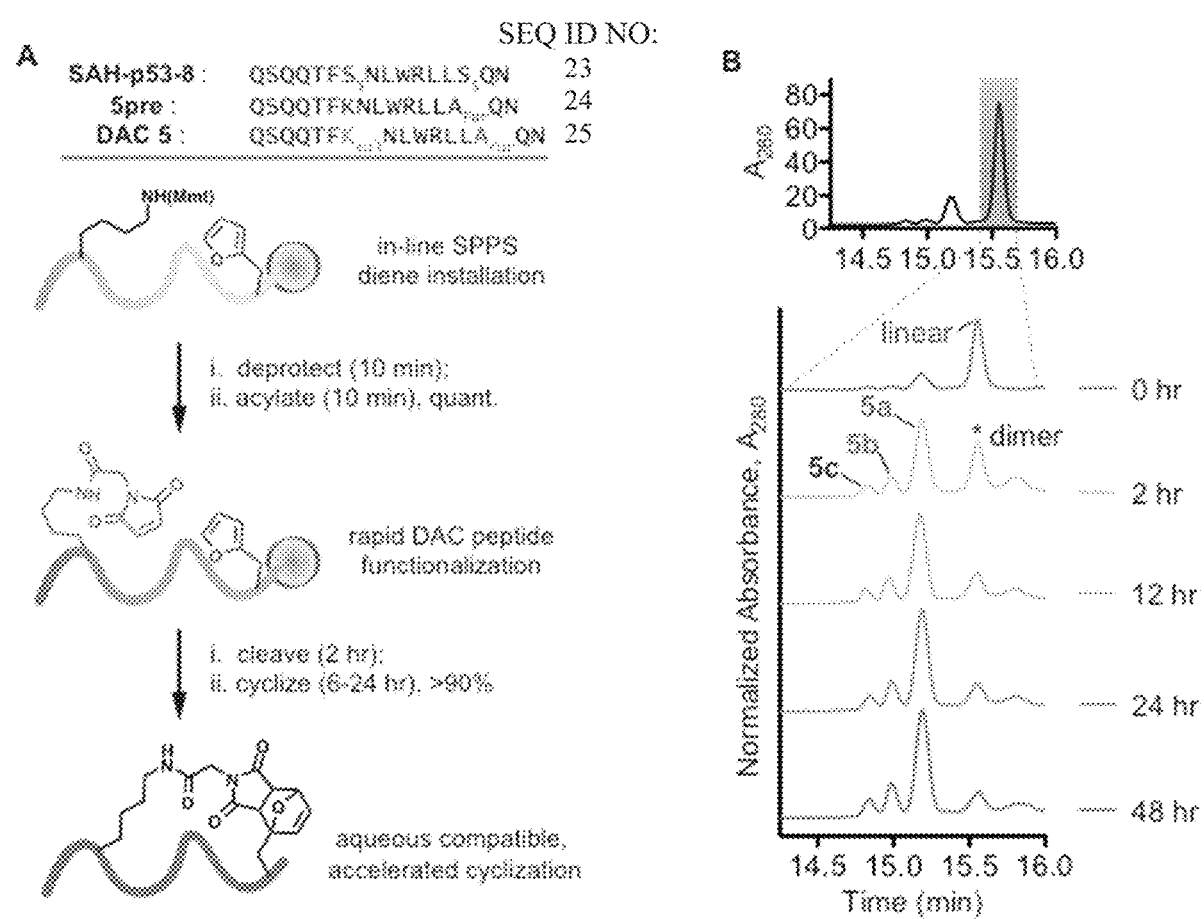
FIGS. 14A-14B FIG. 14A Schematic of DAC-p53 peptide synthesis.
Figure 15:
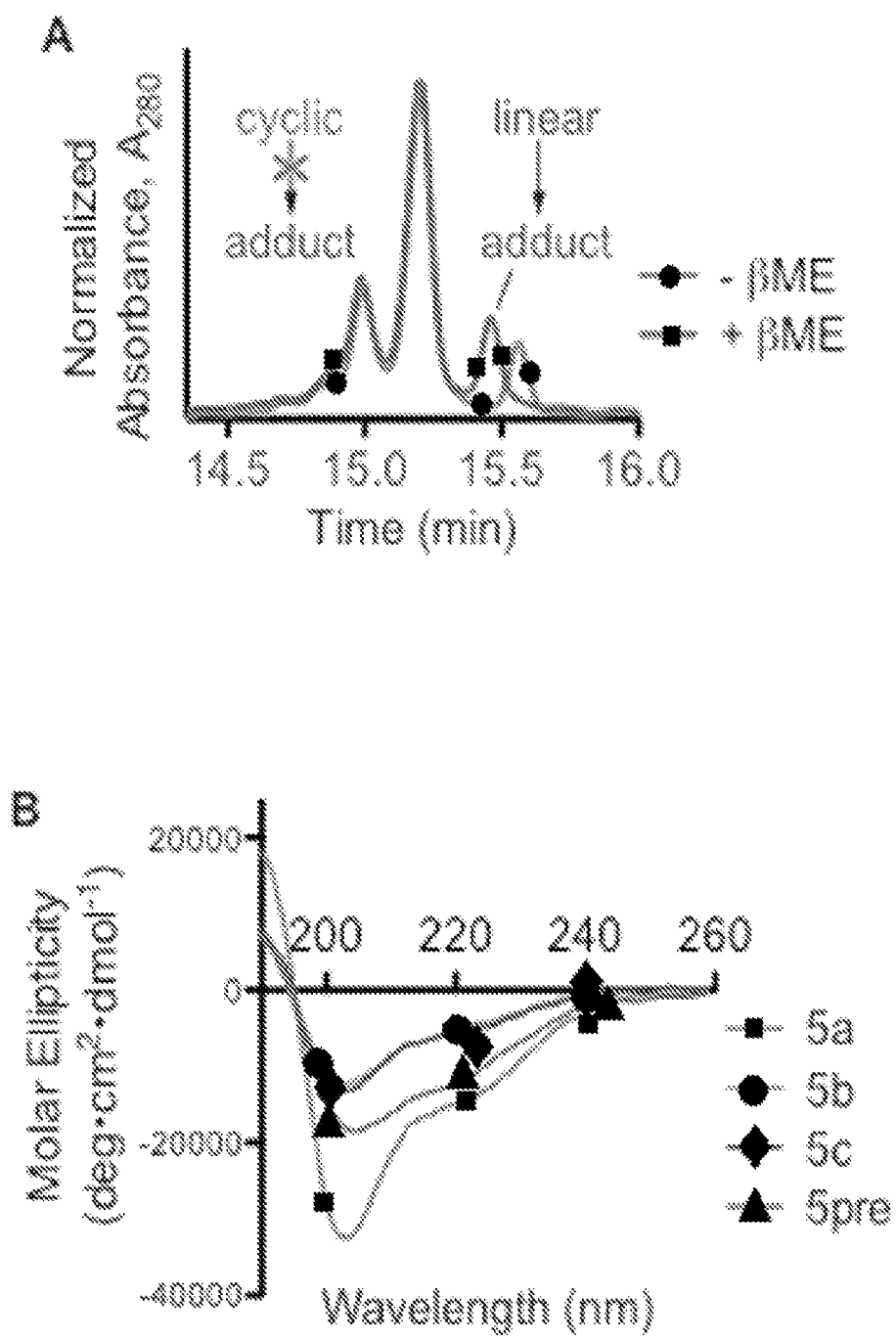
Figure 16:
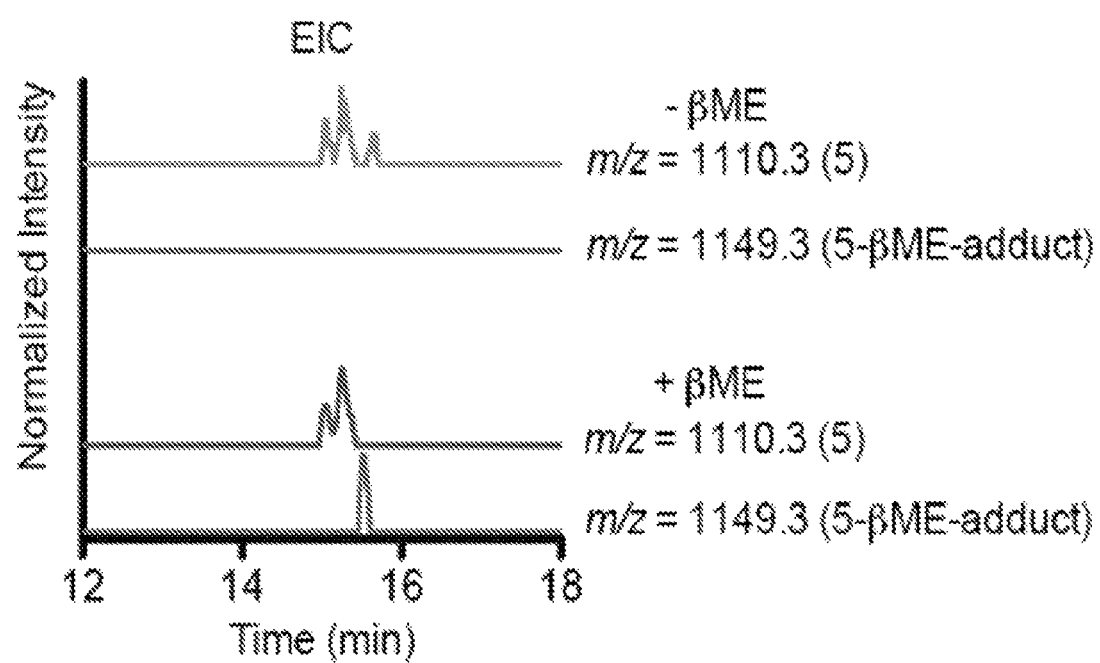
FIG. 16 LC-MS EIC traces of incubation of DAC-p53 peptide 5 mixture with or without excess βME in aqueous buffer, verifying Michael adduction of linear precursor 5 and unreactivity of cyclized isomers.

D. Diels-Alder Peptide Cycloadditions Operate in Aqueous Solution and Stabilize α-Helices Helical peptides represent the dominant structural feature that mediates biomolecular interactions. Diels-Alder cyclization strategies were examined for their ability to stabilize α-helical peptide conformations from diverse peptide sequences. An experiment was performed to determine if a conformationally-restricted and less reactive furan diene could cyclize on a p53-derived helical sequence. Like Fmoc-Cys(2,4-hexadiene)-OH, Fmoc-protected (2-furanyl)alanine (denoted as $A_{Fur}$) was directly incorporated during SPPS (FIGS. 14A, 14B). Notably, the Diels-Alder cyclization reaction using $A_{Fur}$ and $K_{Mal}$ at previously established i, i+7 positions in the p53-derived sequence proceeded slowly on solid support, yielding a dominant linear species that could be purified by HPLC (FIGS. 14A, 14B). Incubation of the isolated linear peptide 5 in physiological PBS buffer, however, resulted in the rapid appearance of earlier-eluting cyclized species and a minor fraction of peptide dimers (FIG. 14B). Michael-addition trapping experiments confirmed that the putatively cyclized compounds 5a, 5b and 5c lacked the reactive maleimide, which contrasted with the isolated linear peptide 5 (FIGS. 15A, 16). Circular dichroism spectroscopy of the linear control p53 sequence and all three isolable cyclized species confirmed increased α-helical character for the dominant DAC peptide 5a relative to the minor products 5b and 5c (FIG. 15B). These data are reminiscent of other studies reporting that stereochemical yield is correlated with global stability of the peptide fold, here suggesting that the aqueous chemical environment may aid in the selection of favorable adducts that promote global helix stabilization.

Figure 17:
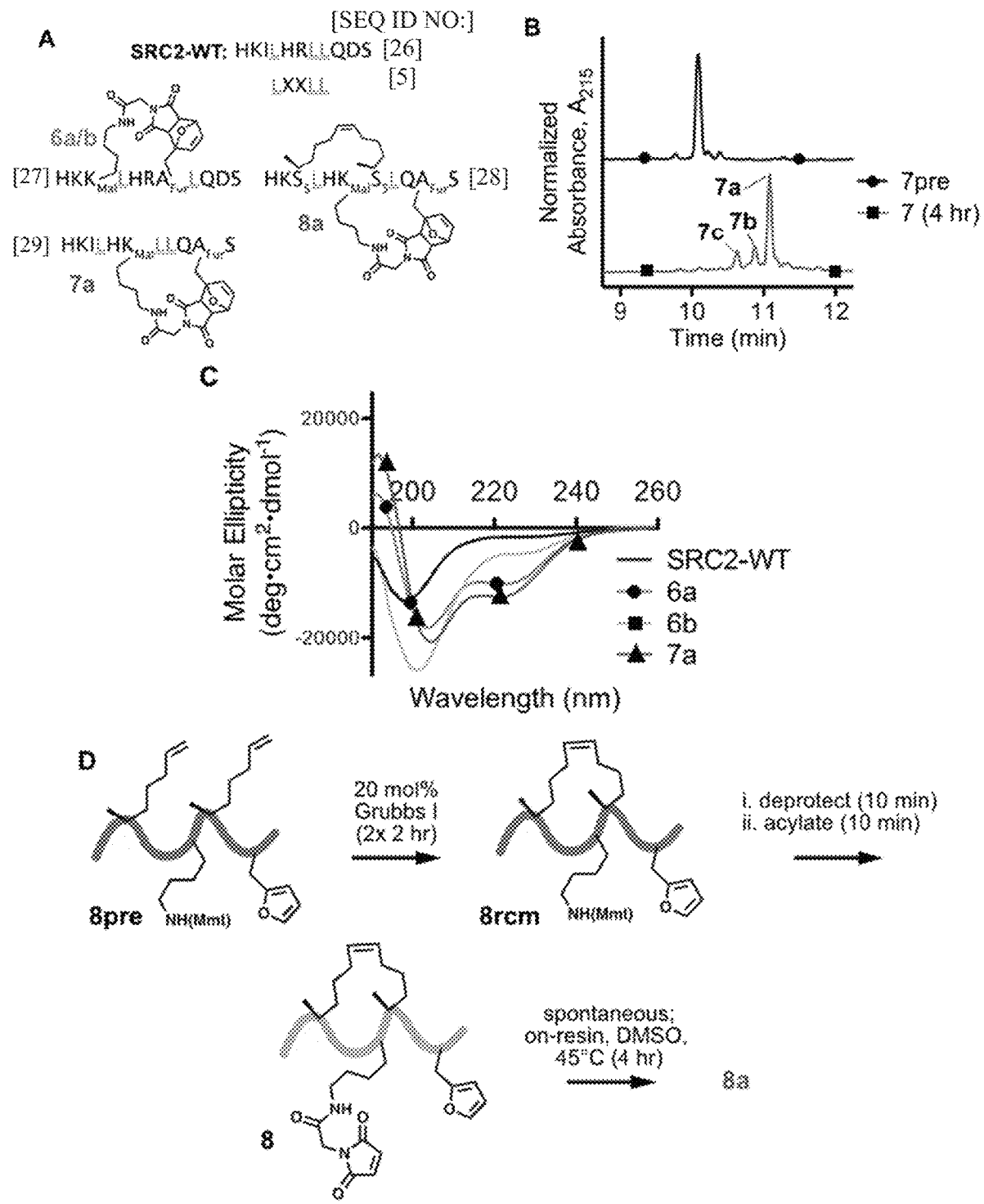
Figure 18:
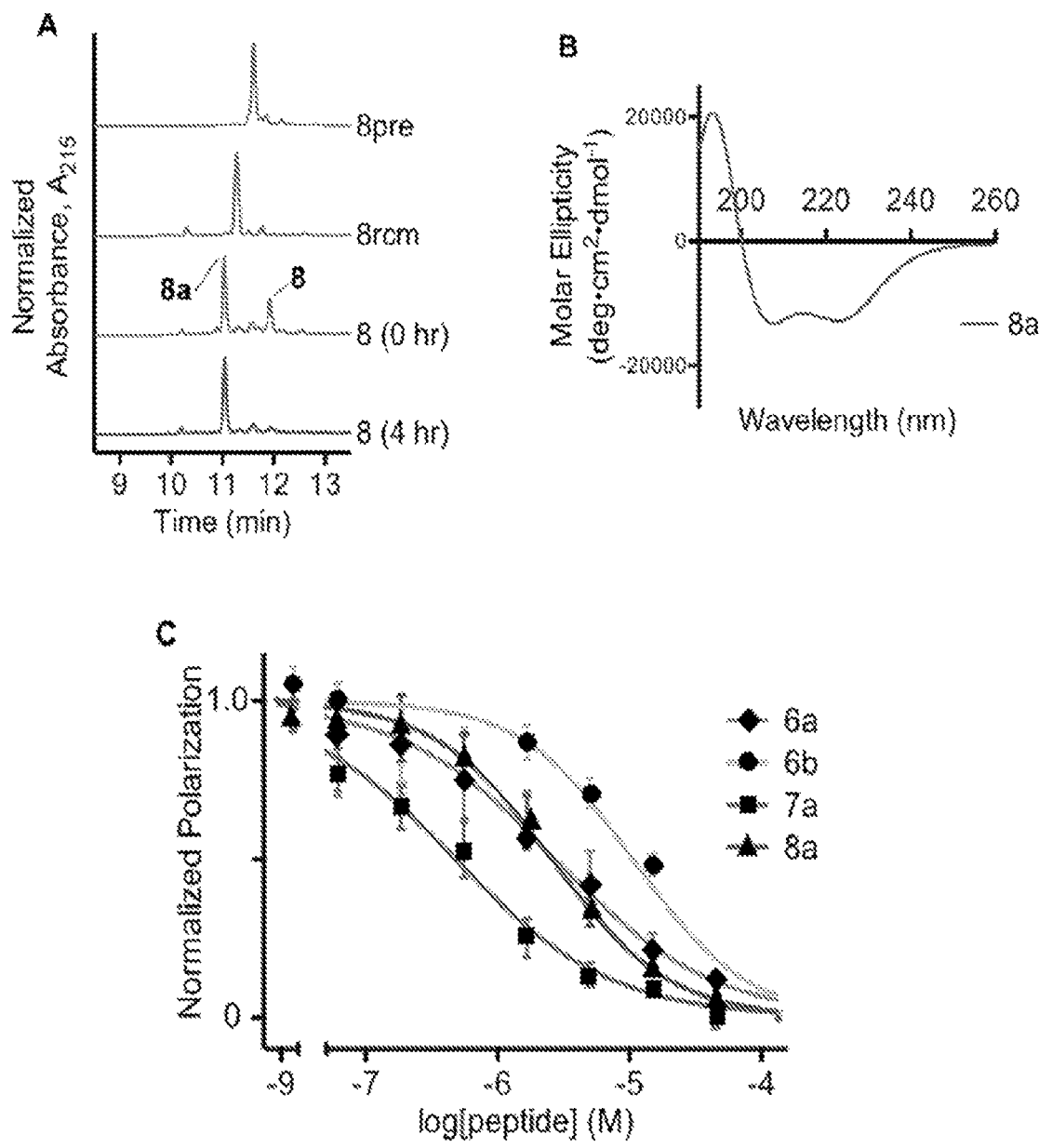
Figure 20:
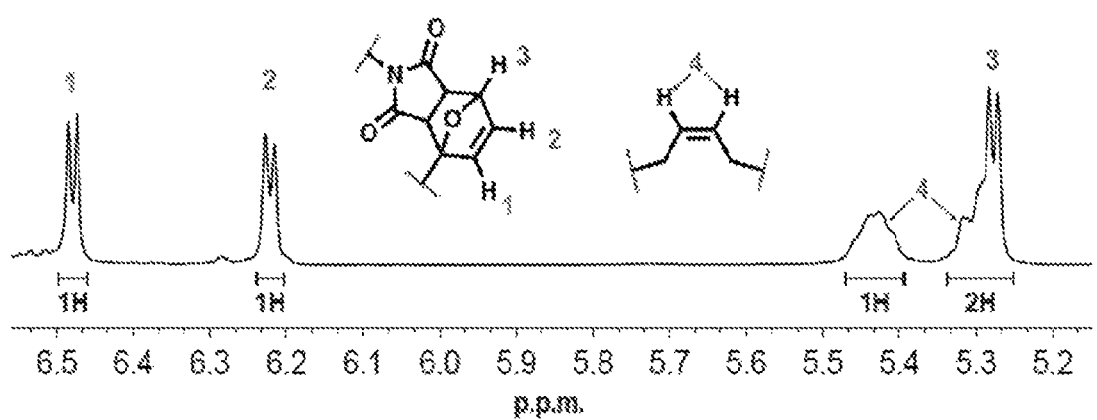

E. Diels-Alder Cycloadduct Geometry, Alone or in Tandem with Other Chemistries, Differentially Affects Peptide Helicity and Activity To further explore the potential to stabilize diverse helical conformations, a series of Diels-Alder stabilized, α-helical peptides derived from the co-activator protein SRC2 were synthesized. A short helical stretch within this protein contains a conserved LXXLL (SEQ ID NO: 5) motif that engages a hydrophobic groove in estrogen receptor-α (ERα; FIG. 17A). Several 1, i+4 'DAC-stapled' peptides were synthesized, which were tolerant of direct 2-furanylalanine incorporation during SPPS. Unlike the p53-derived sequence, both SRC2 peptides 6 and 7 cyclized on resin rapidly and in high yield following maleimide incorporation (FIGS. 17B, 19). The two isolable cyclized species 6a and 6b, and the one dominant compound 7a were characterized by CD spectroscopy. The dominant species 6a and 7a were significantly more helical than either the unmodified wild-type SRC2 peptide or minor 6b compound (FIG. 17C). Previous attempts to stabilize the SRC2 LXXLL (SEQ ID NO: 5) motif have shown that hydrophobic residues that engage ERα can be replaced by a hydrocarbon staple without significant loss in binding affinity. Therefore, experiments were performed to test whether a double-stapled SRC2 ligand containing both a hydrocarbon staple installed by ring closing metathesis of olefin containing amino acids in concert with Diels-Alder cyclization of a diene-dienophile pair could be synthesized. Direct incorporation of olefin-containing $S_5$ amino acids and furan yielded a clean peptide precursor, 8 pre, that was readily cyclized by Grubbs-I catalyst (8 rcm; FIGS. 17C, 18A). Subsequent introduction of the maleimide dienophile resulted in immediate appearance of an earlier eluting tandem stapled peptide, which was the stoichiometric product after mild heating for 4 hr. on resin (FIGS. 18A, 19). CD characterization of this bicyclic peptide 8a revealed classic α-helical minima at 208 and 222 nm (FIG. 18B). $^1$H-NMR analysis confirmed the presence of Diels-Alder cycloadduct vinylic protons and a single allylic proton in all major DAC SRC2 peptide products, and, in the case of 8a, peaks corresponding to the RCM alkene product were observed (FIG. 20).

To probe the structure activity relationships of these DAC-SRC2 peptides, competitive fluorescence polarization binding assays were performed with ERα. Both the single DAC-stapled 7a and tandem stapled 8a peptides competed a fluorescein-linked SRC2 peptide off of ERα with $IC_{50S}$ of approximately 0.5 and 2.5 μM respectively (FIG. 18C, Table 3). Intriguingly, the dominant, more helical isomer 6a demonstrated 4-fold improved activity compared to the less helical, minor product 6b (FIG. 18C, Table 3). These results echo those observed for the p53 sequence, where stereochemical yield is correlated with overall peptide fold stabilization, and in the case of SRC2 improved biochemical potency.

TABLE 3

Calculated $IC_{50}$ and $K_i$ values from competitive FP assay of DAC-SRC2 peptides targeting ERα.

| μM (± s.e.m.) | 6a | 6b | 7a | 8a |
|---|---|---|---|---|
| $IC_{50}$ | 2.74 (0.095) | 10.6 (0.160) | 0.48 (0.004) | 2.56 (0.100) |
| $K_i$ | 1.19 (0.041) | 4.61 (0.068) | 0.21 (0.001) | 1.12 (0.045) |

Figure 21:
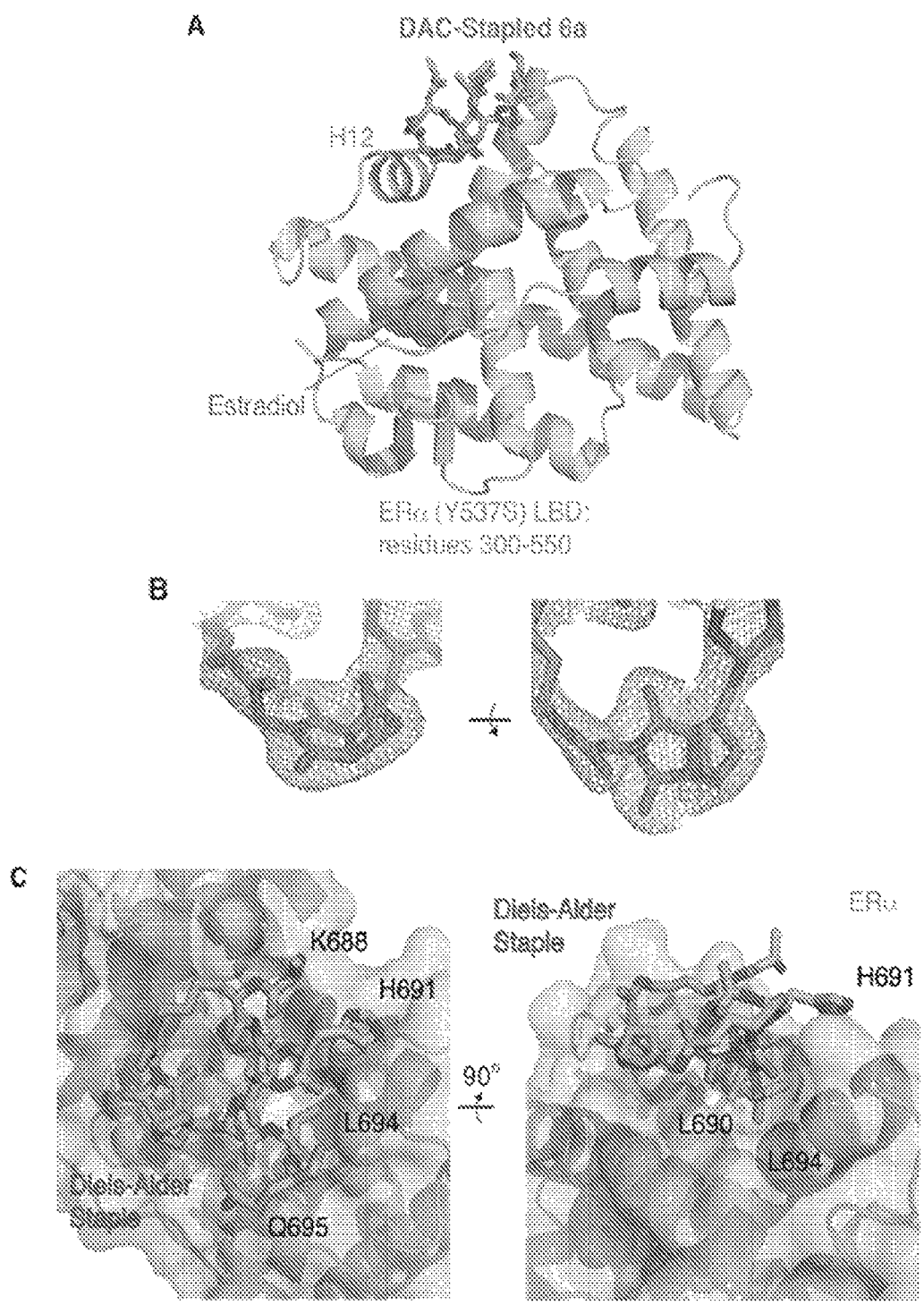
FIGS. 21A-21C FIG. 21A X-ray crystal structure of Diels-Alder cyclized SRC2 peptide 6a bound to estrogen receptor-α (PDB: 6 PIT). LBD of ERα Y537S mutant protein bound with estradiol and 6a located in the AF2 cleft.
Figure 22:
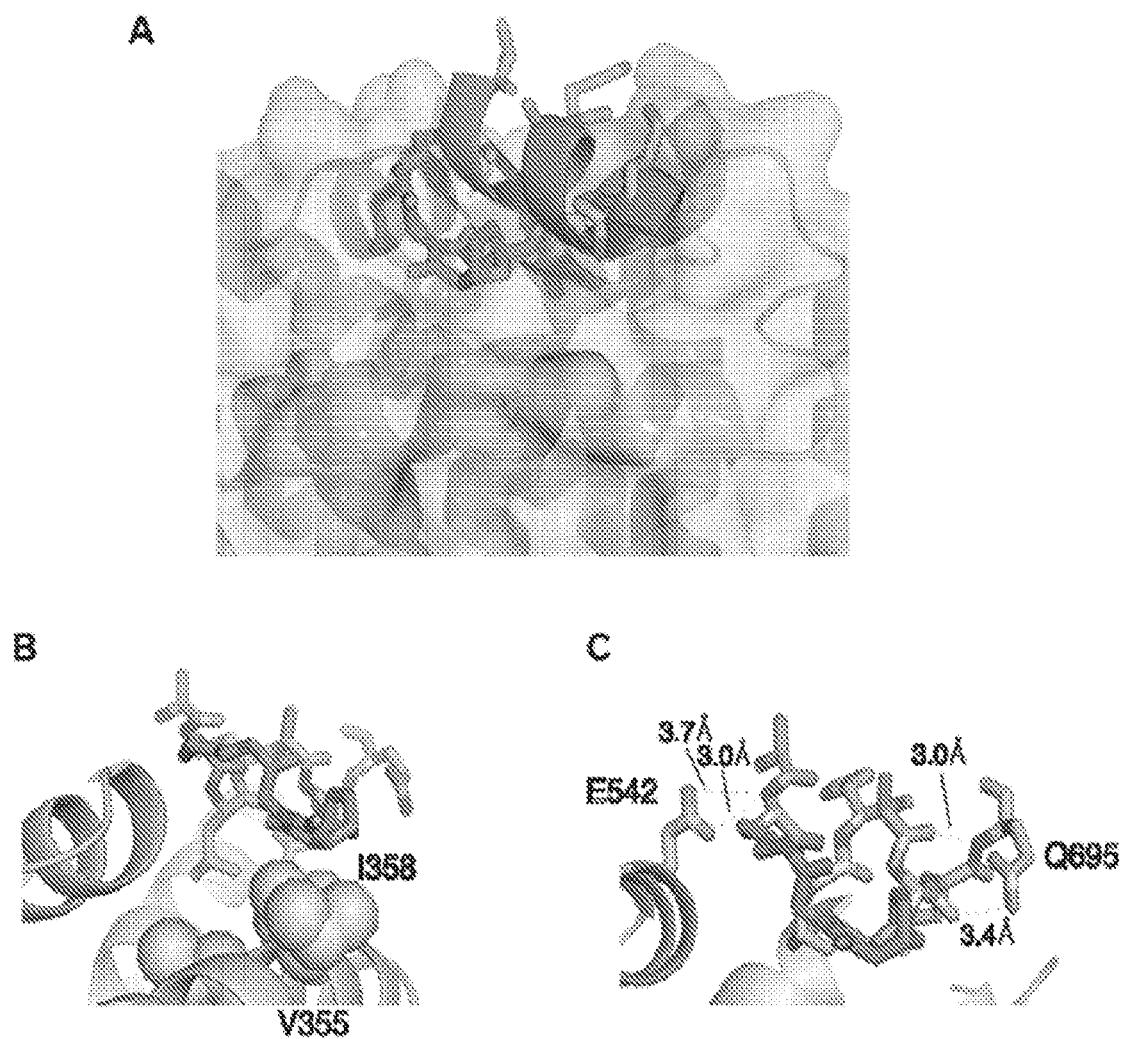
FIGS. 22A-22C FIG. 22A Detail of X-ray crystal structure results of Diels-Alder cyclized SRC2 peptide 6a bound to estrogen receptor alpha. The DAC-stapled peptide 6a overlays with a similar LxxLL motif containing peptide from transcriptional Intermediary Factor 2 (TIF2) peptide bound to ERα (PDB 1GWR)21.

F. X-Ray Crystal Structure of a DAC Stapled SRC2 Peptide-ERα Complex Demonstrates Cycloadduct Stereochemistry and Contribution to Target Binding To determine the structure of the Diels-Alder adduct in 6a and its role in promoting the interaction with ERα the X-ray structure of 6a and estradiol co-crystallized with residues 300-500 of the ERα ligand binding domain (LBD) at 2.25 Å resolution was solved (FIG. 21A). The Y537S mutant of ERα was used as it stabilizes the agonist conformation of the receptor and aids in crystal formation. An FO-Fc difference map using wild-type SRC2-bound ERα confirmed the unambiguous presence of estradiol bound in the core of the LBD, and DAC-stapled 6a bound in the canonical activating function 2 (AF2) cleft of ERα (FIGS. 21A, 22A, 22B). The Diels-Alder adduct was highly ordered and permitted unequivocal confirmation that the more stabilizing and dominant stereochemical product in the context of SRC2 is that of the endo isomer (FIG. 21B). The endo bicycle presents a convex hydrophobic surface that directly contacts ERα residues Val355, Ile358 and Leu539 that form the hydrophobic shelf adjacent to the cleft that binds the LXXLL (SEQ ID NO: 5) motif (FIG. 21C). Residues in 6a that are derived from Leu690 and Leu694 in SRC2 retained their canonical contacts and were deeply engaged with a network of hydrophobic residues in the AF2 groove (FIG. 21C). Additional orienting contacts are mediated by His691 to the edge opposite the Diels-Alder adduct, as well as a conserved hydrogen bond between Glu542 of ERα that caps the N-terminus of the peptide helix (FIG. 22C). At the C-terminus the last ordered residue present in the DAC-peptide structure, Q695, folds back on the peptide to satisfy a hydrogen bond to the i-2 amide carbonyl, effectively capping the helix (FIG. 22C). Taken together, these structural data confirmed that the unique Diels-Alder chemical and stereochemical composition can stabilize an active helical conformation and directly contribute to target engagement, as evidenced here by forming a molecular "clasp" around the core and edge of the ERα AF2 cleft.

G. Materials and Methods

DAC peptide synthesis, purification and analysis. Peptides were synthesized by Fmoc-based solid phase peptide synthesis (SPPS), ring-closing metathesized (where appropriate) and purified by reverse-phase HPLC with a C18 column. Fmoc-Cys(2,4-hexadiene)-OH and Fmoc-(2-furanyl)alanine-OH were incorporated in a similar manner on resin. Peptides were analyzed by LC-MS using a C18 reverse-phase column (Phenomenex, 5.0×50 mm, pore size 110 Å, particle size 5 μm); Buffer A (5/95/0.1% ACN/H2O/TFA) and Buffer B (95:5:0.1% ACN/H2O/TFA); and a 20 min method with the following gradient (flow rate 0.5 mL/min): 0% buffer B over 3 min, 0-65% buffer B over 15 min, 65-100% buffer B over 1 min; 100-0% buffer B over 1 min. Purified peptides were lyophilized in tared low-retention microcentrifuge tubes, quantified by mass and UV absorbance where relevant, and either brought forward for structural characterization or dissolved in DMSO as 10 mM stocks and stored at −20° C. for later use.

N-(9-fluorenylmethoxycarbonyl)-L-cysteine. To a suspension of 1.76 g N-(9-fluorenylmethoxycarbonyl)-S-trityl-L-cysteine (3 mmol) in 50 mL dichloromethane was added 3 mL triisopropylsilane (14.6 mmol), followed by 10 mL trifluoroacetic acid (131 mmol). The resulting mixture was stirred at room temperature for 10 minutes until it turned colorless. The solvent was removed under reduced pressure and the residual mixture was triturated by hexanes, yielding 1.03 g white solid (quantitative), which was directly used in the following step without further purification.

N-(9-fluorenylmethoxycarbonyl)-S-(trans,trans-2,4-hexadienyl)-L-cysteine. A solution of 1.03 g N-(9-fluorenylmethoxycarbonyl)-L-cysteine (3 mmol) and 0.83 g potassium carbonate (6 mmol) in 50 mL N,N-dimethylformamide was protected under nitrogen and cooled to 0° C. 0.58 g trans,trans-2,4-hexadienyl bromide (3.6 mmol) was added, and the reaction mixture was stirred for 1 hour at 0° C. under nitrogen. After the reaction was complete as monitored by TLC, 50 mL water was added and the mixture was acidified to pH 2 with 1 N HCl. The mixture was extracted with ethyl acetate (50 mL×3). The organic layer was then combined, washed with 5% LiCl (25 mL×4), brine (50 mL×2) and dried over sodium sulfate. The solvent was removed under reduced pressure, and the crude mixture was purified by flash chromatography to yield 0.77 g off-white solid (61%) with Rf=0.15 (9:1 dichloromethane/methanol).

DAC peptide functionalization. DAC peptide functionalization was carried out on 30 μmol MBHA rink amide (0.86 mmol/g) or NOVAPEG (0.31 mmol/g) resins following SPPS and N-terminal acetylation. When necessary, Cys-StBu deprotection was achieved by bubbling with $N_2$ in 3 mL 20/10/70% βME/DIPEA/DMF, 2×2 hr. Following copious washing with DMF and DCM, Cys alkylation was carried out to completion with 19 mg bromohexadiene (4 eq; 120 μmol) and 41 μL DIPEA (8 eq; 240 μmol) in 3 mL DMF, 4 hr. at room temperature, as monitored by LC-MS analysis. Following washing with DMF and DCM, Lys-Mmt deprotection was achieved by bubbling with $N_2$ in 3 mL 1% TFA/DCM, 5×2 min. Following copious washing with DCM and DMF, Lys acylation was carried out by first pre-activating 4.65 mg N-maleimidoglycine (3 eq; 90 μmol) with 37 mg HCTU (3 eq; 90 μmol) for 10 min in 0.5 mL DMF. The solution was then added to the resin with free amine-containing peptide with 1 mL DMF and 16 μL DIPEA (3 eq; 90 mop and bubbled with $N_2$ for 5-10 min. Following copious washing and drying of the resin and peptide cleavage, complete maleimide incorporation and macrocyclization was analyzed by LC-MS. Similar procedures were followed for the incorporation of acryloyl and crotonoyl functional groups onto free Lys on resin.

DAC peptide 1 cyclization time-course. Cys-alkylated 1 hex was lysine-functionalized with N-maleimidoglycine dienophile according to the above protocol. Resin was then dried. A sample was reserved for analysis at 4° C. and remaining resin split into 4 samples. These samples were brought up in DMF and agitated at 1,000 rpm at room temperature for 30 min, 1 hr, 2 hr, and 6 hr. At each time point, solvent was removed by filtration, resin dried, peptide cleaved, and product profile analyzed and quantified by LC-MS.

Optimization of DAC peptide reaction conditions. On resin reaction condition screens were carried out immediately after N-maleimidoglycine acylation of RGD peptide 1 hex as described above. Briefly, dry resin (~2-5 μmol) was split between microcentrifuge tubes and 500 µL of the indicated solvents were added and incubated at room temperature or 45° C. for 2 hr. Following peptide cleavage, each reaction profile was analyzed by LC-MS. All future on-resin cyclization reactions were carried out in DMSO and heated at 45° C. for 2-6 hr as empirically determined by DAC peptide conversion profiles as observed by LC-MS.

DAC peptide maleimide trapping and cyclization experiment. Cys-alkylated 1 hex was lysine-functionalized with N-maleimidoglycine dienophile according to the above protocol. Resin was then split and either incubated in DMF or 20% βME/DMF for 2 hr. Following copious washing, solvent was removed by filtration, resin dried, peptide cleaved, and product profile analyzed by LC-MS.

DAC peptide cycloadduct chemical stability assay. Purified, lyophilized peptide 1a (1 eq) or a mixture of cyclic and linear peptide 5 (1 eq) were dissolved in PBS, pH 8.0. βME was added (20 eq) and the solution incubated at 37° C., 1,000 rpm. 2 hr, 6 hr, and 24 hr time-points were frozen and lyophilized (a single 2 hr time point was taken for 5). Lyophilized samples were dissolved in 0.1% TFA/$H_2O$ and analyzed by LC-MS.

DAC protease stability assays. DAC peptide protease degradation kinetics were determined with Thermo Pierce™ MS-Grade Trypsin or Chymotrypsin Protease in PBS or TBS with 5 mM DTT and 2 mM $CaCl_2$. Protease (1 eq) was added to buffer for a final assay concentration of 10 µg/mL trypsin or 0.5 µg/mL chymotrypsin. Each respective reaction mixture was then added to either 1 wt and 1a (2000 eq) or 4 wt and 4a (10,000 eq). Samples were then incubated at 37° C., 1,000 rpm. 5 min, 10 min, 30 min, 2 hr, and 4 hr time points were quenched in an equal volume of 2% TFA/$H_2O$ on ice. After 5 min, samples were centrifuged for 2 min at 17,000 rcf to precipitate quenched trypsin. Supernatant solutions were then analyzed and intact peptide quantified by LC-MS or Q-TOF.

DAC scratch wound assay. 100,000 HeLa cells were seeded in each well of a 24 well plate in 1 mL RPMI (GIBCO) supplemented with 10% FBS. Cells were incubated at 37° C., 5% $CO_2$ and reached ~70% confluency within 24 hr. Each well's monolayer of cells was scratched with a sterile 200 µL pipette tip, media and debris was aspirated, wells washed with PBS and then fresh, RPMI was added, containing either DMSO, 10 µM or 20 µM compounds 1 wt or 1a. Brightfield microscopy images of each well's wound were taken immediately after wounding (time=0 hr) and following overnight incubation with compounds (time=16 hr). Two biological replicates were performed for each condition and at least 5 wound distance measures were taken from each image, averaged and normalized relative to the distance of wound closure in the DMSO control.

NMR spectroscopy. ~2-4 mg peptide was dissolved in 400 µL $d_6$-DMSO for NMR experiments. All experiments were performed on a Bruker AVANCE II+500 MHz NMR (1a, 2a, 3a, 4 wt, 4 hex, 6a, 7a, 8a) or Bruker AVANCE IIIHD 600 MHz NMR (4a) using standard acquisition parameters with empirically determined 90 degree pulse widths and in-house methods for solvent suppression for 4a spectra. Data were processed and plotted in Bruker Topspin 3.5 and MestReNova 11.0.2.

Molecular modeling. A structural model of 4a was built using the Molecular Operating Environment molecular modeling package. In accordance with NMR analysis, the endo configuration of the Diels-Alder adduct was enforced and backbone torsion angles were manually adjusted according to measured J-coupling constants. Missing atom names for the covalent linker were assigned and the final structure was exported using the PDB format. Custom topology files for the covalent linker were used to reconstruct the molecular system in CHARMM format (PSF+PDB) using the PSFGEN plugin for VIVID. A custom patching protocol was used to prepare the cyclic peptide in silico and the N-terminal acetyl and C-terminal amidate patches were used to match the synthesized chemical structure. The SOLVATE plugin was used to generate a 15 Å TIP3P7 water box and the AUTOIONIZE plugin was used to bring the salt concentration to 0.1 M NaCl. The solvated system totaled ~9.3K atoms. Aside from lacking the covalent linker, the linear peptide was constructed using the same method. The NAMD 2.12 software package was used for molecular dynamics simulations. The peptide and ions were described using the CHARMM36m forcefield. The required parameters for the covalent linker were assigned by analogy from the CHARM36m and CGENFF parameter sets. All simulations were performed at a target temperature of 298K and a pressure of 1 atm maintained by a Nosé-Hoover thermostat and Langevin piston. Periodic boundary conditions were applied, full system periodic electrostatics were computed using the particle mesh Ewald (PME) method with a grid spacing set to >1/Å, and non-bonded interactions were treated using an exponential switching function with a switch distance of 10 Å and cutoff of 12 Å. The solvated and ionized systems were energy minimized (20 ps) and velocities were introduced with a harmonic constraint scaling factor of 2 set for all non-hydrogen atoms of the peptides. Following 1 ns of equilibration the harmonic constraints were removed and production simulations were run for an additional 50 ns. The simulation trajectory files were down-sampled to 10 ps/frame for analysis. Simulation trajectories were aligned to the peptide backbone of the first frame of the respective production run and RMSD was found for the backbone or non-hydrogen atoms using the RMSD Trajectory Tool in VMD. The output RMSD values were plotted using GraphPad PRISM. An overlay of the peptide backbone at 250 ps intervals was generated for the image displayed in FIG. 13B.

DAC peptide 5 in-solution cyclization time-course. Furan-containing peptide 5 pre was lysine-functionalized with N-maleimidoglycine dienophile, resin was dried and then peptide cleaved according to the above protocols. The resulting crude peptide was then subjected to HPLC purification and the predominant linear isomer 5 was isolated and lyophilized overnight. The linear species was then dissolved in PBS and incubated at room temperature. Time points were removed at 0, 2, 12, 24 and 48 hr, at which points the product profile was analyzed by LC-MS.

Circular dichroism (CD) spectroscopy. CD spectroscopy experiments were performed on a Jasco J-170 using a quartz cuvette (path length: 0.1 cm). Peptides were dissolved to 50 µM in 50 mM phosphate buffer (pH 7.4) and CD measurements were recorded at 0.5 nm increments between 190 and 260 nm, at room temperature.

Competitive fluorescence polarization (FP) assay. FP experiments were performed in black 96 well plates (Corning) on a Synergy Neo plate reader (BioTek). 3-fold dilution series of DAC peptides 6a, 6b, 7a and 8a were plated in 60 µL FP buffer (20 mM Tris-HCl, pH 7.5, 50 mM NaCl, 0.01% NP-40), and further diluted by the addition to each well of 30 µL FP buffer containing 750 nM wildtype ERα wildtype protein, 3.75 µM estradiol (E2), and 10 nM FITC-SRC1-BoxII peptide (final volume 90 µL; final concentrations: 250 nM ERα, 1.25 µM E2, and 3.3 nM tracer peptide). Plates were incubated at 4° C. for 1 hr, imaged using standard FP assay settings at 30° C., and data analyzed as previously described.

Protein Expression and Purification. Wildtype and Y537S 6×His-TEV-ERα (residues 300-550) in pET21a(+) was expressed in *E. coli* BL21(DE3) as described. Cells were resuspended in a lysis buffer comprised of 20 mM HEPES pH 8.0, 500 mM NaCl, 40 mM imidazole pH 8.0, 5% glycerol, 15 mM betamercaptoethanol (BME), Sigma-FAST protease inhibitor cocktail, and lysed using sonication. Cellular debris was removed by centrifugation at 22,000 g for 30 minutes at 4° C. The soluble fraction was placed onto a column with Ni-NTA resin that was pre-equilibrated with 20 mM HEPES pH 8.0, 500 mM NaCl, 40 mM imidazole pH 8.0, 15 mM BME, and 5% glycerol (wash buffer). The column was washed with 10 column volumes of wash buffer and protein was eluted with buffer plus 500 mM imidazole pH 8.0. The His-tag was removed by incubation with 1:15 w/w ratio of 6×-His-Tev protease:ERα LBD overnight in 4 L of wash buffer at 4° C. then passed over Ni-NTA resin to capture the His-tag and TEV protease. Protein was concentrated to 5 mL using a spin concentrator at 4° C. then further purified on a Superdex 200 HiLoad 200 16/600 size exclusion column equilibrated with 20 mM pH 8.0, 150 mM NaCl, 15 mM BME, and 5% glycerol. A single peak was observed on the chromatogram and fractions corresponding to that peak for pooled and concentrated to 10 mg/mL. Aliquots were flash frozen and stored at −80° C.

Co-Crystallization and X-Ray Data Collection of Y537S ERα LBD in Complex with Estradiol and 6a. Purified Y537S ERα LBD was incubated with 1 mM estradiol (E2) at 1.025 mM 6a overnight at 4° C. then centrifuged at 20,000 g for 30 minutes at 4° C. to remove insoluble ligand. Co-crystals were generated using hanging drop vapor diffusion where 1 μL of protein complex was mixed with 1 μL well solution. Clear rectangular crystals emerged in 20 mM Tris pH 8.0, 15% PEG 3,350, 200 mM $MgCl_2$ after 1 week at room temperature. Crystals were cryo-protected in paratone-N. Diffraction data was collected at the Advanced Photon Source, Argonne National Laboratories, Argonne, Illinois, at the SBC 19-BM beamline (0.97 Å). Data were indexed, scaled and merged using HKL-300016. Molecular replacement was performed in Phenix using PDB: 6 CBZ as the search model with ligand and peptide removed. The model was refined using iterative rounds of Phenix Refine and manual inspection with Coot. Ligand constraints for 6a were generated using Elbow. Poorly resolved atoms/residues were not included in the final model. The structure was deposited in the Protein Data Bank with the accession code 6 PIT. All x-ray crystal structure images were generated using Pymol. FIG. 21B shows the electron density map for the adduct of 6a that corresponds to protein chain A.

H. Spectroscopic Data

Fmoc-Cys(2,4-hexadiene)-OH-1H-NMR (500 MHz, $CDCl_3$-d1) δ7.75; (d, 2H, Ar CH), 7.60; (t, 2H, Ar CH), 7.39; (t, 2H, Ar CH), 7.31; (t, 2H, Ar CH), 6.33; (br d, 1H, NH), 5.97-6.08; (m, 2H, C=CH), 5.62-5.68; (m, 1H, C=CH), 5.42-5.47; (m, 1H, C=CH), 4.60; (m, 1H, α-H), 4.41 (d, 2H, Fmoc CH2), 4.23; (t, 1H, Fmoc CH), 3.16; (d, 2H, β-H), 2.98; (d, 2H, S—CH2), 1.70; (d, 3H, CH3).

4 wt (Ac-CAVPAVYK)-1H-NMR (500 MHz, DMSO-$d_6$) δ9.19; (s, 1H), 8.20; (d, J=7.3 Hz, 1H), 8.12; (d, J=8.1 Hz, 1H), 8.09; (d, J=7.2 Hz, 1H), 7.95; (d, J=8.0 Hz, 1H), 7.89; (d, J=8.17 Hz, 1H), 7.84; (d, J=8.4 Hz, 1H), 7.73; (s, 3H), 7.62; (d, J=8.4 Hz, 1H), 7.16; (s, 1H), 7.07; (s, 1H), 7.01; (d, J=8.4 Hz, 2H), 6.62; (dd, J=8.3 Hz, 2H), 4.44; (q, 1H), 4.38; (q, 1H), 4.31; (m, 3H-overlap), 4.25; (m, 1H), 4.14; (q, 1H), 4.09; (q, 1H), 3.68; (d, 1H), 3.56; (d, 1H), 2.91; (dd, J=14.3, 4.7 Hz, 1H), 2.74; (m, 3H-overlap), 2.66; (m, 2H), 2.38; (t, J=8.5 Hz, 1H), 2.01; (m, 1H), 1.94; (m, 1H), 1.9; (m, 1H), 1.87; (s, 3H), 1.86 (m, 1H), 1.80; (m, 2H), 1.66; (m, 1H), 1.51; (m, J=8.2 Hz, 3H), 1.27; (m, 2H), 1.19; (m, 6H-overlap), 0.91; (d, 3H), 0.87; (d, 3H), 0.75; (d, 6H).

4 hex (Ac-C$^{hex}$AVPAVYK)-1H-NMR (500 MHz, DMSO-$d_6$) δ9.19; (s, 1H), 8.26; (d, J=7.4 Hz, 1H), 8.16; (d, J=8.3 Hz, 1H), 8.09; (d, J=7.1 Hz, 1H), 7.95; (d, J=7.9 Hz, 1H), 7.89; (d, J=8.1 Hz, 1H), 7.77; (d, J=8.4 Hz, 1H), 7.72; (s, 3H), 7.62; (d, J=8.6 Hz, 1H), 7.15; (s, 1H), 7.07; (s, 1H), 7.01; (d, 2H), 6.62; (d, 2H), 6.12; (dd, J=14.7, 10.6 Hz, 1H), 6.04; (dd, J=14.9, 10.5, 1H), 5.66; (dq, J=13.7, 6.7 Hz, 1H), 5.49; (dt, J=14.8, 7.5 Hz, 1H), 4.44; (m, 2H-overlap), 4.33; (m, 3H-overlap), 4.25; (q, 1H), 4.14; (q, 1H), 4.09; (q, 1H), 3.70; (m, 1H), 3.56; (m, 1H), 3.19; (dd, J=7.6, 2.6 Hz, 2H), 2.92; (d, 1H), 2.75; (m, 2H), 2.70; (m, 2H), 2.55; (d, 1H), 2.01; (dt, 1H), 1.91; (m, 3H-overlap), 1.85; (s, 3H), 1.81; (m, 2H-overlap), 1.71; (d, 3H), 1.66; (m, 1H), 1.51; (m, 3H-overlap), 1.27; (m, 2H), 1.19; (t, 6H-overlap), 0.91; (d, 3H), 0.86; (d, 3H), 0.75; (d, 6H).

4a (Ac-CHexAVPAVYKMal—endo adduct stereochemistry)—1H-NMR (600 MHz, DMSO-$d_6$) δ9.14; (s, 1H), 8.58; (d, J=8.1 Hz, 1H), 8.17; (d, J=8.2 Hz, 1H), 8.03; (t, J=5.6 Hz, 1H), 7.91; (d, J=7.2 Hz, 1H), 7.84; (d, J=6.9 Hz, 1H), 7.79; (d, J=8.6 Hz, 1H), 7.46; (d, J=8.9 Hz, 1H), 7.22; (d, J=8.46 Hz, 1H), 7.04; (d, J=8.5 Hz, 2H), 6.97; (s, 1H), 6.90; (s, 1H), 6.63; (d, J=8.4 Hz, 2H), 5.77; (dt, J=9.1, 3.1, 2.9 Hz, 1H), 5.66; (dt, J=9.1, 3.1, 3.0 Hz, 1H), 4.40; (m, 1H), 4.35; (m, 2H-overlap), 4.30; (dd, 1H), 4.2; (m, 2H-overlap), 4.14; (m, 2H-overlap), 3.87; (d, J=6.7 Hz, 2H), 3.63; (m, 1H), 3.55 (m, 1H), 3.07; (m, 3H-overlap), 2.99; (m, 2H-overlap), 2.90-2.85; (m, 2H-overlap), 2.70-2.63; (m, 3H-overlap), (2.47-overlapped by DMSO signal), 2.08-1.96; (m, 4H-overlap), 1.95; (m, 1H), 1.84; (s, 4H-overlap), 1.66; (m, 1H), 1.46; (m, 2H-overlap), 1.32-1.23; (m, 8H-overlap), 1.18; (m, 1H), 1.09; (d, 3H), 0.96; (d, 3H), 0.88; (d, 3H), 0.75; (d, 3H), 0.70; (d, 3H).

EXAMPLE 2

This Example demonstrates that Diels-Alder cyclization is compatible with, and aids in, intramolecular disulfide stabilization.

Atrial natriuretic peptide (ANP) is a peptide hormone released by cardiac atrial cells to respond to modulate sodium levels and blood volume. ANP has low pharmacologic stability that has limited its use. Recent evidence suggests it may be of clinical use to dampen cytokine release syndrome during CAR-T treatment of cancers.

ANP Sequence and Potential DAC Designs:

```
ANP-WT:
                                             (SEQ ID NO: 6)
SCFGGRMDRIGAQSGLGCNSF,
which can be acetylated on the N-terminal serine DAC-ANP:
                                             (SEQ ID NO: 7)
SCFGGRX₁DRIGAQX₂GLGCNSF,
which can be acetylated on the N-terminal serine
X₁/X₂ = K(mal)/K(acr)/K(cpd) . . . (dienophile)
C(hex)/S(hex)/C(cpd)/A(fur) . . . (diene)
```

Figure 23C:
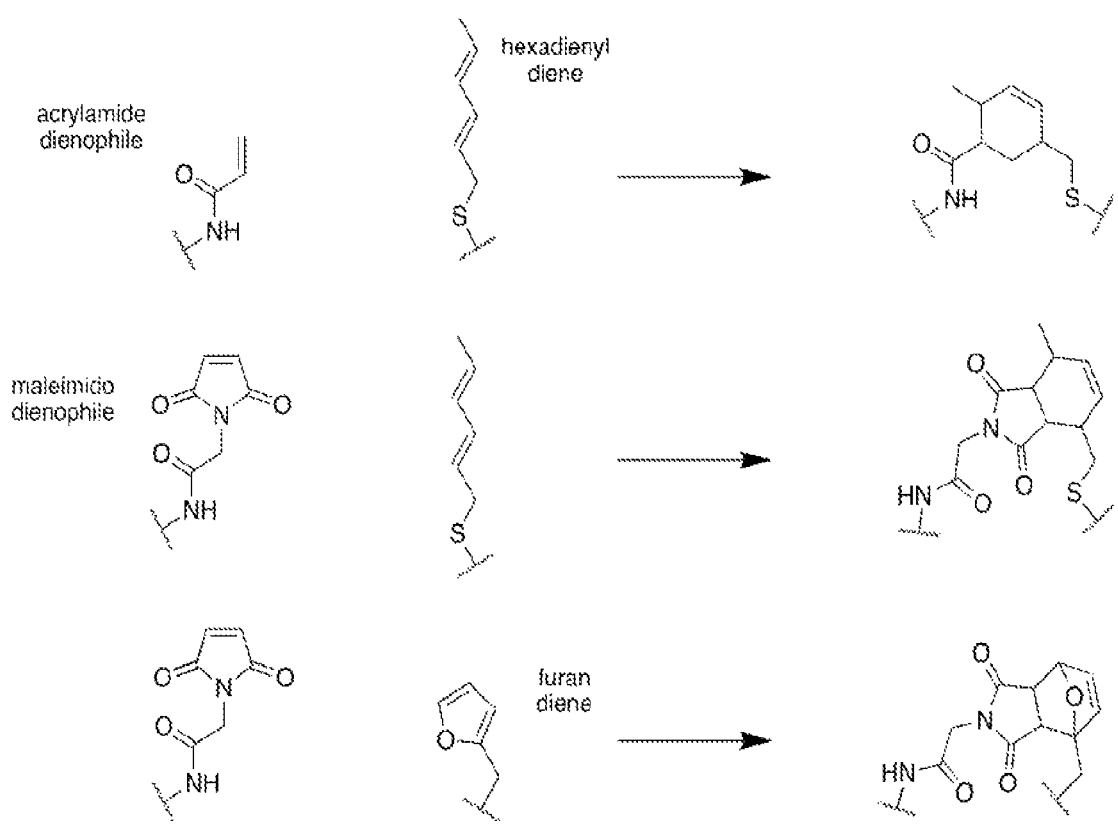
FIGS. 23C-23E Synthesized DAC peptide crosslink structures.
Figure 23D:
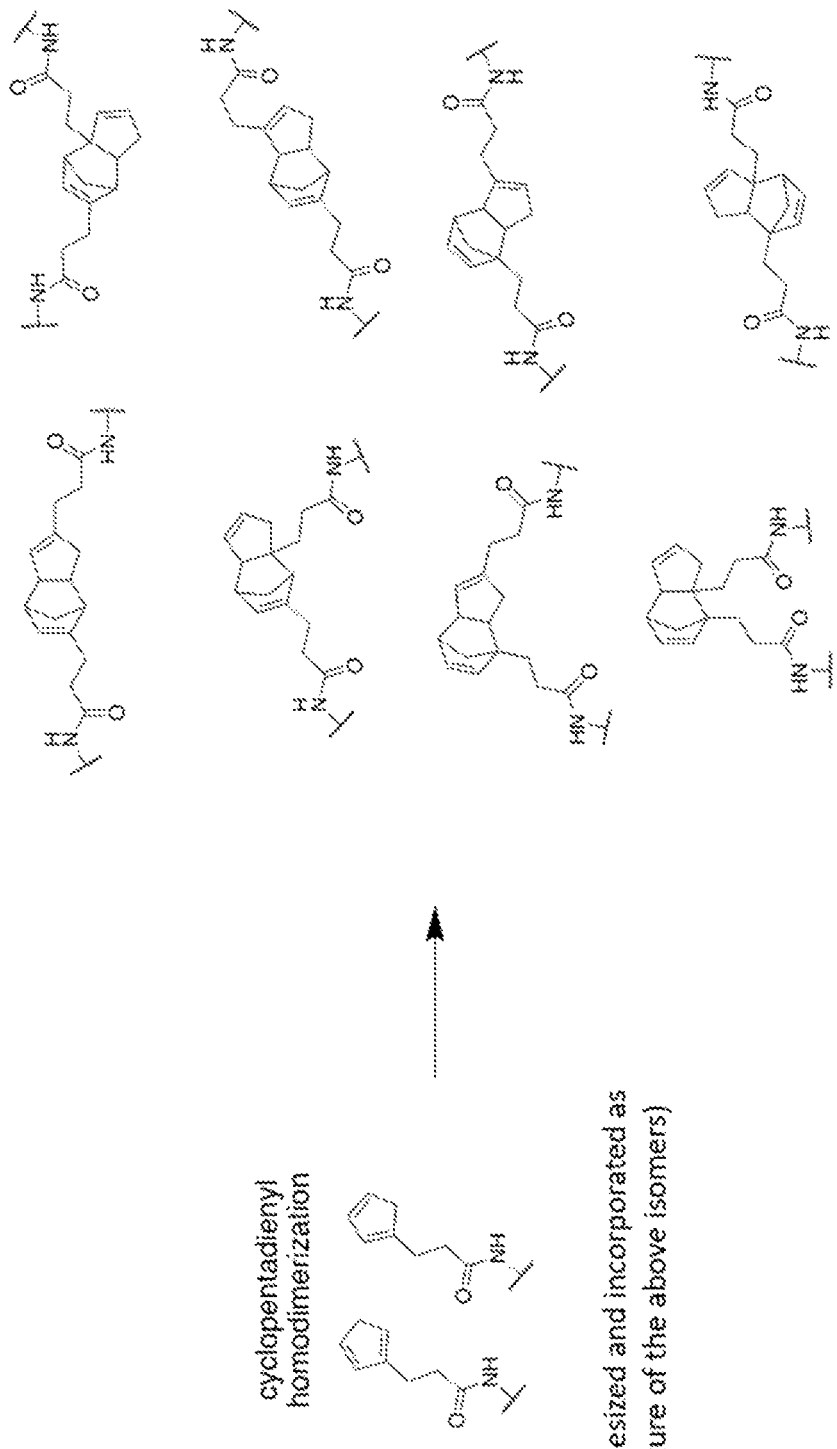
Figure 23E:
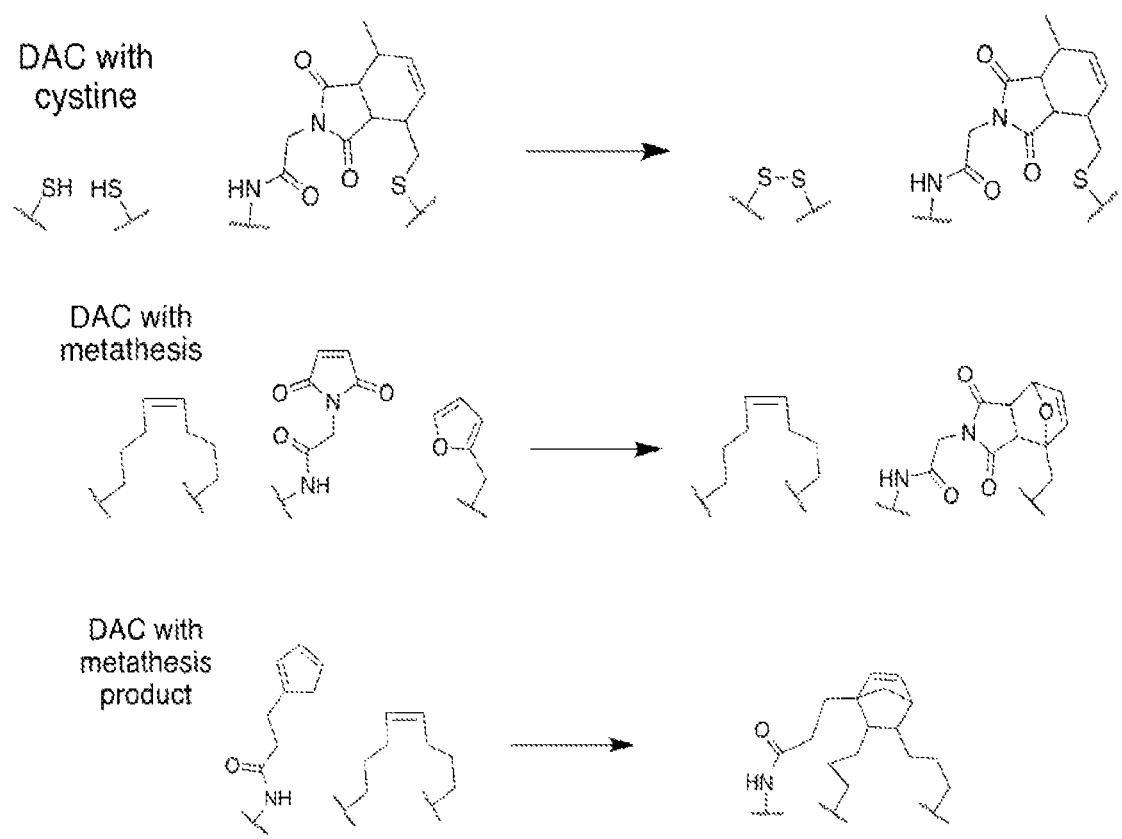
Figure 26A:
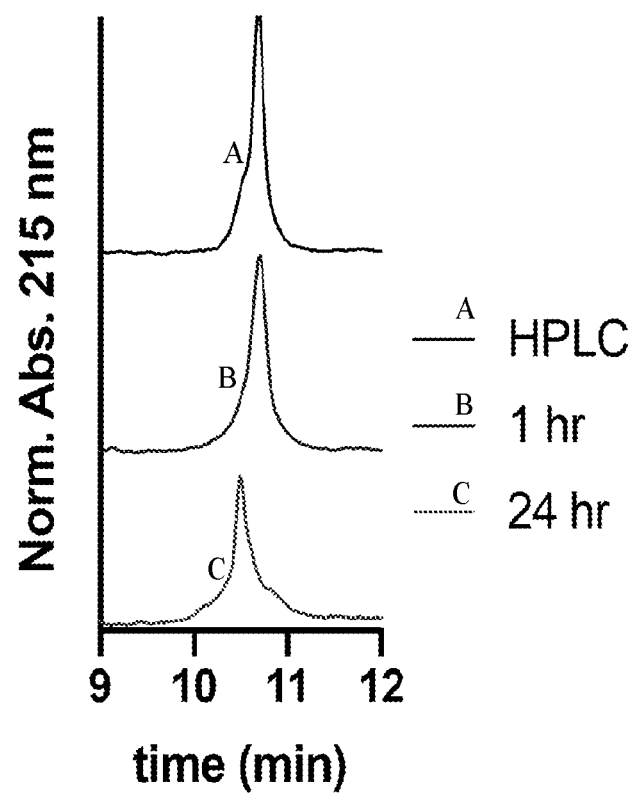
Figure 26B:
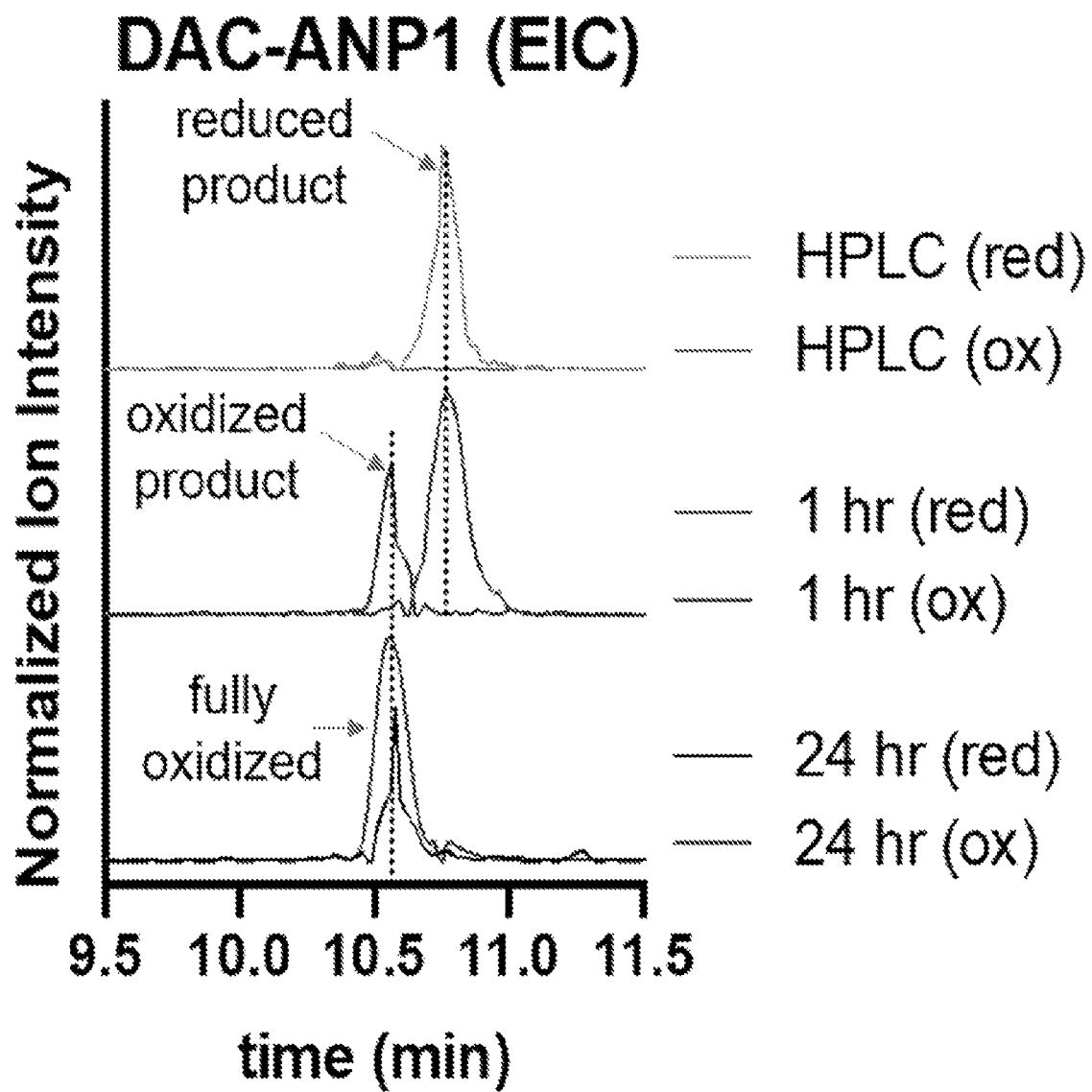

FIGS. 23A and 23B show representative amino acid side chains, N-termini, or C-termini functionalized with dienes and dienophiles. Some or all may be incorporated in-line with solid-phase peptide synthesis or after selective deprotection of nucleophilic amino acid side chains. Additionally, the disulfide bond(s) in ANP (as for other hormones or other peptides) could be replaced with Diels-Alder pairs. FIGS. 23C-23E present additional DAC crosslink structures.

Synthesis of DAC-ANP-1. The initial peptide was made by solid-phase peptide synthesis with incorporation of a Mmt-protected lysine and a 2,4-hexadiene functionalized cysteine: Cys(hex). Following Mmt-deprotection (1% TFA/DCM) and resin washing, 4 equivalents of glycyl-maleimide, 4 equivalents of HCTU, and 4 equivalents of DIPEA were added to the resin and bubbled under nitrogen gas for 15 min. Following heating in DMSO to promote the Diels-Alder reaction, the peptide was cleaved from the resin and the DAC reduced peptide was HPLC purified for subsequent oxidation. The final peptide was Ac-SCFGGRK(mal)DRI-GAQC(hex)GLGCNSF (SEQ ID NO: 8). See FIG. 24.

Diels-Alder cyclization of DAC-ANP1, containing K(mal) and C(hex), occurred rapidly on resin, yielding a major isolable cyclic species: DAC-ANP1 (reduced); >55% crude yield as determined by LC-MS. The purified DAC peptide was templated for rapid disulfide formation in <24 hr at room temperature; quantitative yield, as determined by LC-MS. Incubation of the HPLC-purified DAC-ANP1 (reduced) in 0.1 M ammonium acetate, 5% DMSO, pH 7.6, at room temperature resulted in complete conversion to the oxidized product observed by a retention time shift and loss of 2 Da by LCMS (major reduced ion: 1217.8; major oxidized ion: 1216.9). See FIGS. 25 and 26A-26C.

Synthesis of ANP-WT. The wildtype peptide ANP-WT was synthesized using standard solid-phase peptide synthesis, deprotected and cleaved off resin, and HPLC purified for subsequent in solution oxidation. See FIG. 27.

Figure 28A:
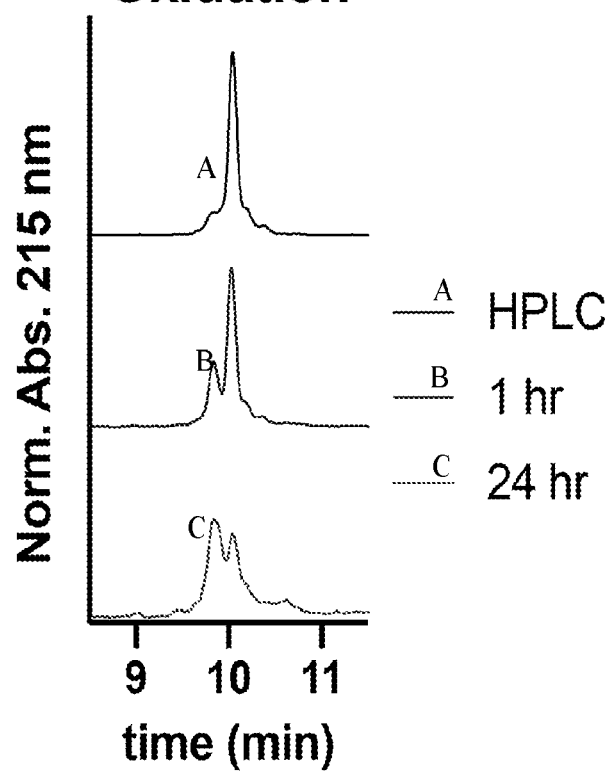
FIGS. 28A-28C FIG. 28A HPLC plots of ANP-WT.
Figure 28B:
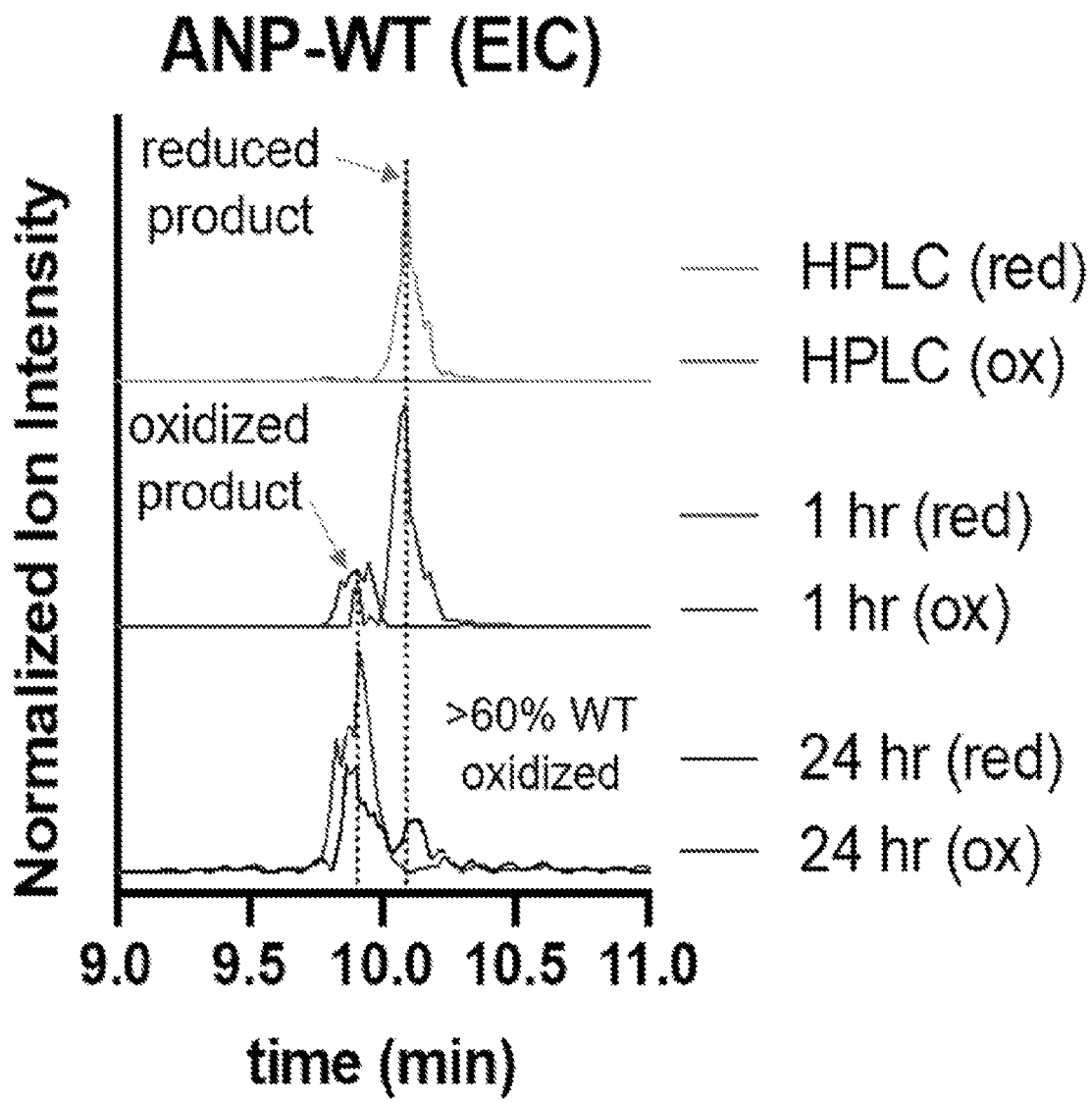
Figure 28C:
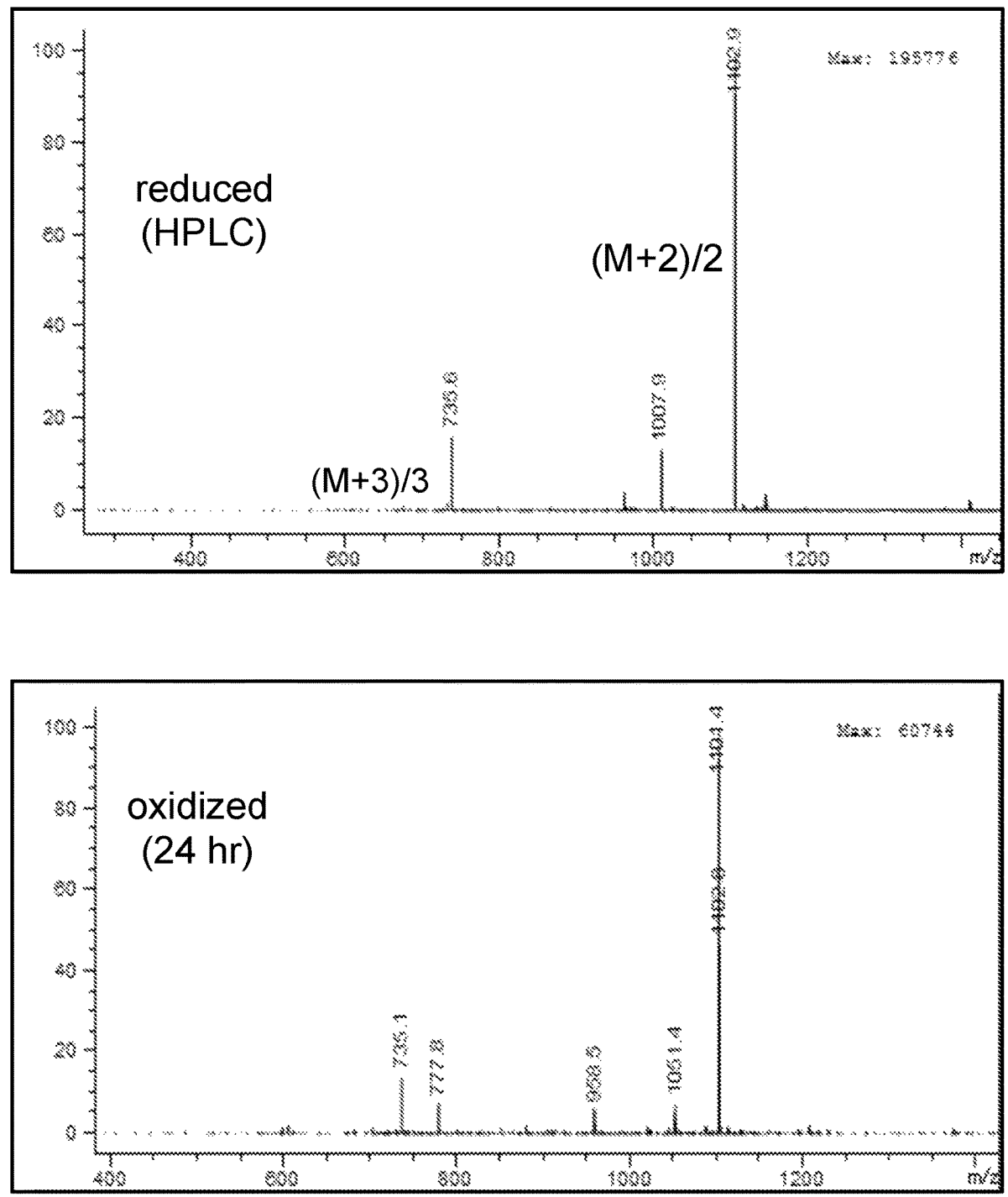

In contrast to DAC-ANP-1, under the oxidation conditions used here (incubation at 0.1 M ammonium acetate, 5% DMSO, pH 7.6, at room temperature), the purified ANP-WT peptide was not completely oxidized within 24 hr (major reduced ion: 1102.9; major oxidized ion: 1101.4). A small amount of reduced starting material remained and apparent side reactions of intermolecular disulfide formation and likely methionine oxidation were found to occur. See FIGS. 28A-28C. Increased dilution or alternative oxidation conditions may help increase product yield.

Diels-Alder cyclizations can be used to replace, augment and template intramolecular disulfide bond cyclization. Diels-Alder cyclization of atrial natriuretic peptide (ANP) templates the peptide for rapid and high-yielding disulfide formation and can be applied to template multiple disulfide bonds in parallel. This may enhance activity and proteolytic stability (ANP-WT has a circulating half-life of <5 min).

EXAMPLE 3

This Example demonstrates synthesis of Lys(cpd).

Figure 29:
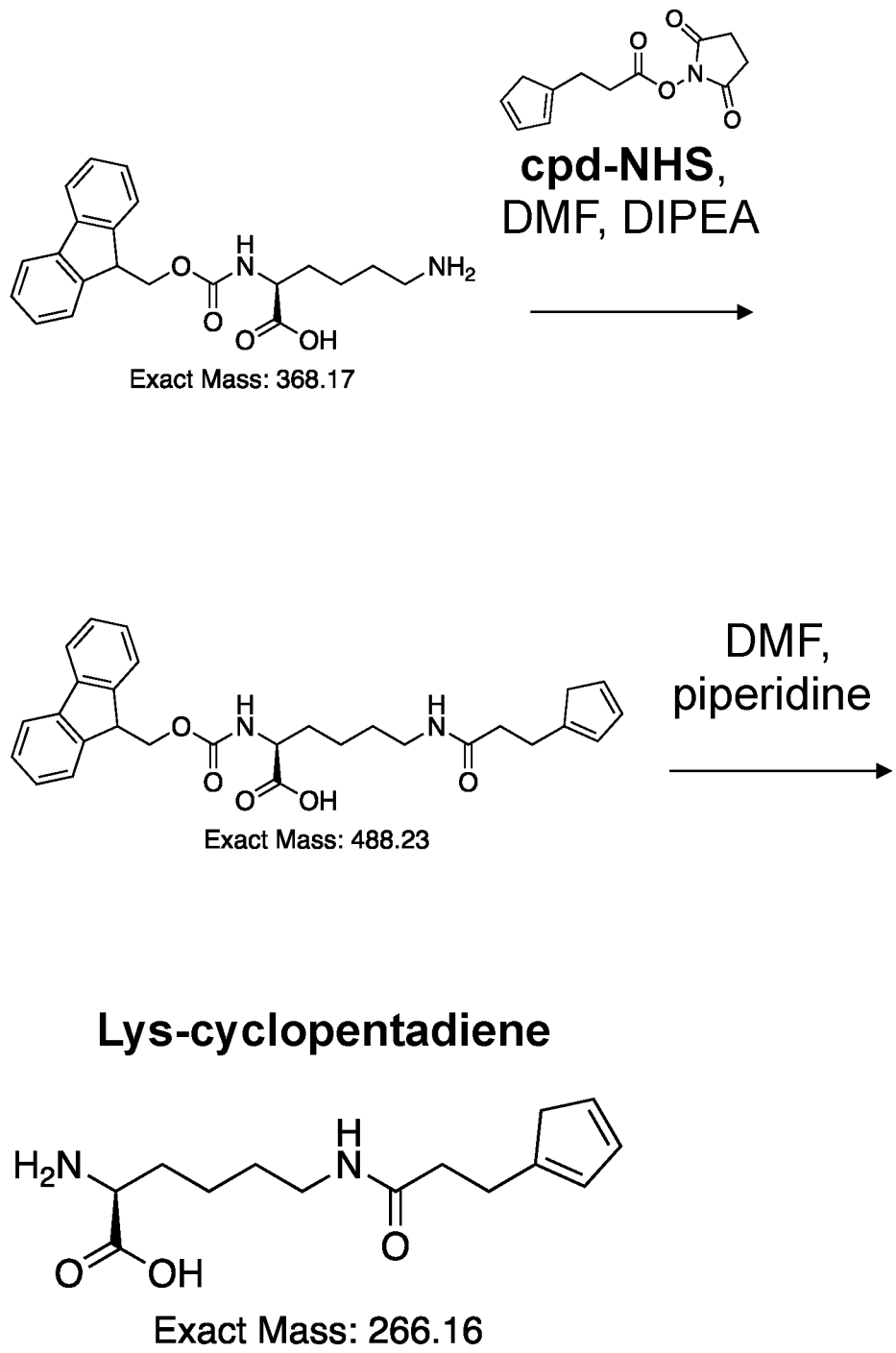
FIG. 29 Synthetic scheme for Lys-cyclopentadiene.
Figure 30:
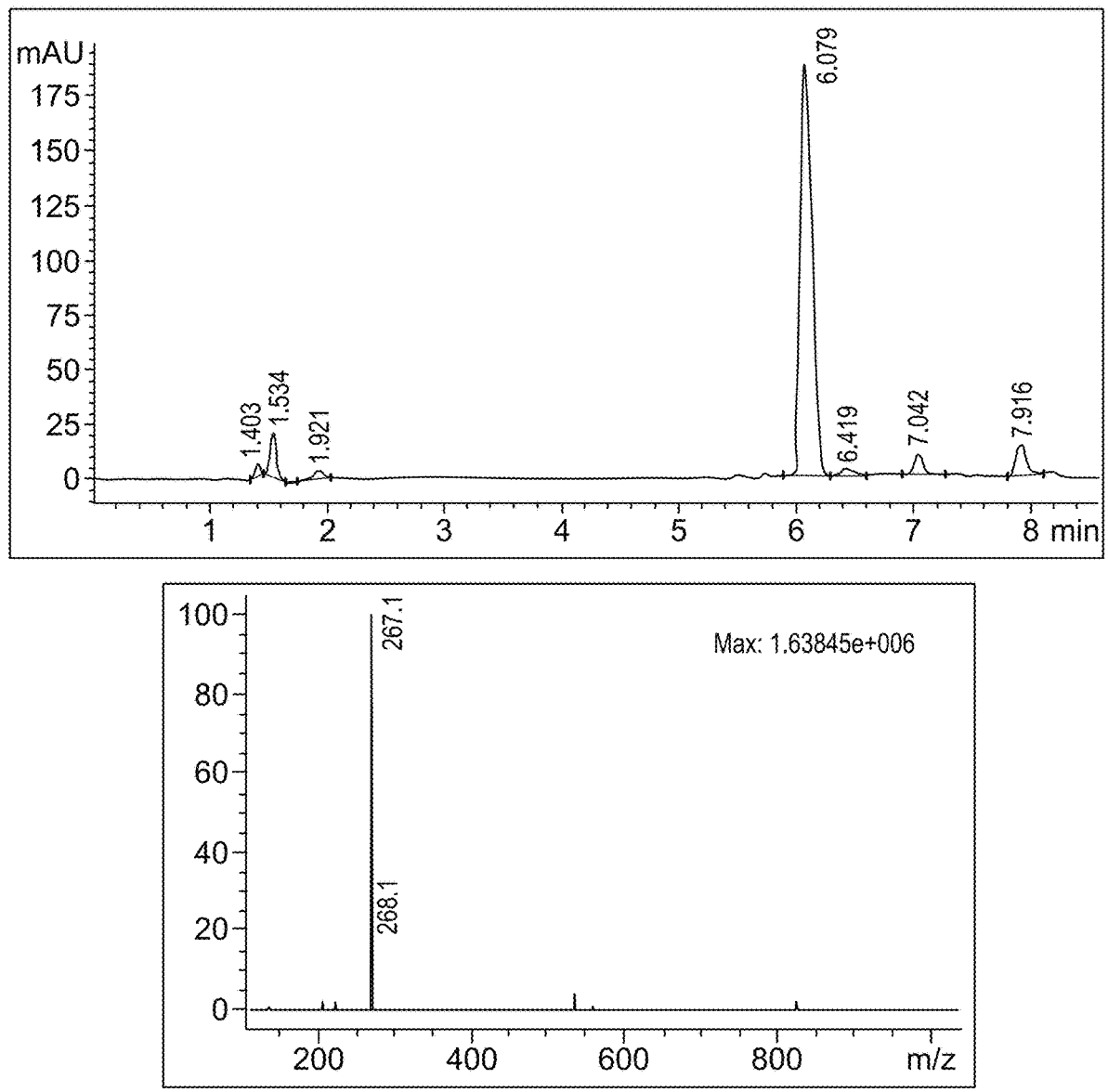
FIG. 30 LCMS chromatogram and trace for free Lysine-cyclopentadiene containing free amino acid.

A cyclopentadiene containing lysine amino acid was synthesized by acylating a protected lysine with 1.5 equivalents of a cyclopentadiene NETS ester with 1 equivalent of DIPEA, and then deprotection of the Fmoc group with 25% piperidine in DMF. See FIGS. 29 and 30.

EXAMPLE 4

This Example demonstrates Diels-Alder peptide dimerization.

To investigate the use of Diels-Alder chemistry on larger protein structures, including those with stabilized secondary and tertiary domains, homodimer-mimetics of the Max/Max transcription factor complex was targeted.

Following solid-phase peptide synthesis of a MaxWT sequence and synthetic DNA binding domain RTD8 (and ring-closing metathesis peptide stapling of RTD8), Mmt-lysine was deprotected with 1% TFA. Selective acylation of the free lysine by the cyclopentadiene (cpd) NETS-ester was then achieved on-resin by bubbling 5 equivalents in NMP (1-2×, 2 hr).

Following cleavage from resin, subsequent heating in concentrated DMSO stocks (~5 mM) resulted in rapid formation of DA-ligated dimeric complexes as detected by LCMS.

Sequences are shown below for precursor and cpd-containing peptides (*=S5; b=beta-Ala).

```
MaxWT:
                                  (SEQ ID NO: 9)
KRAHHNALERKRRDHIKDSFHbK(Mmt)W

RTD8:
                                  (SEQ ID NO: 10)
KR*HHN*LERKRRDHIKDSbK(Mmt)

MaxWT-cpd:
                                  (SEQ ID NO: 11)
KRAHHNALERKRRDHIKDSFHbK(cpd)W RTD8-cpd:
                                  (SEQ ID NO: 12)
KR*HHN*LERKRRDHIKDSbK(cpd)
```

Figure 31:
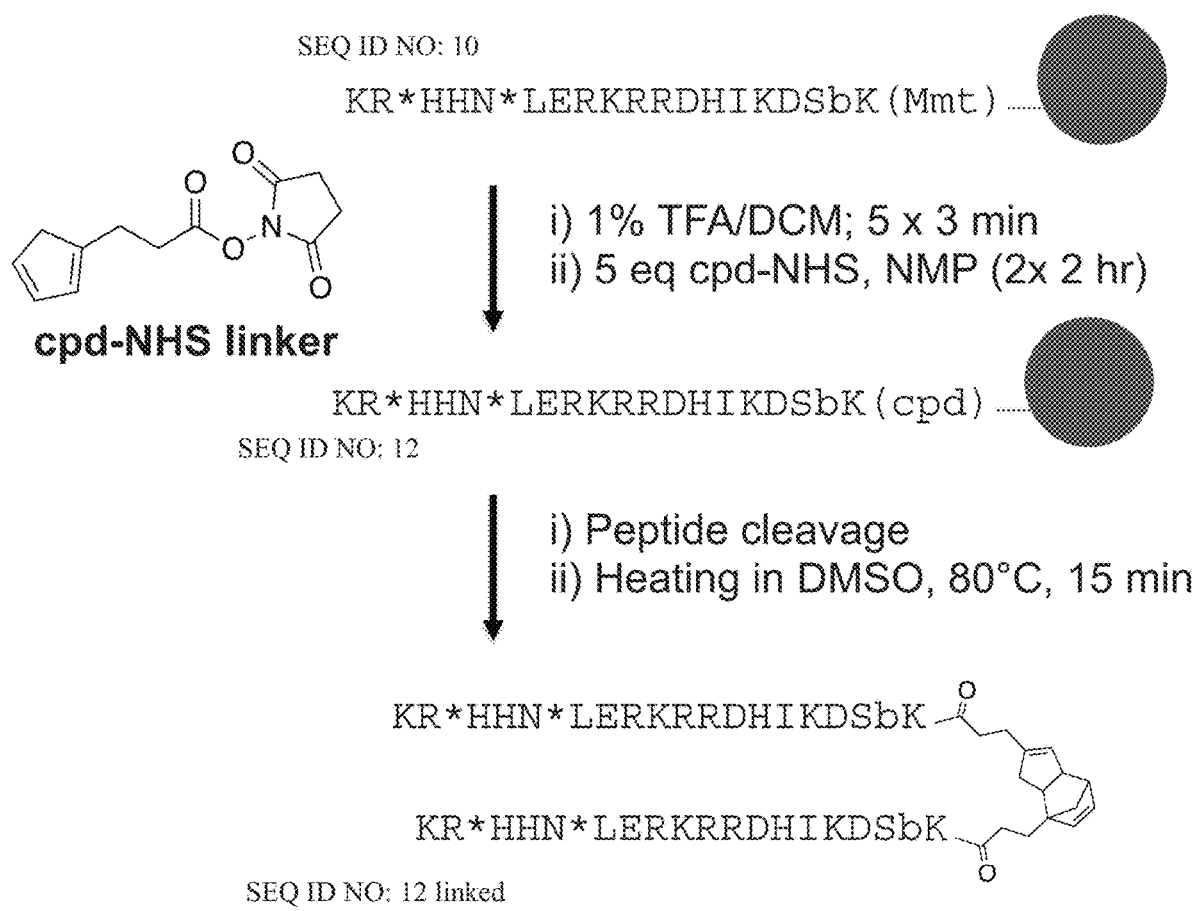
FIG. 31 RTD8-dimer synthetic scheme.
Figure 33A:
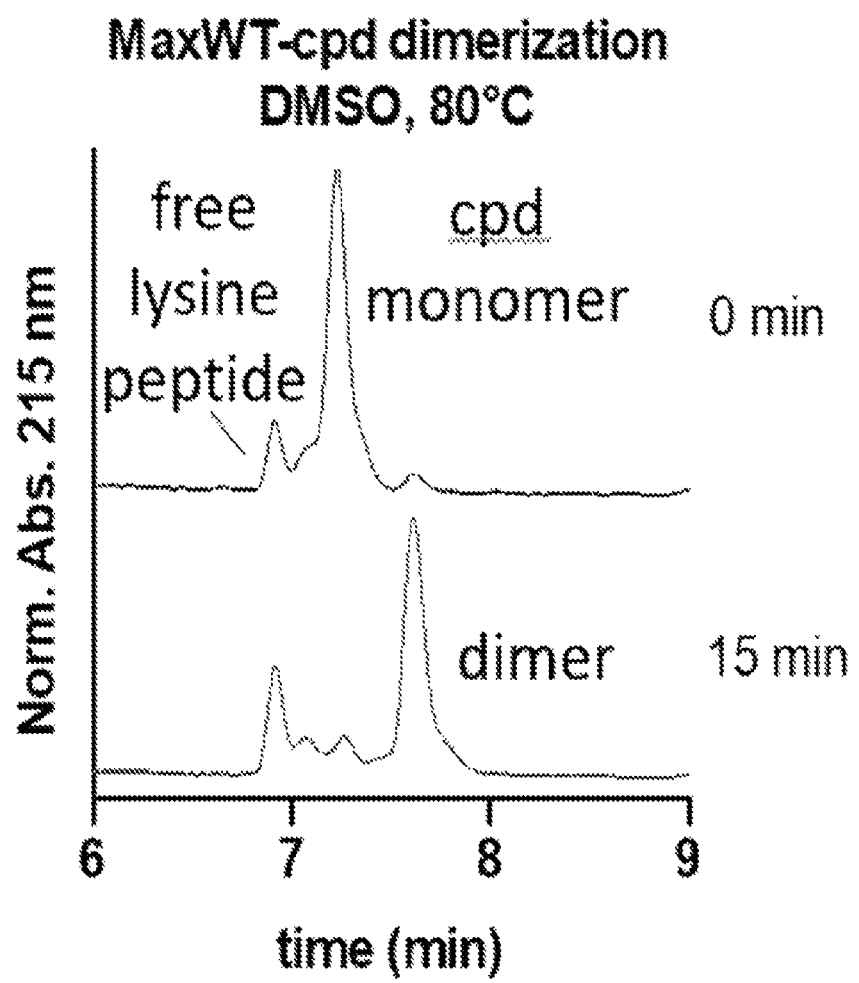
FIGS. 33A-33F FIG. 33A HPLC plots of Max-WT-cpd.
Figure 33B:
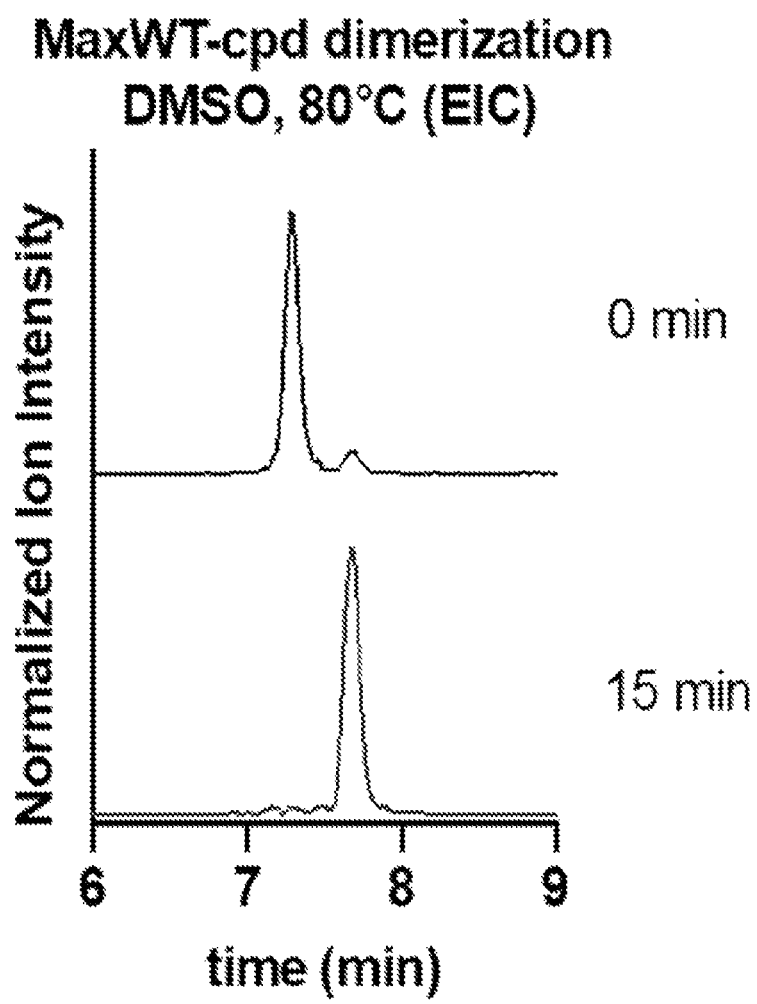
Figure 33C:
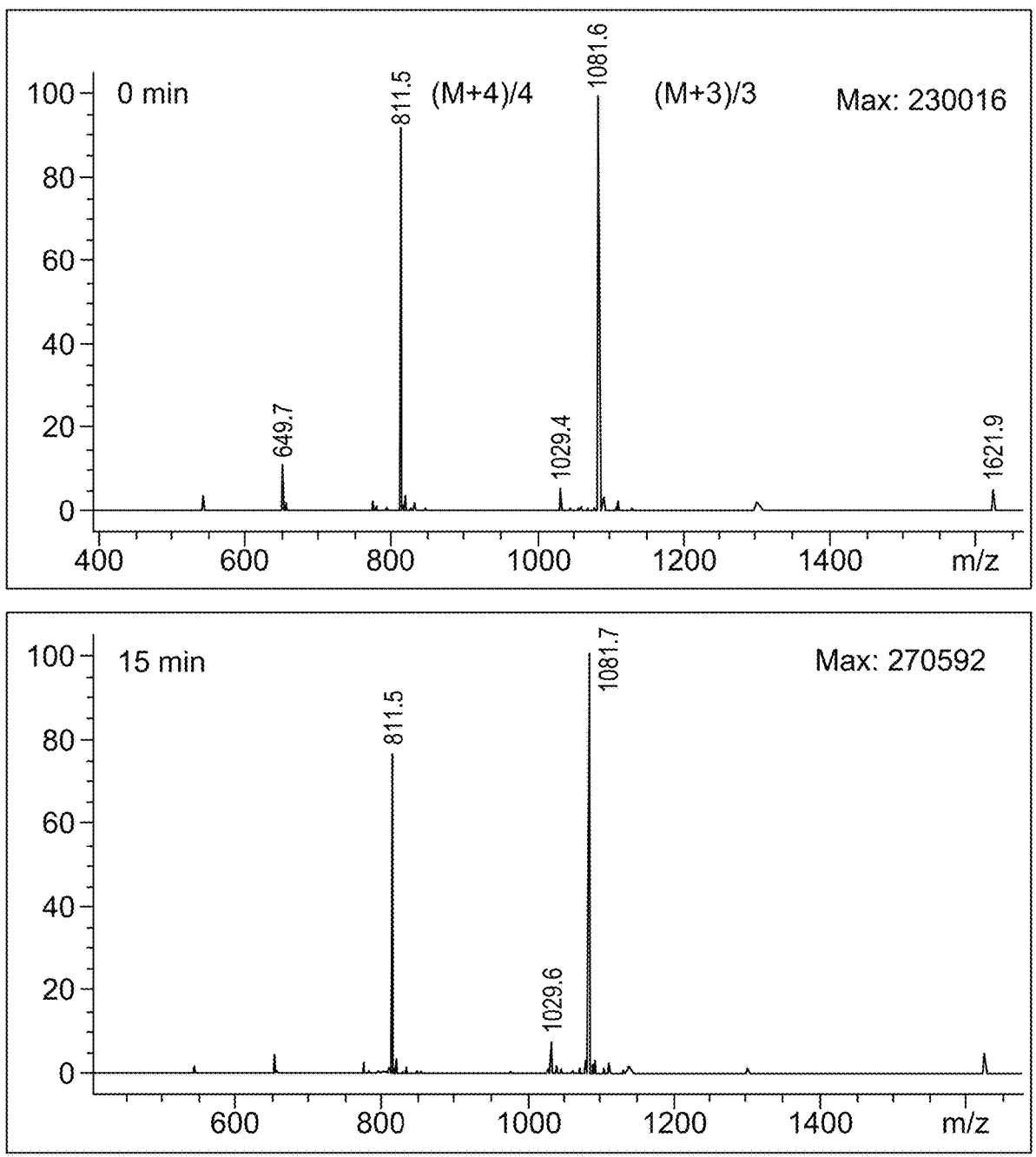
Figure 33D:
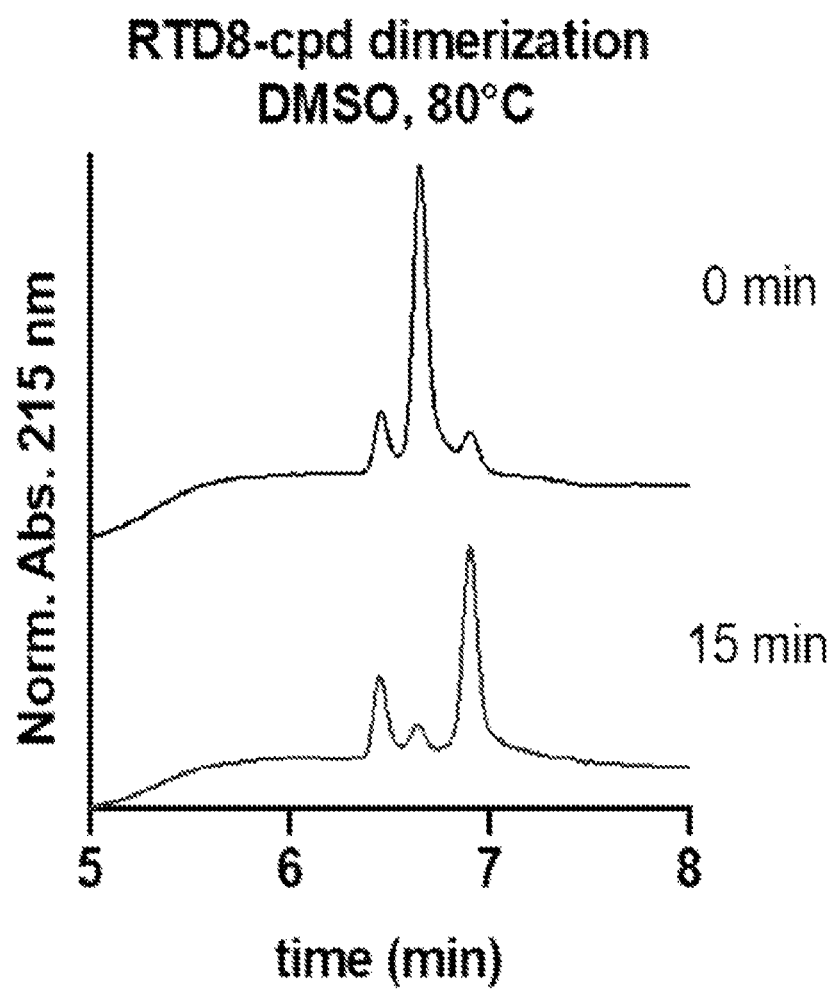
Figure 33E:
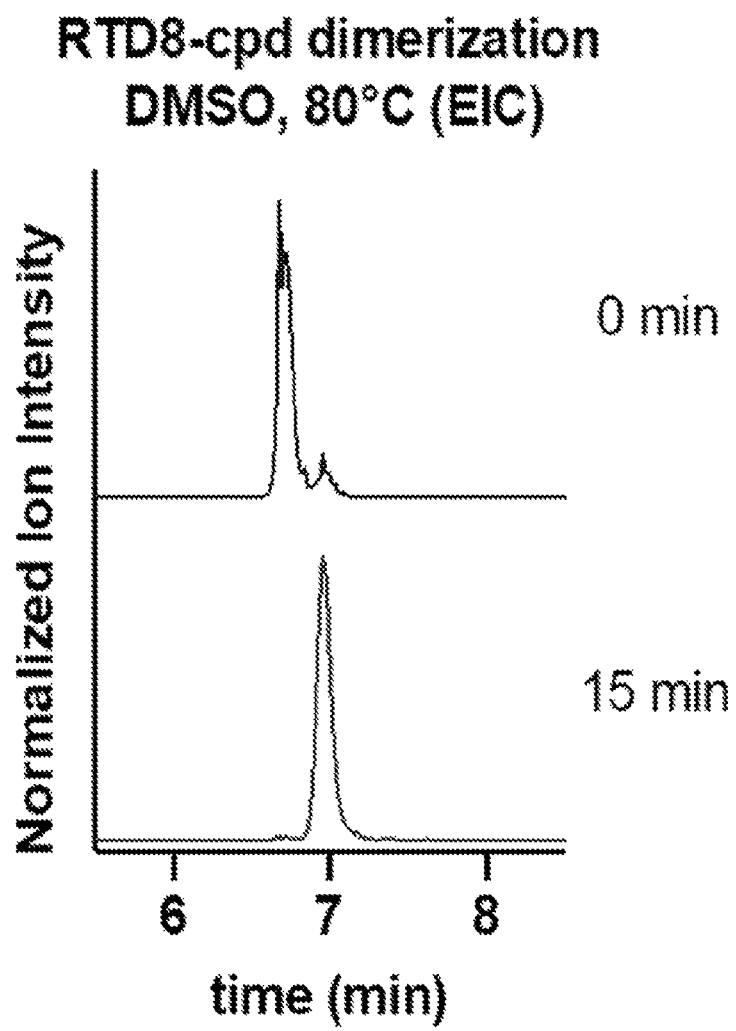
Figure 33F:
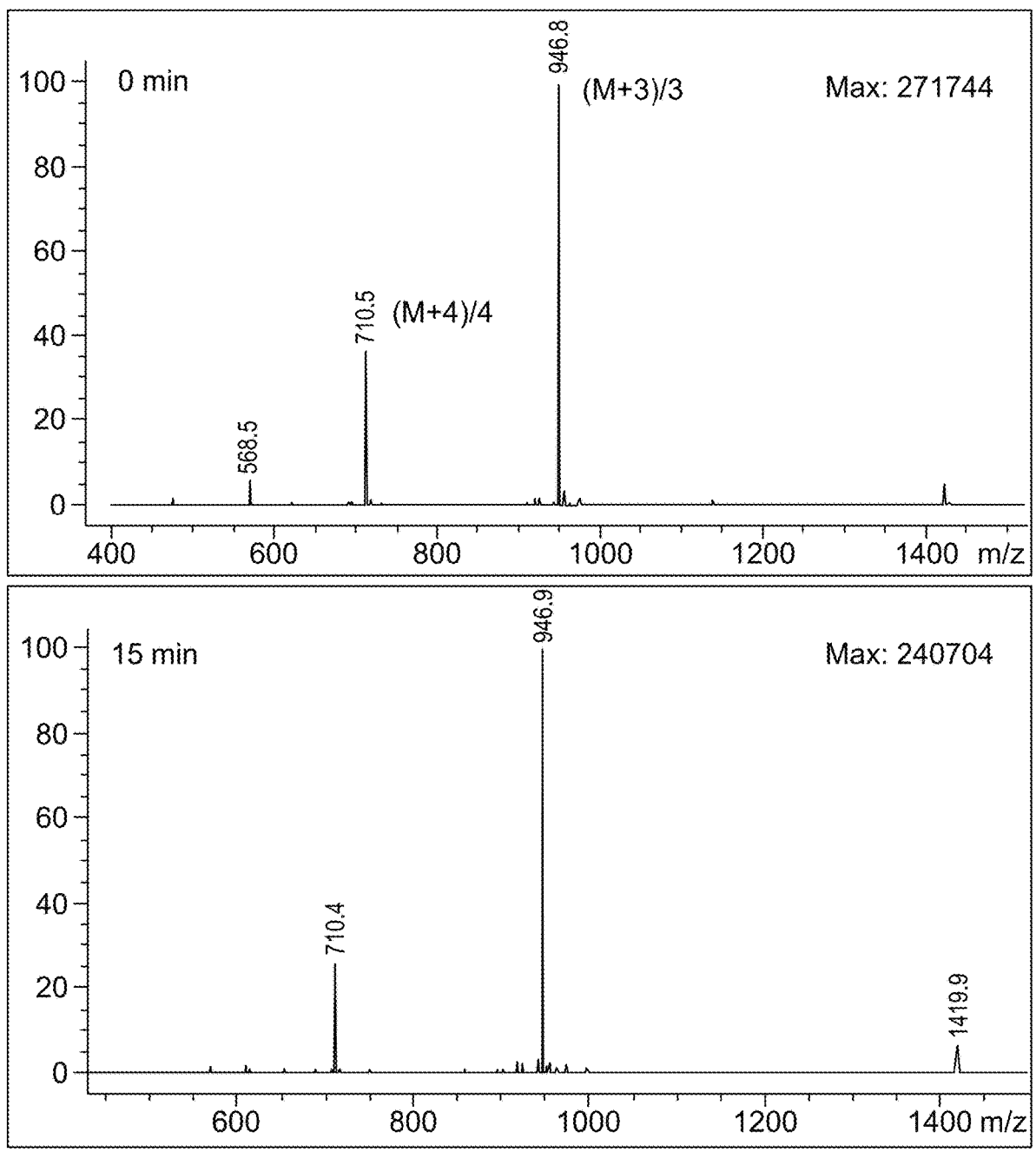

RTD8-dimer synthetic scheme and structures are shown in FIGS. 31 and 32. See FIGS. 33A-33F for experimental results.

EXAMPLE 5

This Example demonstrates Diels-Alder reaction between a cyclopentadiene and a ring-closing metathesis staple.

To assess the ability of cyclopentadiene to react with the strained alkene generated by ring-closing metathesis peptide stapling, incorporation of cpd in close proximity to the staple cross-link of StAx32.5R (an optimized analog of a beta-catenin-targeting peptide) was tested.

Following standard solid-phase peptide synthesis with incorporation of 2 bis-alkylated pentenyl-containing amino acids (S5, *), Grubbs I catalyst was used for ring-closing metathesis, generating the staple cross-link.

Figure 35:
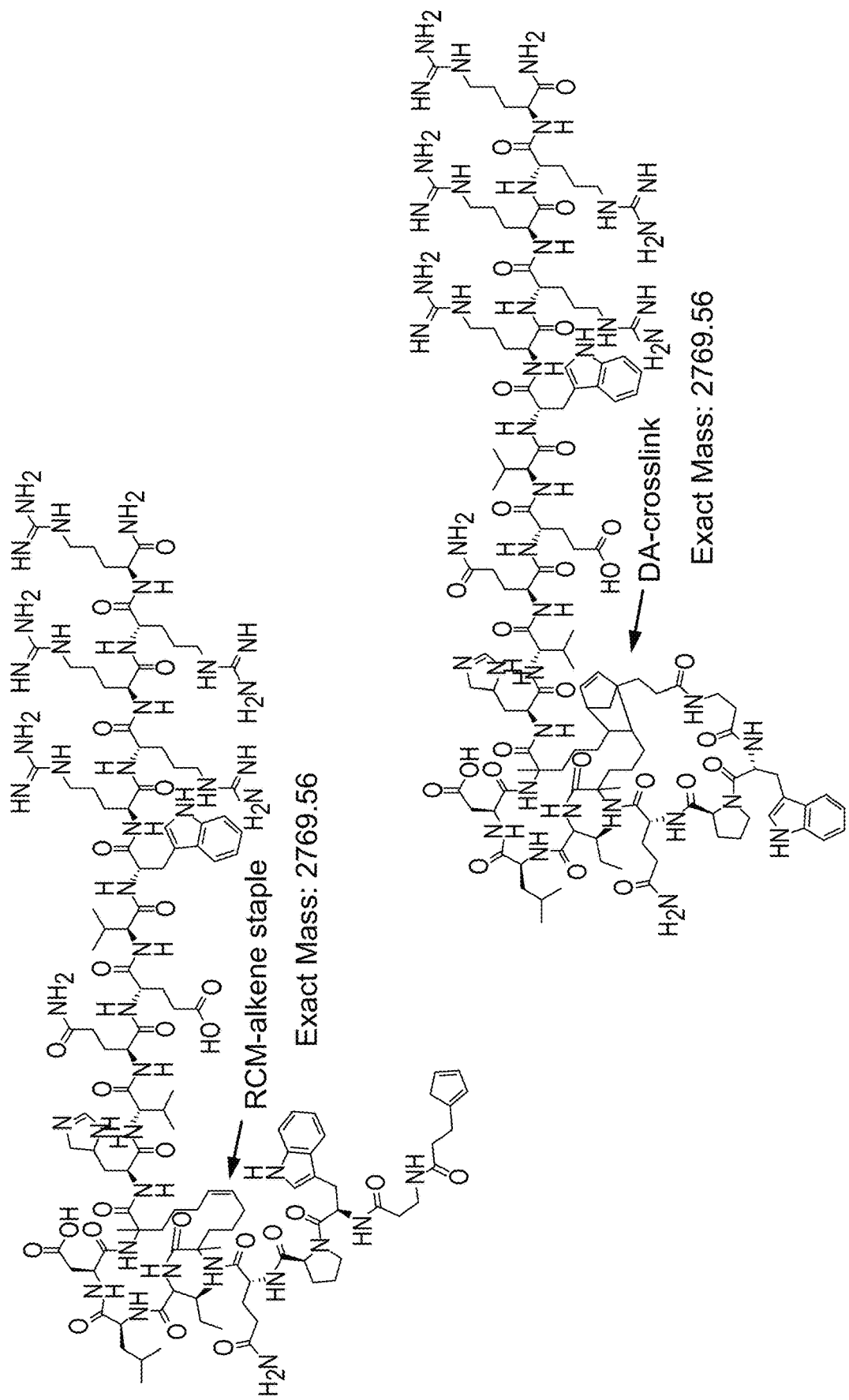
FIG. 35 Chemical structures for cpd-StAx32.5R and DA-crosslinked StAx32.5R.

Sequences and synthetic scheme (FIG. 34) are shown for Fmoc-protected precursor peptides (unstapled and stapled) and cpd-containing peptides (*=S5; β=beta-Ala) for StAx32.5R (FIG. 35).

Figure 36:
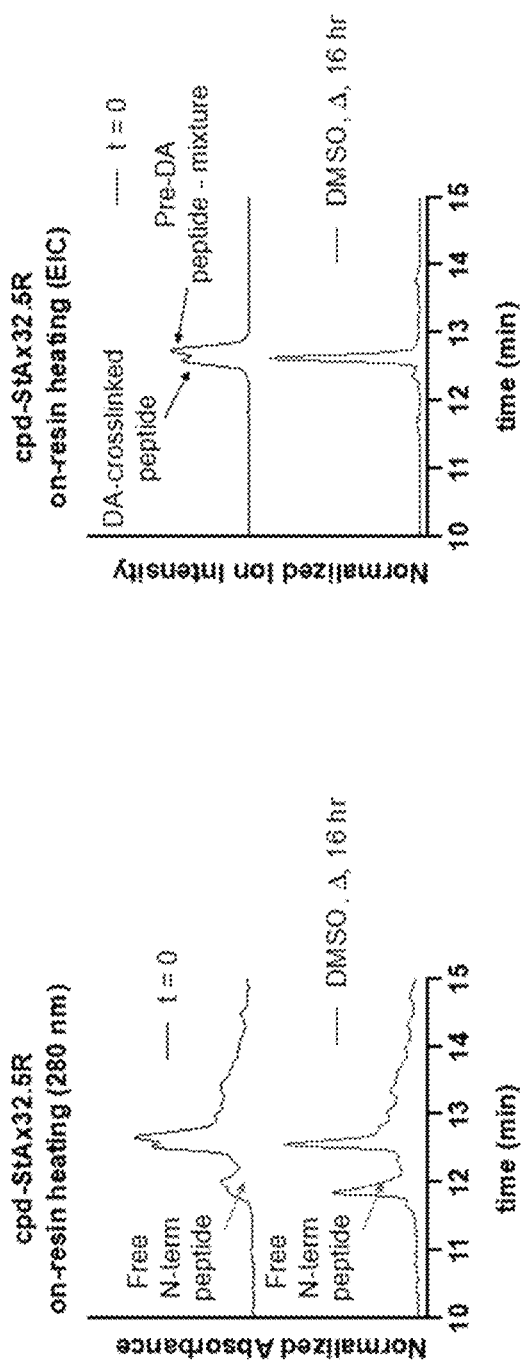
FIG. 36 LCMS analysis of cpd-StAx32.5R, before and after on-resin heating in DMSO.

Following Fmoc-deprotection and incorporation of cyclopentadiene on the N-terminus of the peptide, 2 peaks with m/z corresponding to the expected molecular weight were observed. Following on-resin incubation in DMSO at 45° C. for 16 hr, only one, earlier eluting peak was observed; free-N-terminal starting material was also generated. See FIG. 36.

EXAMPLE 6

This Example demonstrates noncanonical amino acid (ncAA) incorporation of Diels-Alder compatible amino acids for DAC proteins and DA-oligomerized proteins.

Cyclopentadiene lysine amino acid (cpdLys or Lys(cpd)) is sufficiently similar to the naturally occurring amino acid pyrrolysine to be used by native and engineered variants of pyrrolysine RNA synthetase (PylRS). This enzyme will charge tRNA molecules with the amino acid, allowing for its incorporation by ribosomes into proteins where a TAG amber stop codon is encoded. Thus, cpdLys, or other Diels-Alder compatible amino acids, may be inserted into any protein sequence in cell-free, phage, bacterial, or mammalian expression systems.

By encoding one TAG site into a protein, a single cpdLys can be inserted, allowing for conjugation or protein dimerization via Diels-Alder chemistry.

If two TAG sites are incorporated such that the resulting amino acids can be in close proximity, the protein may be selectively intramolecularly cross-linked via the Diels-Alder reaction.

The GTPase RAB25 is a small globular mammalian protein amenable to recombinant expression and folding in the E. coli BL21 expression system. When folded, the N- and C-termini of RAB25 are in close proximity. Two plasmids encoding RAB25 were prepared, one replacing a single N-terminal residue with a TAG site (1×TAG), and another replacing the same residue and a second C-terminal residue with a TAG site (2×TAG) (FIG. 37), both having polyhistidine tags. The incorporation of the TAG sites was confirmed by sequencing. Both plasmids were transformed into chemically competent BL21+chPylRS cells (kan/chlor res.) and inoculated overnight (LB+kan/chlor). A 100×-dilution of the inoculated culture was used for the expression culture (grown to $OD_{600}$=0.5). Induction with 1 mM IPTG was performed with 1 mM cpdLys, and the culture grown for 16 hr at 37° C. and 225 rpm. For harvesting the cells, the cells were pelleted (4000 g, 4° C., 5 min) and lysed in 500 μL PBS+protease inhibitors and using sonication (2 sec on 30% amplitude, 5 sec off, total 2 min). The lysate was clarified (17000 g, 4° C., 10 min). Ni-NTA enrichment was performed of the $His_6$-RAB25 protein using standard enrichment, washing and elution procedures. The results were analyzed by SDS-PAGE.

1×TAG and 2×TAG RAB25 proteins are observed at slightly higher and slightly lower apparent molecular weights, respectively. 1×TAG has a higher molecular weight due to ncAA incorporation. 2×TAG has an apparent lower weight due to changes in migration efficiency due to covalent crosslinking of the polypeptide chain.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All of the methods disclosed and claimed herein can be made and executed without undue experimentation in light of the present disclosure. Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of synthesizing a macrocyclic compound, the method comprising:

synthesizing a peptide of formula (II) comprising reactive functional groups Y and Z capable of undergoing a Y—Z conjugating reaction; and subjecting the peptide to conditions that drive the Y—Z conjugating reaction to form an intramolecular Y—Z crosslinking moiety;

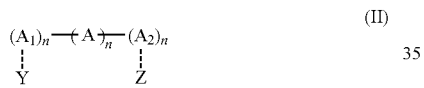

(II)

wherein

A, $A_1$, and $A_2$ are amino acids;

each n is independently an integer from 0 to 600, except where attached to Y or Z, wherein n is at least 1; and wherein Y and Z react to form an adduct selected from

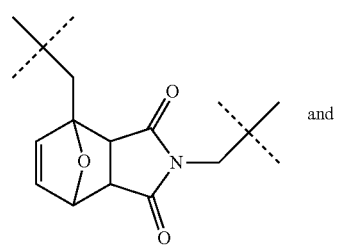

and

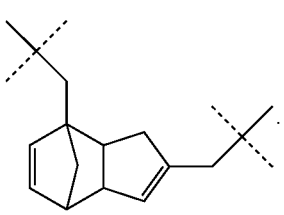

2. The method of claim 1, wherein each of Y and Z is independently bound to a side chain, amine group, carboxy group, or α-carbon of a different amino acid.

3. The method of claim 1, wherein the Y—Z conjugating reaction is a cycloaddition reaction.

4. The method of claim 1, wherein n for $A_1$ is 2 and n for $A_2$ is 2, wherein the first pair of Y and Z react to form an adduct selected from

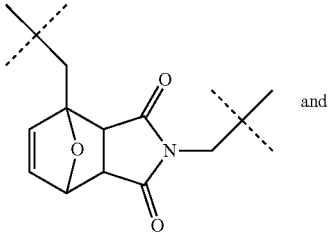

and

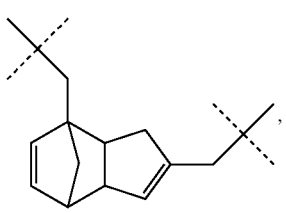

and wherein the second pair of Y and Z react to form an adduct resulting from a Diels-Alder reaction.

5. The method of claim 1 wherein n for A is at least 2 and at least one amino acid A is a non-natural amino acid.

6. The method of claim 1, wherein Y is a conjugated diene.

7. The method of claim 6, wherein the conjugated diene is part of a cyclic structure.

8. The method of claim 6, wherein the conjugated diene is furan or cyclopentadiene.

9. The method of claim 1, wherein Z is a dienophile.

10. The method of claim 1, wherein the peptide of formula (II) is further defined as one of
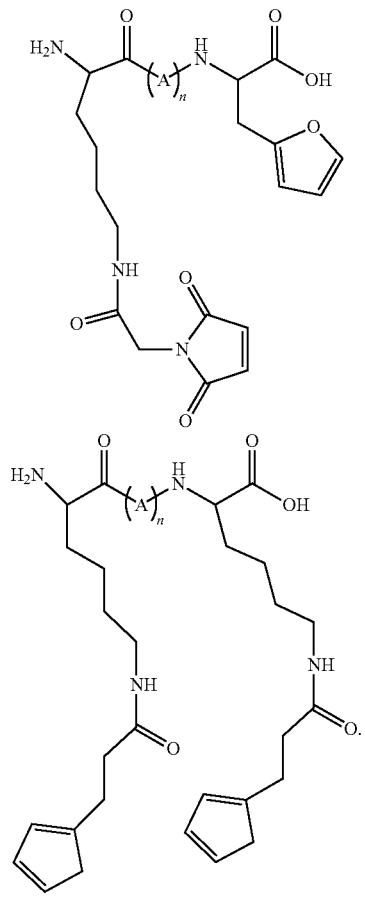
11. The method of claim 1, wherein Y and Z react to form an adduct of
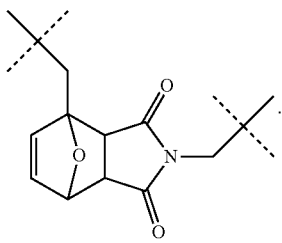
12. The method of claim 1, wherein Y and Z react to form an adduct of
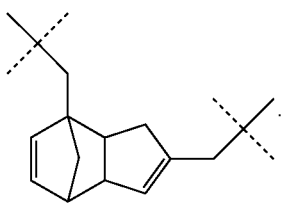
* * * * *

SEQUENCE LISTING

```
<160> NUMBER OF SEQ ID NOS: 37

<210> SEQ ID NO 1
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(hex)
<220> FEATURE:
<221> NAME/KEY: MISC_FEATURE
<222> LOCATION: (5)..(5)
<223> OTHER INFORMATION: Xaa is K(mal)

<400> SEQUENCE: 1

Xaa Arg Gly Asp Xaa
```

1               5

<210> SEQ ID NO 2
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(hex)
<220> FEATURE:
<221> NAME/KEY: MISC_FEATURE
<222> LOCATION: (5)..(5)
<223> OTHER INFORMATION: Xaa is K(mal)

<400> SEQUENCE: 2

Xaa Val Gly Asp Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(hex)
<220> FEATURE:
<221> NAME/KEY: MISC_FEATURE
<222> LOCATION: (6)..(6)
<223> OTHER INFORMATION: Xaa is K(mal)

<400> SEQUENCE: 3

Xaa Ala Pro Val Tyr Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(hex)
<220> FEATURE:
<221> NAME/KEY: MISC_FEATURE
<222> LOCATION: (8)..(8)
<223> OTHER INFORMATION: Xaa is K(mal)

<400> SEQUENCE: 4

Xaa Ala Val Pro Ala Val Tyr Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is any AA
<220> FEATURE:
<221> NAME/KEY: MISC_FEATURE
<222> LOCATION: (3)..(3)

```
<223> OTHER INFORMATION: Xaa is any AA

<400> SEQUENCE: 5

Leu Xaa Xaa Leu Leu
1               5

<210> SEQ ID NO 6
<211> LENGTH: 21
<212> TYPE: PRT
<213> ORGANISM: Artificial Sequence
<220> FEATURE:
<223> OTHER INFORMATION: synthetic

<400> SEQUENCE: 6

Ser Cys Phe Gly Gly Arg Met Asp Arg Ile Gly Ala Gln Ser Gly Leu
1               5                   10                  15

Gly Cys Asn Ser Phe
            20

<210> SEQ ID NO 7
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is AA with dienophile
<220> FEATURE:
<221> NAME/KEY: MISC_FEATURE
<222> LOCATION: (14)..(14)
<223> OTHER INFORMATION: Xaa is AA with diene

<400> SEQUENCE: 7

Ser Cys Phe Gly Gly Arg Xaa Asp Arg Ile Gly Ala Gln Xaa Gly Leu
1               5                   10                  15

Gly Cys Asn Ser Phe
            20

<210> SEQ ID NO 8
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is C(hex)
<220> FEATURE:
<221> NAME/KEY: MISC_FEATURE
<222> LOCATION: (14)..(14)
<223> OTHER INFORMATION: Xaa is K(mal)

<400> SEQUENCE: 8

Ser Cys Phe Gly Gly Arg Xaa Asp Arg Ile Gly Ala Gln Xaa Gly Leu
1               5                   10                  15

Gly Cys Asn Ser Phe
            20

<210> SEQ ID NO 9
<211> LENGTH: 24
<212> TYPE: PRT
<213> ORGANISM: Artificial Sequence
<220> FEATURE:
<223> OTHER INFORMATION: synthetic
<220> FEATURE:
```

```
<221> NAME/KEY: MISC_FEATURE
<222> LOCATION: (22)..(22)
<223> OTHER INFORMATION: Xaa is beta-alanine
<220> FEATURE:
<221> NAME/KEY: MISC_FEATURE
<222> LOCATION: (23)..(23)
<223> OTHER INFORMATION: Xaa is K(mmt)

<400> SEQUENCE: 9

Lys Arg Ala His His Asn Ala Leu Glu Arg Lys Arg Arg Asp His Ile
1               5                   10                  15

Lys Asp Ser Phe His Xaa Xaa Trp
            20

<210> SEQ ID NO 10
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is S5
<220> FEATURE:
<221> NAME/KEY: MISC_FEATURE
<222> LOCATION: (7)..(7)
<223> OTHER INFORMATION: Xaa is S5
<220> FEATURE:
<221> NAME/KEY: MISC_FEATURE
<222> LOCATION: (20)..(20)
<223> OTHER INFORMATION: Xaa is beta-alanine
<220> FEATURE:
<221> NAME/KEY: MISC_FEATURE
<222> LOCATION: (21)..(21)
<223> OTHER INFORMATION: Xaa is K(mmt)

<400> SEQUENCE: 10

Lys Arg Xaa His His Asn Xaa Leu Glu Arg Lys Arg Arg Asp His Ile
1               5                   10                  15

Lys Asp Ser Xaa Xaa
            20

<210> SEQ ID NO 11
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (22)..(22)
<223> OTHER INFORMATION: Xaa is beta-alanine
<220> FEATURE:
<221> NAME/KEY: MISC_FEATURE
<222> LOCATION: (23)..(23)
<223> OTHER INFORMATION: Xaa is K(cpd)

<400> SEQUENCE: 11

Lys Arg Ala His His Asn Ala Leu Glu Arg Lys Arg Arg Asp His Ile
1               5                   10                  15

Lys Asp Ser Phe His Xaa Xaa Trp
            20

<210> SEQ ID NO 12
<211> LENGTH: 21
<212> TYPE: PRT
<213> ORGANISM: Artificial Sequence
<220> FEATURE:
<223> OTHER INFORMATION: synthetic
```

```
<220> FEATURE:
<221> NAME/KEY: MISC_FEATURE
<222> LOCATION: (3)..(3)
<223> OTHER INFORMATION: Xaa is S5
<220> FEATURE:
<221> NAME/KEY: MISC_FEATURE
<222> LOCATION: (7)..(7)
<223> OTHER INFORMATION: Xaa is S5
<220> FEATURE:
<221> NAME/KEY: MISC_FEATURE
<222> LOCATION: (20)..(20)
<223> OTHER INFORMATION: Xaa is beta-alanine
<220> FEATURE:
<221> NAME/KEY: MISC_FEATURE
<222> LOCATION: (21)..(21)
<223> OTHER INFORMATION: Xaa is K(cpd)

<400> SEQUENCE: 12

Lys Arg Xaa His His Asn Xaa Leu Glu Arg Lys Arg Arg Asp His Ile
1               5                   10                  15

Lys Asp Ser Xaa Xaa
            20

<210> SEQ ID NO 13
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(tBuS)
<220> FEATURE:
<221> NAME/KEY: MISC_FEATURE
<222> LOCATION: (5)..(5)
<223> OTHER INFORMATION: Xaa is K(Mmt)

<400> SEQUENCE: 13

Xaa Arg Gly Asp Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(Hex)
<220> FEATURE:
<221> NAME/KEY: MISC_FEATURE
<222> LOCATION: (5)..(5)
<223> OTHER INFORMATION: Xaa is K(Mmt)

<400> SEQUENCE: 14

Xaa Arg Gly Asp Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic

<400> SEQUENCE: 15

Cys Arg Gly Asp Lys
1               5
```

<210> SEQ ID NO 16
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(tBuS)

<400> SEQUENCE: 16

Xaa Val Gly Asp Lys
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(Hex)

<400> SEQUENCE: 17

Xaa Val Gly Asp Lys
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(tBuS)

<400> SEQUENCE: 18

Xaa Ala Pro Val Tyr Lys
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(Hex)

<400> SEQUENCE: 19

Xaa Ala Pro Val Tyr Lys
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Cys Ala Val Pro Ala Val Tyr Lys
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(tBuS)

<400> SEQUENCE: 21

Xaa Ala Val Pro Ala Val Tyr Lys
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is C(Hex)

<400> SEQUENCE: 22

Xaa Ala Val Pro Ala Val Tyr Lys
1               5

<210> SEQ ID NO 23
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is S5
<220> FEATURE:
<221> NAME/KEY: MISC_FEATURE
<222> LOCATION: (14)..(14)
<223> OTHER INFORMATION: Xaa is S5

<400> SEQUENCE: 23

Gln Ser Gln Gln Thr Phe Xaa Asn Leu Trp Arg Leu Leu Xaa Gln Asn
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: Xaa is A(Fur)

<400> SEQUENCE: 24

Gln Ser Gln Gln Thr Phe Lys Asn Leu Trp Arg Leu Leu Xaa Gln Asn
1               5                   10                  15

<210> SEQ ID NO 25
<211> LENGTH: 16
<212> TYPE: PRT

```
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is K(mal)
<220> FEATURE:
<221> NAME/KEY: MISC_FEATURE
<222> LOCATION: (14)..(14)
<223> OTHER INFORMATION: Xaa is A(Fur)

<400> SEQUENCE: 25

Gln Ser Gln Gln Thr Phe Xaa Asn Leu Trp Arg Leu Leu Xaa Gln Asn
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: synthetic

<400> SEQUENCE: 26

His Lys Ile Leu His Arg Leu Leu Gln Asp Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is K(mal)
<220> FEATURE:
<221> NAME/KEY: MISC_FEATURE
<222> LOCATION: (7)..(7)
<223> OTHER INFORMATION: Xaa is A(Fur)

<400> SEQUENCE: 27

His Lys Xaa Leu His Arg Xaa Leu Gln Asp Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is S5
<220> FEATURE:
<221> NAME/KEY: MISC_FEATURE
<222> LOCATION: (6)..(6)
<223> OTHER INFORMATION: Xaa is K(mal)
<220> FEATURE:
<221> NAME/KEY: MISC_FEATURE
<222> LOCATION: (7)..(7)
<223> OTHER INFORMATION: Xaa is S5
<220> FEATURE:
<221> NAME/KEY: MISC_FEATURE
<222> LOCATION: (10)..(10)
<223> OTHER INFORMATION: Xaa is A(Fur)

<400> SEQUENCE: 28

His Lys Xaa Leu His Xaa Xaa Leu Gln Xaa Ser
1               5                   10
```

```
<210> SEQ ID NO 29
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is K(mal)
<220> FEATURE:
<221> NAME/KEY: MISC_FEATURE
<222> LOCATION: (10)..(10)
<223> OTHER INFORMATION: Xaa is A(Fur)

<400> SEQUENCE: 29

His Lys Ile Leu His Xaa Leu Leu Gln Xaa Ser
1               5                   10

<210> SEQ ID NO 30
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is fitc-b-Ser

<400> SEQUENCE: 30

Xaa Leu Thr Glu Arg His Lys Ile Leu His Arg Leu Leu Gln Glu
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is A(Fur)

<400> SEQUENCE: 31

His Lys Lys Leu His Arg Xaa Leu Gln Asp Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: Xaa is A(Fur)

<400> SEQUENCE: 32

His Lys Ile Leu His Lys Leu Leu Gln Xaa Ser
1               5                   10

<210> SEQ ID NO 33
<211> LENGTH: 11
<212> TYPE: PRT
<213> ORGANISM: Artificial Sequence
<220> FEATURE:
```

```
<223> OTHER INFORMATION: synthetic
<220> FEATURE:
<221> NAME/KEY: MISC_FEATURE
<222> LOCATION: (3)..(3)
<223> OTHER INFORMATION: Xaa is S5
<220> FEATURE:
<221> NAME/KEY: MISC_FEATURE
<222> LOCATION: (7)..(7)
<223> OTHER INFORMATION: Xaa is S5
<220> FEATURE:
<221> NAME/KEY: MISC_FEATURE
<222> LOCATION: (10)..(10)
<223> OTHER INFORMATION: Xaa is A(Fur)

<400> SEQUENCE: 33

His Lys Xaa Leu His Lys Xaa Leu Gln Xaa Ser
1               5                   10

<210> SEQ ID NO 34
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is Fmoc-beta-Trp
<220> FEATURE:
<221> NAME/KEY: MISC_FEATURE
<222> LOCATION: (4)..(4)
<223> OTHER INFORMATION: Xaa is S5
<220> FEATURE:
<221> NAME/KEY: MISC_FEATURE
<222> LOCATION: (8)..(8)
<223> OTHER INFORMATION: Xaa is S5

<400> SEQUENCE: 34

Xaa Pro Gln Xaa Ile Leu Asp Xaa His Val Gln Glu Val Trp Arg Arg
1               5                   10                  15

Arg Arg Arg

<210> SEQ ID NO 35
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is beta-Trp
<220> FEATURE:
<221> NAME/KEY: MISC_FEATURE
<222> LOCATION: (4)..(4)
<223> OTHER INFORMATION: Xaa is S5
<220> FEATURE:
<221> NAME/KEY: MISC_FEATURE
<222> LOCATION: (8)..(8)
<223> OTHER INFORMATION: Xaa is S5

<400> SEQUENCE: 35

Xaa Pro Gln Xaa Ile Leu Asp Xaa His Val Gln Glu Val Trp Arg Arg
1               5                   10                  15

Arg Arg Arg

<210> SEQ ID NO 36
<211> LENGTH: 196
<212> TYPE: PRT
<213> ORGANISM: Artificial Sequence
<220> FEATURE:
```

<223> OTHER INFORMATION: synthetic

<400> SEQUENCE: 36

```
His His His His His Ser Ser Gly Leu Val Pro Arg Gly Ser His
1               5                   10                  15

Met Gly Asn Gly Thr Glu Glu Asp Tyr Asn Phe Val Phe Lys Val Val
                20                  25                  30

Leu Ile Gly Glu Ser Gly Val Gly Lys Thr Asn Leu Leu Ser Arg Phe
            35                  40                  45

Thr Arg Asn Glu Phe Ser His Asp Ser Arg Thr Thr Ile Gly Val Glu
        50                  55                  60

Phe Ser Thr Arg Thr Val Met Leu Gly Thr Ala Ala Val Lys Ala Gln
65                  70                  75                  80

Ile Trp Asp Thr Ala Gly Leu Glu Arg Tyr Arg Ala Ile Thr Ser Ala
                85                  90                  95

Tyr Tyr Arg Gly Ala Val Gly Ala Leu Leu Val Phe Asp Leu Thr Lys
                100                 105                 110

His Gln Thr Tyr Ala Val Val Glu Arg Trp Leu Lys Glu Leu Tyr Asp
            115                 120                 125

His Ala Glu Ala Thr Ile Val Val Met Leu Val Gly Asn Lys Ser Asp
        130                 135                 140

Leu Ser Gln Ala Arg Glu Val Pro Thr Glu Glu Ala Arg Met Phe Ala
145                 150                 155                 160

Glu Asn Asn Gly Leu Leu Phe Leu Glu Thr Ser Ala Leu Asp Ser Thr
                165                 170                 175

Asn Val Glu Leu Ala Phe Glu Thr Val Leu Lys Glu Ile Phe Ala Lys
                180                 185                 190

Val Ser Lys Gln
        195
```

<210> SEQ ID NO 37
<211> LENGTH: 196
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(26)
<223> OTHER INFORMATION: Xaa is TAG site
<220> FEATURE:
<221> NAME/KEY: misc_feature
<222> LOCATION: (194)..(194)
<223> OTHER INFORMATION: Xaa is TAG site

<400> SEQUENCE: 37

```
His His His His His Ser Ser Gly Leu Val Pro Arg Gly Ser His
1               5                   10                  15

Met Gly Asn Gly Thr Glu Glu Asp Tyr Xaa Phe Val Phe Lys Val Val
                20                  25                  30

Leu Ile Gly Glu Ser Gly Val Gly Lys Thr Asn Leu Leu Ser Arg Phe
            35                  40                  45

Thr Arg Asn Glu Phe Ser His Asp Ser Arg Thr Thr Ile Gly Val Glu
        50                  55                  60

Phe Ser Thr Arg Thr Val Met Leu Gly Thr Ala Ala Val Lys Ala Gln
65                  70                  75                  80

Ile Trp Asp Thr Ala Gly Leu Glu Arg Tyr Arg Ala Ile Thr Ser Ala
                85                  90                  95
```

-continued

```
Tyr Tyr Arg Gly Ala Val Gly Ala Leu Leu Val Phe Asp Leu Thr Lys
            100             105                 110

His Gln Thr Tyr Ala Val Val Glu Arg Trp Leu Lys Glu Leu Tyr Asp
        115                 120                 125

His Ala Glu Ala Thr Ile Val Val Met Leu Val Gly Asn Lys Ser Asp
        130             135                 140

Leu Ser Gln Ala Arg Glu Val Pro Thr Glu Glu Ala Arg Met Phe Ala
145             150                 155                     160

Glu Asn Asn Gly Leu Leu Phe Leu Glu Thr Ser Ala Leu Asp Ser Thr
                165             170                 175

Asn Val Glu Leu Ala Phe Glu Thr Val Leu Lys Glu Ile Phe Ala Lys
            180                 185                 190

Val Xaa Lys Gln
        195
```